(12) United States Patent
Fahl et al.

(10) Patent No.: US 7,314,959 B2
(45) Date of Patent: Jan. 1, 2008

(54) AMINO THIOL COMPOUNDS AND COMPOSITIONS FOR USE IN CONJUNCTION WITH CANCER THERAPY

(75) Inventors: William E. Fahl, Madison, WI (US); Daniel D. Peebles, Fond du Lac, WI (US); Richard C. Copp, Oregon, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 140 days.

(21) Appl. No.: 10/915,089

(22) Filed: Aug. 9, 2004

(65) Prior Publication Data

US 2005/0101676 A1    May 12, 2005

Related U.S. Application Data

(60) Provisional application No. 60/493,218, filed on Aug. 7, 2003.

(51) Int. Cl.
*C07C 211/22* (2006.01)
*C07C 323/27* (2006.01)
*C07C 215/24* (2006.01)
*A61K 31/131* (2006.01)

(52) U.S. Cl. ............... 564/512; 564/500; 564/503; 564/509; 514/665; 514/667; 514/671; 514/674

(58) Field of Classification Search .................. None
See application file for complete search history.

(56) References Cited

U.S. PATENT DOCUMENTS

| | | | |
|---|---|---|---|
| 3,773,833 A | 11/1973 | Henrici et al. | 260/583 H |
| 5,217,964 A | 6/1993 | Edwards et al. | 514/104 |
| 5,292,497 A | 3/1994 | Schein et al. | 424/10 |
| 5,434,145 A | 7/1995 | Edwards et al. | 514/108 |
| 5,541,230 A | 7/1996 | Basu et al. | 514/642 |
| 5,627,215 A | 5/1997 | Frei et al. | 514/674 |
| 5,889,061 A | 3/1999 | Frydman et al. | 514/674 |
| 5,962,533 A | 10/1999 | Bergeron, Jr. | 514/674 |
| 6,172,261 B1 | 1/2001 | Vermeulin et al. | 564/84 |
| 6,239,119 B1 | 5/2001 | Stogniew et al. | 514/131 |
| 2003/0022867 A1 | 1/2003 | Stogniew et al. | 514/114 |
| 2003/0118539 A1 | 6/2003 | Fahl et al. | 424/70.17 |

FOREIGN PATENT DOCUMENTS

| | | |
|---|---|---|
| WO | WO 94/19311 A1 | 9/1994 |
| WO | WO 94/27961 A1 | 12/1994 |
| WO | WO 98/17624 A1 | 4/1998 |
| WO | WO 00/66587 A3 | 11/2000 |
| WO | WO 00/78289 A1 | 12/2000 |
| WO | WO 01/85142 1 | 11/2001 |
| WO | WO 02/38105 A3 | 5/2002 |
| WO | WO 03/013245 A1 | 2/2003 |
| WO | WO 03/066572 A1 | 8/2003 |

OTHER PUBLICATIONS

Database CAPLUS on STN, Acc. No. 1985:560304, Furukawa et al., EP 144825 (Jun. 19, 2006) (abstract).*
Alvarez, E., et al., "Preclinical characterization of CG53135 (FGF-20) in radiation and concomitant chemotherapy/radiation-induced oral mucositis," *Clin. Cancer Research*, 2003, 9, 3454-3461.
Aphramaian, M., et al., "Transmucosal passage of polyalkylcyanoacrylate nanocapsules as a new drug carrier in the small intestine," *Biol. of the Cell*, 1987, 61, 69-76.
Basu, H., et al., "The interaction of spermine and pentamines with DNA," *Biochem. J.*, 1987, 244, 243-246.
Basu, H., et al., "Effects of variation in the structure of spermine on the association with DNA and the induction of DNA conformational changes," *Biochem. J.*, 1990, 269, 329-334.
Basu, H., et al., "Correlation between the effects of polyamine analogues on DNA conformation and cell growth," *Cancer Res.*, 1989, 49, 5591-5597.
Chen, G., et al., "Protection against cyclophosphamide-induced alopecia and inhibition of mammary tumor growth by topical 1,25-dihydroxyvitamin $D_3$ in mice," *Int. J. Cancer*, 1998, 75, 303-309.
Creaven, P., et al., "Unusual central nervous system toxicity in a phase I study of $N^1N^1$ diethylnorspermine in patients with advanced malignancy," *Invest. New Drugs*, 1997, 15, 227-234.
Desai, M.P., et al., "The mechanism of uptake of biodegradable microparticles in Caco-2 cells is size dependent," *Pharm. Res.*, 1997, 14(11), 1568-1573.
Ellouk-Achard, S., et al., "Ex Vivo and Ex Vitro models in acetaminophen hepatotoxicity studies. Relationship between glutathione depletion, oxidative stress and disturbances in calcium homeostasis and energy metabolism," Arch. *Toxicol. Suppl.*,1995, 17, 209-214.
Feuerstein, B., et al., "Molecular dynamics of spermine—DNA interations: sequence specificity and DNA bending for a simple ligand," *Nuc. Acids Res.*, 1989, 17(17), 6883-6892.
Gao, X., et al., "Radioprotective effect of epinephrine as a vasoconstrictor in mouse oral mucosa and scalp," *Okayama Igakkai Zasshi*, 1996, 108, 139-144 (Translation).
Hillery, A.M., et al., "Comparative, quantitative study of lymphoid and non-lymphoid uptake of 60nm polystyrene particles," *J. Drug Targeting*, 1994, 2, 151-156.
Ho, D., et al., "Modification of glutathione levels in C3H/1OT1/2 cells and its relationship to benzo(α)pyrene anti-7,8-dihydrodiol 9,10-epoxide-induced cytotoxicity," *J. Biol. Chem.*, 1984, 259(18), 11231-11235.

(Continued)

*Primary Examiner*—Brian Davis
(74) *Attorney, Agent, or Firm*—Quarles & Brady LLP

(57) ABSTRACT

The invention provides novel polyamine and amino thiol compounds and pharmaceutical compositions for administration in conjunction with cancer chemotherapy or radiation therapy. The compounds are administered locally to provide protection against the adverse side-effects of chemotherapy or radiation therapy, such as alopecia, mucositis and dermatitis. Pharmaceutical preparations comprising one or more chemoprotective polyamines or amino thiols formulated for topical or local delivery to epithelial or mucosal cells are disclosed. Methods of administering the pharmaceutical preparations are also disclosed.

71 Claims, 28 Drawing Sheets

OTHER PUBLICATIONS

Huber, M., et al., "2,2'-dithiobis(N-ethyl-spermine-5-carboxamide) is a high affinity, membrane-impermeant antagonist of the mammalian polyamine transport system," *J. Biol. Chem.*, 1996, 217(44), 27556-27563.

Hussein, A.M., et al., "Protection from chemotherapy-induced alopecia in a rat model," *Science*, 1990, 249, 1564-1566.

Jayaraman, S.C., et al., "Topical delivery of erythromycin from various formulations: an in vivo hairless mouse study," *J. Pharm. Sci.*, 1996, 85(10), 1082-1084.

Jeitner, T.M., et al., "Inhibition of the proliferation of human neural neoplastic cell lines by cysteamine," *Cancer Lett.*, 1996, 103(1), 85-90.

Kramer, D.L., et al., "Polyamine analogue induction of the p. 53-p. 21 $^{WAFI/CIP1}$-Rb pathway and $G_1$ arrest in human melanoma cells," *Cancer Res.*, 1999, 59, 1278-1286.

Kramer, D.L., et al., "Effects of novel spermine analogues on cell cycle progression and apoptosis in MALME-3M human melanoma cells," *Cancer Res.*, 1997, 57, 5521-5527.

Kramer, D.L., et al., "Polyamine depletion in human melanoma cells leads to $G_1$ arrest associated with induction of P. $21_{WAFI/CIP1/SDII}$, changes in the expression of p.21-regulated genes, and a senescence-like phenotype," *Cancer Res.*, 2001, 61, 7754-7762.

Levy, E., et al., "Transport of glutathione diethyl ester into human cells," *Proc. Natl. Acad. Sci. USA*, 1993, 90(19), 9171-9175.

Lowy, R.O., et al., "Protection against local irradiation injury to the skin by locally and systemically applied drugs," *Radiation Biology*, 1972, 105, 425-428.

March, J., Advanced Organic Chemistry: Reactions, Mechanisms, and Structure, 4$^{th}$ Ed., *John Wiley & Sons*, 1992, 771-780.

Masuda, K., et al., "Response of previously irradiated mouse skin to a second course of irradiation: early skin reaction and skin shrinkage," *Int. J. Radiation Oncol. Biol. Phys.*, 1986, 12, 1645-1651.

Purdie, J.W., "A comparative study of the radioprotective effects of cysteamine, WR-2721, and WR-1065 in cultured human cells," *Radiation Res.*, 1979, 77, 303-311.

Snyder, R.D., et al., "Further evidence that the radioprotective aminothiol, WR-1065, catalytically inactivates mammalian topoisomerase II," *Cancer Res.*, 2000, 60, 1186-1188.

Sonis, S.T., et al., "Defining mechanisms of action of interleukin-11 on the progression of radiation-induced oral mucositis in hamsters," *Oral Oncology*, 2000, 36, 373-381.

Spotheim-Maurizot, M., "radioprotection of DNA by polyamines," *Int. J. Radiat. Biol.*, 1995, 68(5), 571-577.

Streiff, R., et al., "Phase 1 study of $N^1$-$N^{11}$-diethylnorspermine (DENSPM) administered TID for 6 days in patients with advanced malignancies," *Invest. New Drugs*, 2001, 19, 29-39.

Verhey, L.J., et al., "Determination of the radioprotective effects of topical applications of MEA, WR-2721, and N-acetylcysteine on murine skin," *Radiation Res.*, 1983, 93, 175-183.

U.S. Appl. No. 09/565,714, filed May 5, 2000, Fahl et al.

U.S. Appl. No. 10/214,917, filed Aug. 7, 2002, Fahl et al.

Piper, J.R., et al., "S-2,ω-diaminoalkyl dihydrogen phosphorothioates as antiradiation agents," *Am. Chem. Soc.*, 1979, 631-639.

* cited by examiner

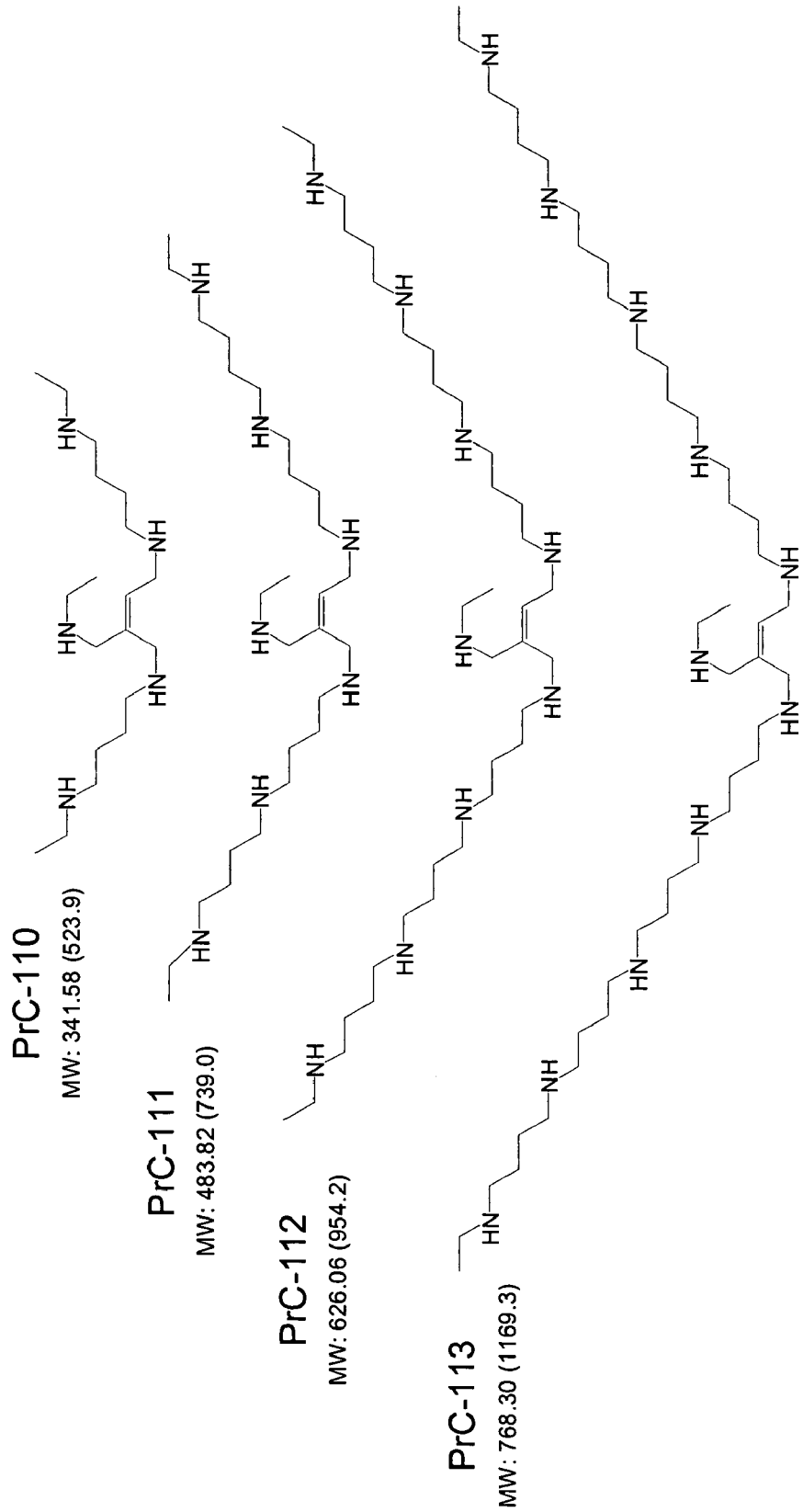

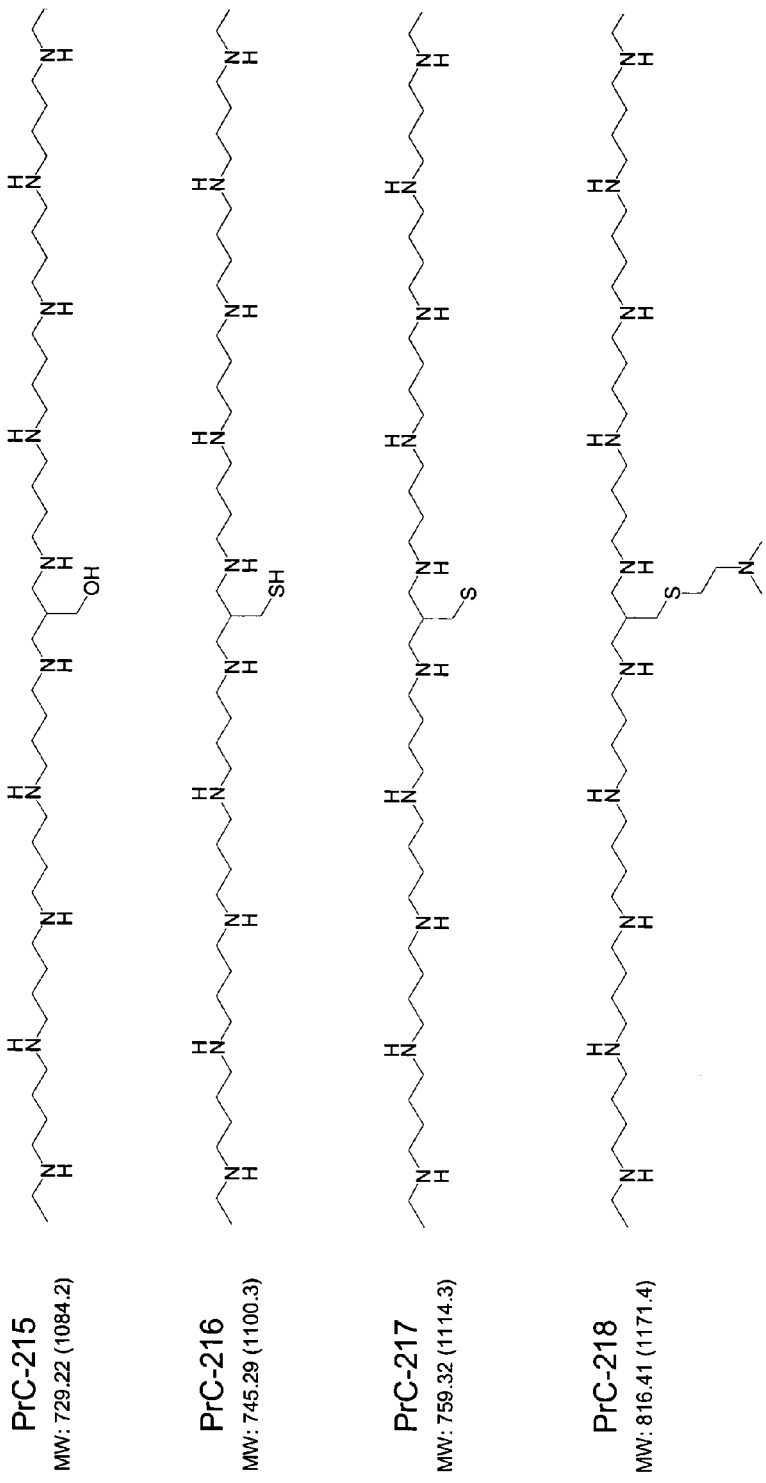

Fig. 3A
Fig. 3B
Human Dermal Fibroblasts
Human Dermal Fibroblasts
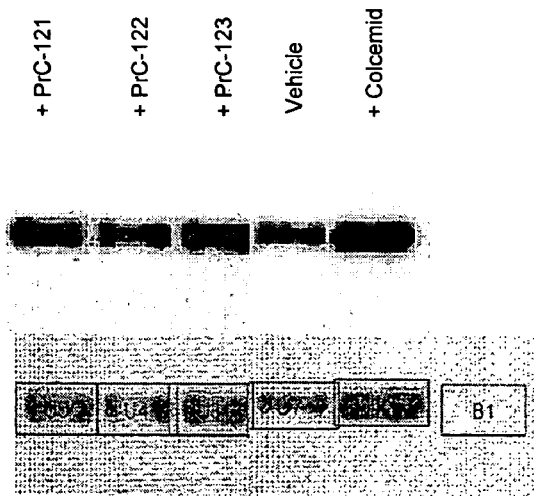

1-Amino-3-methylamino-propane-2-thiol 1,3-Bis-methylamino-propane-2-thiol 2-(2-Methylamino-1-methylaminomethyl-ethyl)-propane-1,3-dithiol 4-Methylamino-3-methylaminomethyl-butane-1,2-dithiol 2-(2-Amino-1-aminomethyl-ethyl)-propane-1,3-dithiol 4-Amino-3-aminomethyl-butane-1,2-dithiol FIG. 8C
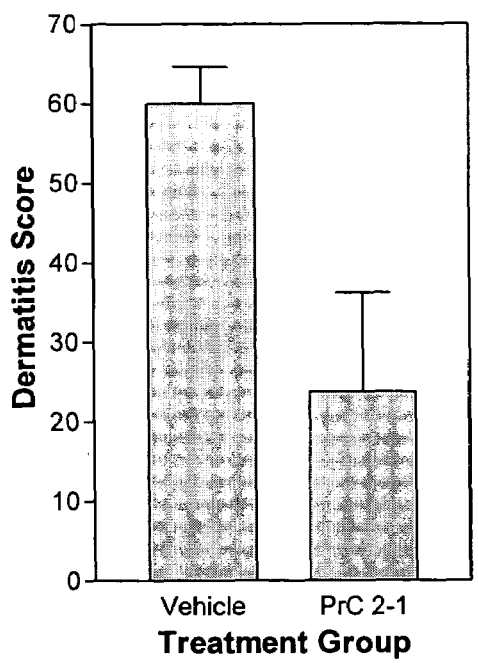
FIG. 8D
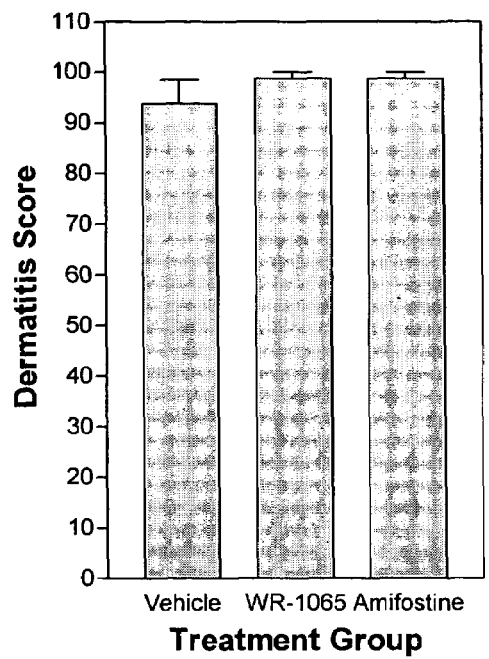
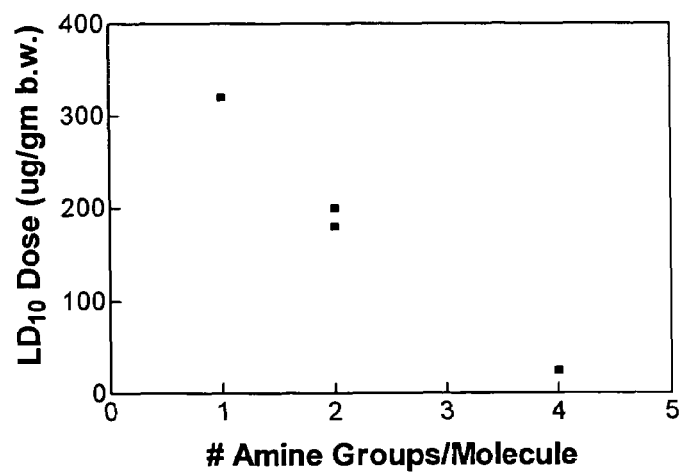
FIG. 8E

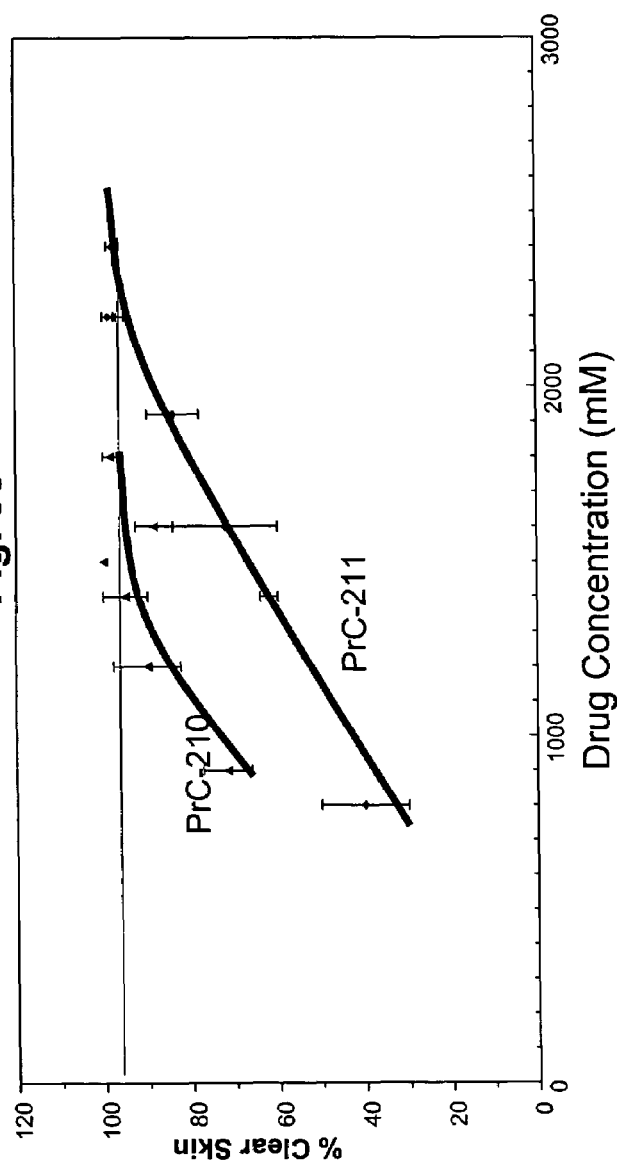
Fig. 9c
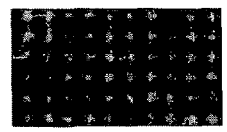
100 % Clear Skin
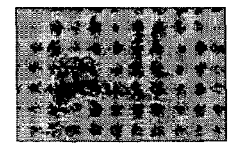
~25% Clear Skin
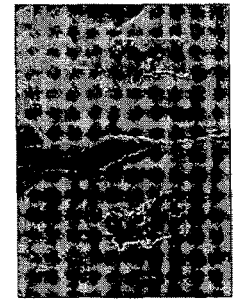
0% Clear Skin

PrC-210 is a potent scavenger of oxygen free radicals

Addition of PrC-210 to a reaction containing plasmid DNA confers 100% protection against damage caused by OH* that is generated using an $H_2O_2$-UV light system Nicked/Circular
Supercoiled pUC19
Plasmid DNA Mass spectral analysis of PrC-210 added to DNA/$H_2O_2$ reaction shows conversion of the reduced drug form to its oxidized form as $H_2O_2$-derived oxygen radical is scavenged away from DNA by PrC-210

AMINO THIOL COMPOUNDS AND COMPOSITIONS FOR USE IN CONJUNCTION WITH CANCER THERAPY

CROSS-REFERENCE TO RELATED APPLICATION

This claims priority to U.S. Provisional Application 60/493,218 filed Aug. 7, 2003, the entirety of which is incorporated herein by reference.

Pursuant to 35 U.S.C. §202 (c), it is acknowledged that the United States Government has certain rights in the invention described herein, which was made in part with funds from the National Institutes of Health, Grant No. CA22484.

FIELD OF THE INVENTION

The present invention relates to the field of cancer therapy. More particularly, it relates to novel amino thiols and other compounds and pharmaceutical compositions for reducing or preventing toxic side effects of radiotherapy or chemotherapeutic agents.

BACKGROUND OF THE INVENTION

Various patents and other publications are referenced throughout the specification. The disclosure of each of these publications is incorporated in its entirety by reference herein.

It is well known that the use of chemotherapy and radiotherapy to treat cancer patients is associated with severe side effects due to the toxicity of such treatments to cells, particularly epithelial cell populations, including stem cells, within the hair follicle, skin epidermis, and gastrointestinal mucosa.

Currently, there are no treatments to prevent cancer therapy side effects. Effective treatments would likely include molecules that i) inhibit or slow growth of the at-risk cells, ii) modify the cellular DNA of the at-risk cells to make it less easily damaged, and iii) provide some means with which to scavenge electrophilic drug metabolites or oxygen radicals formed during irradiation.

Polyamines and other amine compounds have been proposed as growth regulators. DENSPM, a synthetic analog of spermine, has been shown to decrease cell growth (Kramer et al., *Cancer Res*. 57:5521-5527, 1997), and has been studied in an early stage clinical trial as an antineoplastic drug (Creaven, P. et al., *Invest. New Drugs* 15:227-234, 1997; Streiff, R and Bender, *J. Invest. New Drugs* 19:29-39, 2001). The clinical trials, however, were aborted because of the serious side effects in multiple organ sites that were associated with the systemic use of this polyamine analog. These results teach that molecules used to decrease division of healthy stem cells that are at risk from cancer therapy would need to create a transient cell cycle block and would need to be applied topically to achieve local delivery to epithelial cells, with little or no systemic delivery, or if any, low enough to preclude protection of systemic cancer cells or induction of systemic side effects.

Naturally occurring polyamines, such as spermine, have been shown to bind to nucleic acids and to induce structural changes in helical DNA (Basu, H. and Marton, L., *Biochem. J*. 244:243-246, 1987; Feuerstein, B. et al., *Nuc. Acids Res*. 17:6883-6892, 1989). This binding has been suggested to occur through interaction of the positively-charged amine groups in the polyamine backbone and negatively-charged sites on the DNA backbone. Because of the manner in which electrophilic chemotherapy drugs or oxygen radicals generated by radiotherapy attack helical B-DNA within cells, the ability of polyamines to bind DNA and disrupt normal B-DNA structure could be helpful in protecting DNA within cells to which a polyamine was delivered.

An additional strategy for protecting cells against electrophiles/radicals has been to augment levels of the naturally occurring cellular nucleophile, glutathione (GSH). Both animal and cell culture studies have shown that there is a direct relationship between the intracellular concentration of GSH and the amount of exogenously administered alkylating molecule that is needed to achieve cell kill (Ho, D. and Fahl, W., *J. Biol. Chem*. 259:11231-11235, 1984; Ellouk-Achard, S. et al., *Arch. Toxicol. Suppl*. 17:209-214, 1995). Efforts to exogenously administer GSH to cells as a protectant have failed because mammalian cells are generally unable to take up this nucleophile. There have been efforts to modify the GSH molecule to enable cellular uptake, but these have not found clinical use.

Amifostine (WR-2721), a small molecule amine containing a thiophosphate group that is presumably converted to a thiol in cells, has been used systemically as a radio- and chemoprotectant with mixed results. Though it may provide free —SH groups within cells, it is not known to contain activity as either a growth regulator or as a modifier of DNA structure. The active metabolite of WR-2721, WR-1065, has been shown to be active as a radioprotector when added to cells in tissue culture, as has another small molecule, cysteamine (Purdie, J. W., *Radiation Research* 77:303-311, 1979). U.S. Pat. No. 6,239,119 (and published U.S. Patent Application No. 2003/0022867 A1) to Stogniew and Bourhis suggests the use of WR-2721, WR-1065 and their related metabolites as topical radio- or chemo-protectors. The published literature, however, contains little information about topical use of such small molecules, and the information that is published teaches the failure of these compounds as topically-applied protector molecules. Lowy et al. (*Radiation Biology* 105:425-428, 1972) reported that although systemic amifostine was effective in reducing radiation-induced skin damage in mice, topical application of the drug showed no protective effect. Verhey et al., (*Radiation Research* 93:175-183, 1983) also reported no protective effect when amifostine was applied topically to mouse skin.

Edwards et al. (U.S. Pat. Nos. 5,217,964 and 5,434,145) described the synthesis of short, spermidine- or spermine-like polyamine molecules that were modified to contain an alkyl-thiophosphate or alkyl-thiol group. In U.S. Pat. No. 5,217,964, the attached thiophosphate group (i.e., —$SPO_3H_2$) would require enzymatic activation by cellular phosphatases to form the nucleophilic —SH group. The alkyl-thiophosphate group(s) was bound to the polyamine molecule through a terminal benzyl ring and/or through one or more of the amines in the polyamine backbone. Polyamines containing aromatic rings have been described as structural inhibitors of the membrane polyamine transporter in mammalian cells. Such polyamines have been shown not to be transported into cells. In U.S. Pat. No. 5,434,145, Edwards showed bonding of alkyl-thiophosphate or alkyl-thiol groups to one or more of the backbone amines that are present in the short polyamine molecules. By modifying the secondary amines in the polyamine backbone with alkyl-thiophosphate groups, the amines were converted to tertiary amines, and this markedly altered the basicity of the individual modified amine, as well as that of the overall polyamine molecule. The attenuated basicity of the individual amine groups was accompanied by an alteration in three dimensional structure at these sites. With added alkyl functionality on the amine nitrogen atoms, steric bulkiness was increased, so the ability or freedom of the molecule to rotate and twist at these sites was markedly reduced. The altered basicity and steric constraints in these short spermine-like polyamines was surmised to perturb DNA binding by the modified polyamines, as compared to that of their natural polyamine counterparts. Consistent with this (DNA binding is a biological activity of natural polyamines), Edwards provided no information regarding biological activity for any of the structures proposed in U.S. Pat. No. 5,217,964 or 5,434,145. Similarly in U.S. Pat. No. 5,292,497, Schein et al. describe a method of reducing chemotherapy toxicity involving oral administration of S-3-(3-methylaminopropylamino) propyl dihydrogen phosphorothioate compounds.

Accordingly, there is a need in the art to create polyamine and other amine-based molecules that are optimized to achieve: i) local and transient growth regulation, ii) disruption of normal helical DNA structure upon binding, and iii) delivery and display of nucleophilic or other functional moieties within cells to enable scavenging of reactive electrophiles and radicals. There would be great advantage in developing compounds that can be used topically to prevent or diminish the toxic side effects of cancer chemotherapy and radiotherapy.

SUMMARY OF THE INVENTION

The present invention provides, in several of its aspects, novel polyamine and amino thiol compounds, and pharmaceutical compositions for reducing or preventing toxic side effects of radiotherapy and cancer chemotherapeutic agents. The polyamine and amino thiol compounds of the invention are referred to herein as "chemoprotective polyamines" and "chemoprotective amino thiols," respectively. The compounds are sometimes referred to collectively as "chemoprotective amines."

One aspect of the invention features a compound of Formula I:

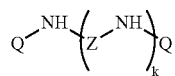

I wherein:

each Z is independently A or $R^1$, provided that at least one Z is A;

each A is independently:

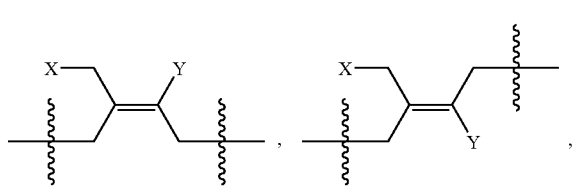

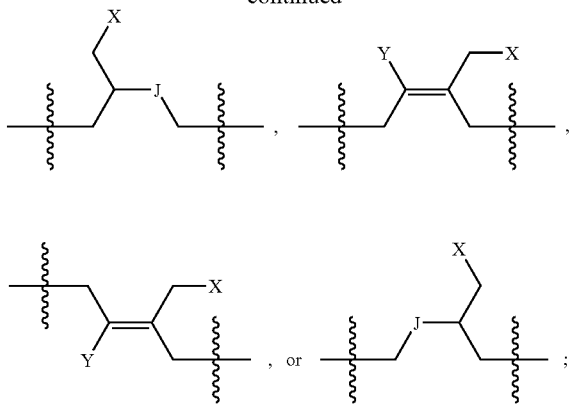

J is a single bond or —CH(Y)—;
X is D or —$R^2$-D;
Y is H, alkyl, or $R^3$-D;
D is —OH, —SH, —$SR^4$, or —$NR^4R^5$;
each $R^1$ is independently $C_{3-8}$ alkylene;
each $R^2$, $R^3$, $R^6$, and $R^7$ is independently $C_{1-6}$ alkylene;
$R^4$ is H or lower alkyl;
$R^5$ is H, lower alkyl, or —$R^6$-D;
each Q is independently H, lower alkyl, or —$R^7$—$SR^4$;
k is an integer from 2 to about 16;
or a stereoisomer, prodrug, pharmaceutically-acceptable salt, or mono or polyprotonated acid salt thereof.

In certain embodiments, each A is independently:

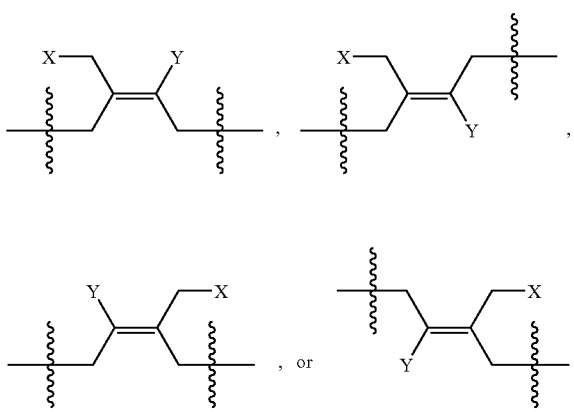

In such embodiments, Y may be H or $R^3$-D. X may be D or $R^2$-D. In such embodiments, k is an integer from 2 to about 16. In specific embodiments, k is 2, 3, 4, 5, 6, 7 or 8. In other embodiments, k is 2-8, each $R^1$ is butylene, X is D, D is —$NR^4R^5$, $R^4$ is H, and $R^5$ is ethyl, and Q is ethyl. In yet other specific embodiments, k is 2, 4, 6 or 8, each $R^1$ is butylene, X is D, D is —SH, and Q is ethyl. Yet another embodiment comprises a compound wherein k is 4, each $R^1$ is butylene, X is D, D is —$NR^4R^5$, $R^4$ is H, $R^5$ is methyl, and Q is ethyl. In other embodiments, Q is H or lower alkyl. Exemplary compounds having these features are shown in FIG. 1A through FIG. 1C.

In another embodiment, each A is independently:

[chemical structure]

In this embodiment, Y may be H or $R^3$-D. X may be D or $R^2$-D. In this embodiment, k is an integer from 2 to about 16. In specific embodiments, k is 2, 3, 4, 5, 6, 7 or 8. Q may be H or lower alkyl. J is a single bond; in specific embodiments, J is —CH(Y)—. Exemplary compounds having the aforementioned features are shown in FIG. 1D and FIG. 1E.

Another aspect of the invention features a compound of Formula II:

[chemical structure]  II wherein:
A is:

[chemical structures]

J is a single bond or —CH(Y)—;
L is —$CH_2X^1$, —SH, —$CHX^2(X^3)$;
$X^1$ is SH or —$R^1$—SH;
$X^2$ and $X^3$ are each independently H, SH, or —$R^1$—SH, provided that at least one of $X^2$ and $X^3$ is other than H or SH;
Y is H, alkyl, or $R^2$-D;
D is —OH, —$SR^3$, or —$NR^3R^4$;
$R^3$ is H or lower alkyl;
$R^4$ is H, lower alkyl, or —$R^5$-D;
each Q is independently H, lower alkyl, or —$R^6$—$SR^3$, provided that when L is SH, at least one of Q is other than H; and
each $R^1$, $R^2$, $R^5$, and $R^6$ is independently $C_{1-6}$ alkylene;
or a stereoisomer, prodrug, pharmaceutically-acceptable salt, or mono or polyprotonated acid salt thereof.

Another aspect of the invention features a compound of Formula III:

[chemical structure]  III wherein:
$X^4$ is —SH or —$R^1$—SH;
$X^5$ is H, —SH or —$R^1$—SH, provided that at least one of $X^4$ and $X^5$ is other than —SH;
$B^1$ is —$CH_2NHR^7$, —$CH_2CH_2NHR^7$, —$CH_2CH_2CH_2NHR^7$, or —$CH(NH_2)CH_2NHR^7$; and
$R^7$ is H or lower alkyl, provided that when $B^1$ is —$CH_2NHR^7$, $R^7$ is other than H;
or a stereoisomer, prodrug, pharmaceutically-acceptable salt, or mono or polyprotonated acid salt thereof.

Still another aspect of the invention features a compound of Formula IV:

[chemical structure]  IV wherein:
$X^6$ and $X^7$ are each independently —$R^1$—SH;
$B^2$ is —$R^2$-$NHR^8$; and
$R^8$ is H or lower alkyl, provided that when $B^2$ is —$CH_2CH_2NHR^8$, $R^8$ is other than H;
or a stereoisomer, prodrug, pharmaceutically-acceptable salt, or mono or polyprotonated acid salt thereof.

Another aspect of the invention features the compound 3-dimethylamino-butane-2-thiol, 4-amino-3-methyl-pentane-2-thiol, 2-methyl-3-methylamino-propane-1-thiol, 4-methylamino-pentane-1-thiol, 3-methylamino-butane-1-thiol, 3-(3-mercapto-propylamino)-propane-1-thiol, 3,4-diaminobutane-1,2-dithiol, or 2-amino-2-aminomethyl-propane-1,3-dithiol.

Another aspect of the invention features a pharmaceutical preparation for reducing or preventing hair loss, dermatitis, mucositis or gastrointestinal distress caused by treatment with a chemotherapeutic agent or radiation therapy, which comprises at least one compounds as described above, and a topical delivery vehicle for locally delivering the compound to dermal or mucosal cells of skin, scalp, mouth, nasoesophageal, gastrointestinal or urogenital system. In certain embodiments, the pharmaceutical preparation further comprises at least one other agent that reduces or prevents hair loss, dermatitis, mucositis or gastrointestinal distress caused by treatment with a chemotherapeutic agent or radiation therapy, for instance, an anti-proliferative agent, a chemoprotective inducing agent or a free radical scavenger.

The topical delivery vehicle comprises one or more of liposomes, lipid droplet emulsions, oils, aqueous emulsions of polyoxyethylene ethers, aqueous alcohol mixtures, aqueous ethanol mixtures containing propylene glycol, aqueous ethanol mixtures containing phosphatidyl choline, lysophosphatidyl choline and triglycerides, xanthan gum in aqueous buffer, hydroxypropymethylcellulose in aqueous buffer or aqueous alcohol mixtures, diethylene glycol monoethyl ether in aqueous buffer, and biodegradable microparticles.

In a specific embodiment, the pharmaceutical preparation is formulated for topical delivery to skin or hair follicles, and the delivery vehicle comprises an aqueous alcohol mixture and, optionally, propylene glycol. Preparations of this type may be formulated as creams, lotions, ointments or gels. In another specific embodiment, the pharmaceutical preparation is formulated for topical delivery to the oral cavity or naso-esophageal passages. In this embodiment the delivery vehicle preferably comprises a mucoadhesive substance. It may be formulated as an aerosol, oral rinse, ointment or gel. In yet another specific embodiment, the pharmaceutical preparation is formulated for vaginal or rectal delivery and comprises a mucoadhesive substance. These preparations may be formulated as creams, ointments, lotions, gels, foams or suppositories. In still another specific embodiment, the pharmaceutical preparation is formulated for topical delivery to the gastrointestinal tract and the delivery vehicle comprises one or more of nonionic liposomes and mucoadhesive substances. Preferably, the preparation is formulated as a liquid for coating the surface of the gastrointestinal tract.

According to another aspect of the invention, methods are provided for reducing or preventing hair loss dermatitis, mucositis or gastrointestinal distress in a patient undergoing treatment with a chemotherapeutic agent or radiation therapy. The methods comprise administering to the patient a pharmaceutical preparation as described above, in an amount and for a time sufficient to reduce or prevent the hair loss, dermatitis, mucositis or gastrointestinal distress. In one embodiment, the pharmaceutical preparation is administered beginning at least 30 minutes, prior to chemotherapy or radiation therapy. In alternative embodiments it is administered earlier, e.g., 4-18 hours, or one day, or up to five or more days, prior to chemotherapy or radiation therapy. In another embodiment, the pharmaceutical preparation is administered after initiation of chemotherapy or radiation therapy. In specific embodiments, the pharmaceutical preparation is administered throughout a course of chemotherapy or radiation therapy and, in certain instances continues after termination of a course of chemotherapy or radiation therapy.

The aforementioned methods may further comprise administering to the patient at least one other agent that reduces or prevents hair loss, dermatitis, mucositis or gastrointestinal distress caused by treatment with a chemotherapeutic agent or radiation therapy. These other agents may include anti-proliferative agents, chemoprotective inducing agents or free radical scavengers, for instance.

The present invention also provides a method of treating cancer that increases a patient's tolerance to high doses of a chemotherapeutic agent or radiation therapy. The method comprises (a) administering the high dose of the chemotherapeutic agent or radiation therapy to the patient; and (b) administering one or more of the above-described pharmaceutical preparations for reducing or preventing one or more of chemotherapy- or radiation therapy-induced hair loss, dermatitis, mucositis or gastrointestinal distress, in an amount and for a time to reduce or prevent the one or more of the chemotherapy- or radiation therapy-induced hair loss, dermatitis, mucositis or gastrointestinal distress, thereby increasing the patient's tolerance to the high dose of the chemotherapeutic agent or radiation therapy.

Another aspect of the invention features pharmaceutical compositions and methods as described above, comprising cysteamine as the chemprotective agent, either alone or in combination with one or more other compounds as set forth herein.

In another of its several aspects, the invention provides methods of reducing or preventing hair loss in a patient undergoing treatment with a chemotherapeutic agent or radiation therapy, comprising administering to the patient a prophylactically- or therapeutically-effective amount of a pharmaceutical preparation comprising cysteamine and a topical delivery vehicle for locally delivering the compound to a site having hair follicles; and applying a vasoconstrictor topically at the site. The application of the vasoconstrictor may be at a time prior to, in conjunction with, or following the administering of the pharmaceutical preparation.

In another aspect, the invention provides methods of treating alopecia. Methods are provided for reducing or preventing hair loss in a patient undergoing treatment with a chemotherapeutic agent or radiation therapy, comprising the steps of (a) administering to the patient a prophylactically- or therapeutically-effective amount of a pharmaceutical preparation comprising at least one of 3-methylamino-2-methylaminomethyl-propane-1-thiol and 3-amino-2-aminomethyl-propane-1-thiol and a topical delivery vehicle for locally delivering the compound to a site having hair follicles; and (b) applying a vasoconstrictor topically at the site. The vasoconstrictor may be applied at a time prior to, in conjunction with, or following the administering of the pharmaceutical preparation.

These and other features and advantages of the aspects of the present invention will be understood by reference to the drawings, detailed description and examples that follow.

BRIEF DESCRIPTION OF THE DRAWINGS

FIG. 1A-FIG. 1E illustrate the structures of certain of the chemoprotective polyamine molecules whose synthetic pathways are illustrated in the reaction schemes. FIG. 1A shows compounds PrC 110, 111, 112 and 113, olefinic core displaying —NH—CH$_2$—CH$_3$ functional group; FIG. 1B shows compounds PrC 114, 115, 116, 117 and 118, olefinic core displaying —SH or —OH functional group; FIG. 1C shows compounds PrC 119, 120, 121, 122 and 123, olefinic core displaying —NHCH$_3$, —N(CH$_3$)$_2$ or —SH functional group; FIG. 1D shows compounds Prc 210, 211, 212, 213 and 214, aliphatic core displaying —OH, —SH, —SCH$_3$ or —NHCH$_2$CH$_3$ functional group; FIG. 1E shows compounds PrC 215, 216, 217 and 218, aliphatic core displaying —OH, —SH, —SCH$_3$ or —SCH$_2$CH$_2$N(CH$_3$)$_2$ functional group.

FIGS. 3A and 3B illustrate the level of induced p21 protein seen in diploid human fibroblasts after a 30 hr exposure to each of the indicated chemoprotective polyamines. FIG. 3B shows that the induced p21 level is greater after a 30 hr exposure compared to a 50 hr exposure to drug. In these experiments, the 23SK human skin cells were exposed for 30 hr to an "IC$_{80}$" dose of each of the indicated chemoprotective polyamines and then lysed. Cell extracts were then prepared in order to measure p21 levels by western analysis (FIG. 3A).

FIG. 5A shows results from untreated, exponentially growing 23SK cells. FIG. 5B shows, as a control treatment, results from incubation of cells in serum-free medium. FIG. 5C shows results from cells treated with PrC-117 for 72 hr. FIG. 5D shows results from cells treated with PrC-117 for 72 hr, then switched for 48 hr to medium devoid of the PrC-117 molecule.

FIGS. 8A-8E illustrate aspects of the efficacy of a topically-applied chemoprotective amino thiol compound (PrC2-1) in protecting against chemotherapy and radiation-induced dermatitis in vitro and in a rodent model. FIG. 8A illustrates the significant radioprotective effect seen when 23SK human skin cells are pretreated or 'loaded' with 4 mM PrC2-1 for 30 min prior to irradiation in a Cs137 irradiator for 38 min. FIG. 8B illustrates the significant protective effect seen when 23SK human skin cells are pretreated or 'loaded' with 4 mM PrC2-1 for 30 min prior to treatment with phosphoramide mustard (the active metabolite of cyclophosphamide) for 40 min. Growth of cells loaded with 4 mM WR-1065 or 4 mM amifostine was not significantly different than that seen in the vehicle control. FIG. 8C illustrates the significant protective effect seen when rats were treated topically with PrC2-1 in a carrier vehicle prior to irradiation of a defined rectangular field on the animal's back for 5.1 min in a Cs137 irradiator. FIG. 8D illustrates the lack of a protective effect seen when rats were treated topically with WR-1065 or amifostine in a carrier vehicle prior to irradiation of a defined rectangular field on the animal's back for 5.5 min in a Cs 137 irradiator. FIG. 8E illustrates the relationship between the number of amine groups present in a chemoprotective polyamine, chemoprotective amino thiol or cysteamine and the whole-body dose (ip administration) that is lethal to 10% of the treated animals.

FIG. 9 represents exemplary aminothiols and some of their observed effects.

FIG. 14 presents results relating to the effects pf Pre-210 on cell cycle.

DETAILED DESCRIPTION OF ILLUSTRATIVE EMBODIMENTS

Figure 1B:
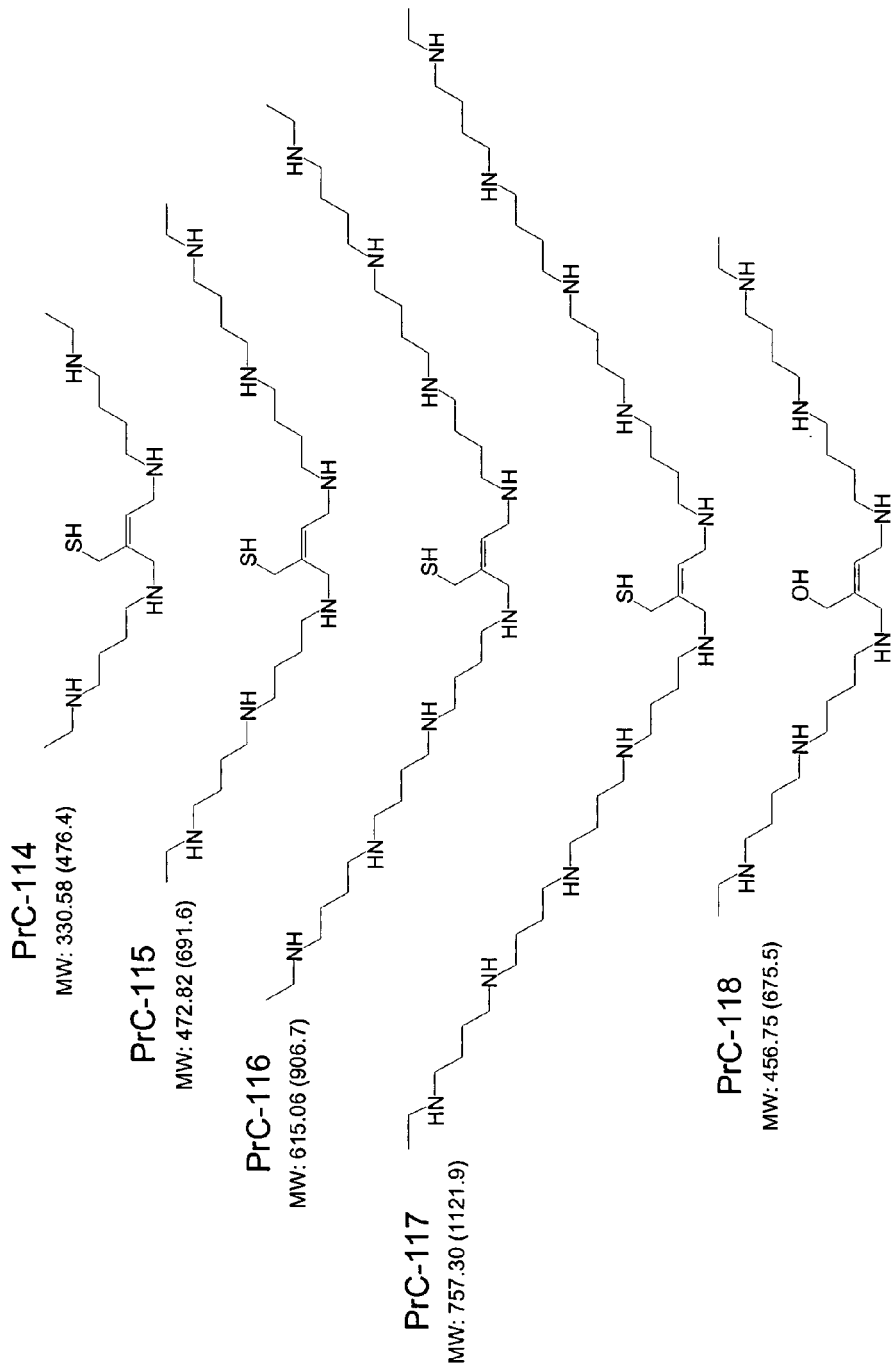

The present invention provides compounds for use in pharmaceutical preparations and methods for protecting non-cancerous, rapidly dividing cells in a patient's body from the toxic effects of chemotherapeutic agents or radiotherapy administered to the patient. In particular, the compositions and methods of the invention are designed for protecting epithelial cells. Most particularly, the targets are epithelial cells lining hair follicles and epithelial and/or mucosal cells of the skin, mouth, gastrointestinal (GI) and urogenital tract. In one embodiment, the compositions are used to reduce or prevent alopecia during cancer therapy, by topically applying the composition to the scalp. Another embodiment comprises reduction or prevention of gastrointestinal distress due to cancer therapy by administering the compositions orally. Another embodiment involves reducing or preventing mucositis from chemotherapy or radiotherapy by administering the compositions topically to the appropriate region of the body. In yet another embodiment, the compositions are used to prevent radiation-induced dermatitis, skin rash, and ulceration at the site of irradiation by applying them to the skin.

The chemotherapeutic agents from which protection of normal cells is desired may be one or a combination of agents used for such purpose, such as alkylating agents, antimetabolite inhibitors of DNA synthesis, antitumor antibiotics, mitotic spindle poisons, vinca alkaloids, and topisomerase inhibitors. Specific chemotherapeutic agents include, but are not limited to, altretamine, asparaginase, bleomycin, busulfan, carboplatin, cisplatin, carmustine, chlorambucil, cladribine, cyclophosphamide (cytoxan), cytarabine, dacarbazine, dactinomycin, daunorubicin, doxorubicin, etoposide, floxuridine, fludarabine phosphate, fluorouracil, hydroxyurea, idarubicin, ifosfamide, lomustine, mechlorethamine, nitrogen mustard, melphalan, mercaptopurine, methotrexate, mitomycin, mitoxantrone, paclitaxel, pentostatin, pliamycin, procarbazine, streptozocin, teniposide, thioguanine, thiotepa, vinblastine and vincristine. The radiation therapy consists of all useful types of radiation used in cancer treatment, including x-rays, gamma-rays, electron beams, photons, alpha-particles and neutrons.

Commonly-owned, co-pending U.S. patent application Ser. No. 10/214,917 and International Application No. PCT/US02/25216, each filed Aug. 7, 2002, describe several types of known polyamines and polyamine analogs, referred to therein as "polyamine effector" compounds, which can be efficiently delivered to target cell populations, where they are capable of protecting those cells from the harmful side effects of chemotherapy or radiotherapy. In one of its several aspects, the present invention provides novel polyamine and amino thiol compounds specifically designed for improved efficacy in protecting normal cells from the detrimental effect of cancer chemotherapy or radiation therapy. These molecules are referred to herein collectively as "chemoprotective amines." The polyamine compounds are referred to herein as "chemoprotective polyamines" and the amino thiol compounds are referred to as "chemoprotective amino thiols."

Certain definitions that will assist in the understanding of the present invention are set forth below, while others are provided throughout the specification. With respect to the compounds of the invention, it should be noted that if any variable occurs more than one time in any constituent or in any formula, its definition in each occurrence is independent of its definition at every other occurrence. Thus, for example, if a compound of the present invention is shown to incorporate, for example, one or more of $R^1$, $R^2$, $R^3$, $R^4$, $R^5$, $R^6$, $R^7$, $R^8$, $X^1$, $X^2$, $X^3$, $X^4$, $X^5$, $X^6$, $X^7$, $B^1$, $B^2$, Q, Y, or D, then the $R^1$, $R^2$, $R^3$, $R^4$, $R^5$, $R^6$, $R^7$, $R^8$, $X^1$, $X^2$, $X^3$, $X^4$, $X^5$, $X^6$, $X^7$, $B^1$, $B^2$, Q, Y, or D at each occurrence is selected independently. Combinations of $R^1$, $R^2$, $R^3$, $R^4$, $R^5$, $R^6$, $R^7$, $R^8$, $X^1$, $X^2$, $X^3$, $X^4$, $X^5$, $X^6$, $X^7$, $B^1$, $B^2$, Q, Y, or D are permissible only if such combinations result in stable compounds.

As used herein, "alkylene" refers to a bivalent alkyl radical having the general formula —$(CH_2)_n$—, where n is 1 to about 8. Non-limiting examples include methylene, ethylene, trimethylene, butylene, pentamethylene, and hexamethylene. Alkylene groups may be branched or unbranched. Alkylene groups may also contain one or more double or triple bonds within the backbone of the —$(CH_2)_n$— moiety, provided that the resultant compound is stable. Non-limiting examples include —$CH_2$—C≡C—$CH_2$— and $CH_2$—CH=CH—$CH_2$—. Alkylene groups can be substituted or unsubstituted, provided that the resultant compound is stable and so long as the substituent does not substantially interfere with present compound's intended mode of action. In certain circumstances, alkylene is preferably $C_{3-8}$ alkylene, while in other circumstances, even within the same molecule, alkylene is preferably $C_{1-6}$ alkylene.

As used herein, "alkyl" refers to a saturated straight or branched hydrocarbon having from about 1 to about 20 carbon atoms (and all combinations and subcombinations of ranges and specific numbers of carbon atoms therein), with from about 1 to about 8 carbon atoms, herein referred to as "lower alkyl", being preferred. Alkyl groups include, but are not limited to, methyl, ethyl, n-propyl, isopropyl, n-butyl, isobutyl, t-butyl, n-pentyl, isopentyl, neopentyl, n-hexyl, isohexyl, 3-methylpentyl, 2,2-dimethylbutyl, and 2,3-dimethylbutyl, octyl, decyl, dodecyl, octadecanyl, and eicosanyl.

As used herein, "pharmaceutically-acceptable salts" refers to derivatives of the disclosed compounds wherein the parent compound is modified by making acid or base salts thereof. Examples of pharmaceutically-acceptable salts include, but are not limited to, mineral or organic acid salts of basic residues such as amines; alkali or organic salts of acidic residues such as carboxylic acids; and the like. Thus, the term "acid addition salt" refers to the corresponding salt derivative of a parent compound that has been prepared by the addition of an acid. The pharmaceutically-acceptable salts include the conventional salts or the quaternary ammonium salts of the parent compound formed, for example, from inorganic or organic acids. For example, such conventional salts include, but are not limited to, those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like. Certain acidic or basic compounds of the present invention may exist as zwitterions. All forms of the compounds, including free acid, free base, and zwitterions, are contemplated to be within the scope of the present invention.

Compounds described herein throughout, can be used or prepared in alternate forms. For example, many amino-containing compounds can be used or prepared as an acid addition salt. Often such salts improve isolation and handling properties of the compound. For example, depending on the reagents, reaction conditions and the like, compounds as described herein can be used or prepared, for example, as their hydrochloride or tosylate salts. Isomorphic crystalline forms, all chiral and racemic forms, N-oxide, hydrates, solvates, and acid salt hydrates, are also contemplated to be within the scope of the present invention.

"Prodrug" refers to compounds specifically designed to maximize the amount of active species that reaches the desired site of reaction which are of themselves typically inactive or minimally active for the activity desired, but through biotransformation are converted into biologically active metabolites.

"Stereoisomers" refer to compounds that have identical chemical constitution, but differ as regards the arrangement of the atoms or groups in space.

Polyamines are small aliphatic amines found in all living cells. By nature, polyamines within cells are polycationic (i.e., capable of sustaining or neutralizing one or more equivalents of acid). They are biosynthesized from amino acids, such as arginine and ornithine. Examples of common polyamines found in plant and animal cells are: putrescine ($NH_2(CH_2)_3NH_2$), formed by the decarboxylation of ornithine or arginine; spermidine ($NH_2(CH_2)_3NH(CH_2)_4NH_2$); and spermine ($NH_2(CH_2)_3NH(CH_2)_4NH(CH2)_3NH_2$); the latter two being formed by subsequent addition of an aminopropyl moiety to putrescine and spermidine, respectively. Because such polyamines are found in nature, they may be referred to as "naturally-occurring" polyamines. However, they may be prepared by a variety of synthetic strategies, as would be known in the chemical arts.

The term "polyamine analogs" as used herein refers to polycationic molecules that are similar, but not identical to polyamines found in nature. Polyamine analogs may be branched or unbranched, or may have other structural variations as compared to naturally-occurring polyamines, while retaining the central features of polyamines (multiple amine groups, polycationic within cells). Polyamine analogs may be further categorized into three groups: (1) simple polyamine analogs, (2) constrained or conformationally restricted polyamine analogs, and (3) linked or long-chain polyamine analogs.

A "simple polyamine analog" retains the flexibility conferred by the aliphatic carbon backbone, as well as the approximate carbon chain length of naturally-occurring polyamines, but possess a modification or contain one or more added functional groups (e.g., sulfhydryl, phenyl, alkyl) that confers a desired feature or advantage to the molecule.

By comparison, "conformationally restricted polyamine analogs" (sometimes referred to herein as "constrained polyamine analogs" are modified in their carbon backbone to remove flexibility in the modified area, such that two or more amino functionalities in the molecule are restricted to a particular spatial location. Such modification often is accomplished by introducing a cyclic or unsaturated moiety at one or more locations in the carbon backbone, as described in greater detail herein.

"Linked or long-chain polyamine analogs" are polyamines that are longer than naturally-occurring polyamines such as spermine. Increasing the overall length of a polyamine may be accomplished, for example, by linking together oligoamines or by adding oligoamine "units" (such as aminopropyl or aminobutyl groups) to a foundation molecule, such as spermine. Thus, while spermine has a 3-4-3 carbon backbone (4 carbons between the two internal amino groups and 3 carbons between each internal amino group and the respective terminal amino groups), linked or long-chain analogs might comprise an additional one, two, three, four or more aminopropyl or aminobutyl groups, for example, on either or both ends of the molecule, and further may comprise terminal methyl or ethyl groups on either or both ends.

"Amino thiols" include those molecules that contain at least one amine group as well as at least one thiol group within the same molecule. Compared to a polyamine, they generally have a shorter overall chain length, and generally have a lower ratio of carbon to sulfur. Amino thiols may contain one or more other functional groups as described herein, in addition to the amino and thiol groups.

As used herein, the term "antiproliferative" refers to an agent that slows or stops cell division. The antiproliferative agent may exert its effect by inhibiting cell cycle progression at one or more stages. Such an agent may be referred to herein as a "cell cycle progression inhibitor." The chemoprotective polyamines of the invention can act as antiproliferatives, specifically cell cycle progression inhibitors, by associating with and modifying the conformation or structure of DNA. These agents are sometimes referred to as "DNA modifiers."

The design of the chemoprotective polyamines and amino thiols of the present invention emerges from the inventors' appreciation of the advantages associated with blending certain important chemical properties within a single multifunctional molecule, 1) molecular structure necessary for efficient binding to DNA and, in some instances, modification of the conformation or structure of DNA; 2) nucleophilic reactivity, to trap electrophilic chemicals that can challenge the integrity of helical DNA; and/or 3) free radical-scavenging activity to reduce or eliminate free radicals often generated by irradiation or various chemotherapeutic agents (e.g., certain reactive oxygen species).

A. Chemoprotective Polyamines

In regard to structure, the ability of a polyamine to physically align closely, or "dock" with DNA should be maintained. Mimicking the general linear nature of the known natural polyamines enables the chemoprotective polyamines of the invention to maintain DNA binding ability. Another important feature common to natural polyamines is the presence of multiple secondary amine nitrogen atoms throughout the backbone. These atoms are known to be protonated, and thus positively charged, at physiologic pH. Accordingly, maintaining secondary amine functionality throughout a chemoprotective polyamine further provides sufficient active binding sites.

Nucleophilic and/or free radical-scavenging activity was designed into the chemoprotective polyamines with the aim of maintaining all of the above mentioned structural and binding features. In various exemplary embodiments described herein, electron-rich groups, bearing sp3-hybridized nitrogen, sulfur or oxygen atoms, were positioned strategically within the polyamine backbone so that overall linearity and secondary amine character would be preserved for efficient DNA binding. The enhanced reactivity of allylic functional groups, compared to their alkyl counterparts, was also considered in designing placement of functional groups in certain embodiments. In some embodiments, chemoprotective polyamines with an olefinic core have the nucleophiles/scavengers positioned on allylic positions specifically to enhance the reactivity of those functional groups. In these embodiments, the core segment bearing the functional group was restricted in size, consistent with natural polyamine features, and provides a suitable platform from which the nucleophile or other functional group is displayed. This design feature allows one side, or face, of the 3-dimensional polyamine structure to interact with DNA while the other face, bearing the reactive functional group, is projected away from the DNA, sterically unencumbered, thus free to react with toxic electrophilic chemicals or free radicals present in the cellular matrix.

The chemoprotective polyamines of the present invention are represented by the general structure of Formula I:

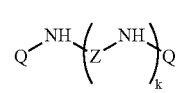

In Formula I, "Z" is either "A" or "$R^1$," provided that one "Z" is "A." "A" represents a "core" segment and the $R^1$ and Q groups typically represent alkylene ($R^1$) or alkyl (Q) chains of varying length (branched or unbranched), which, together with the amine groups as shown, make up the linked oligoamine segments that form the polyamines of the present invention.

The core segment ("A") functions in two ways: (1) it presents a platform for display of a protective functional group, namely a nucleophile or a free radical scavenger; and (2) it may be designed to introduce a conformational constraint to the polyamine (e.g., a double bond or a cyclic structure). The linked oligoamine segments (sometimes referred to as "arms" or as "polyamine side chains") function to enable the molecule to "dock" with DNA, as do naturally occurring polyamines. In one embodiment, a compound of the invention comprises one core and an "arm" of varying length on either side of the core. In another embodiment, the core may have a single arm (i.e., the core group is at one end or the other of the polyamine molecule). In another embodiment, the chemoprotective polyamine comprises two or more cores (which may be the same or different), which can be side-by-side or separated by an oligoamine segment of varying length.

The core segment provides the molecule with conformational restraint and/or a protective functional group that is attached ("tethered") to the molecule in such a way as to be optimally available for interaction with electrophilic groups, free radical groups and other reactive species present on or generated by chemotherapeutic agents or radiation. In the present invention, conformation restraint is typically introduced through the use of a double bond between two carbons. As would be appreciated by those of skill in the art, other means of introducing conformational restraint include triple bonds and ring structures, such as three-, four-, five- and six-carbon or more substituted or unsubstituted rings (in the latter embodiments, with the proviso that the ring does not introduce bulk or steric hindrance that reduces the ability of the functional group to access its targets).

The protective functional groups displayed on the core are designed to act as nucleophiles or as free radical scavengers/ antioxidants, with the understanding that certain functional groups may carry out both functions. Functional groups that typically act as nucleophiles, but that may also act as antioxidants or free radical scavengers, include, but are not limited to, —OH, —NH$_2$, —NHR, NR$_2$, —SH and —SR (wherein R is methyl or a lower alkyl which itself may be substituted with —OH, —NH$_2$, —NHR, NR$_2$, —SH or —SR).

The total length or size of a chemoprotective polyamine of the invention is generally described herein by the number of oligoamine segments (R$^1$—NH—) that make up the molecule. Typically the compounds comprise two or more such segments, and may comprise 3, 4, 5, 6, 7, 8, 9, 10, 11, 12, 13, 14, 15, 16 or even more such segments. The overall upper limit to length of the compounds is typically selected on the basis of practical considerations such as cost and ease of synthesis, solubility and/or skin or mucosal permeability, as measured against efficacy of the compound in exerting its protective effect within the cell. In specific embodiments, the chemoprotective polyamine comprises 2, 3, 4, 5, 6, 7 or 8 oligoamine segments.

Synthesis of Chemoprotective Polyamines Comprising Nucleophilic Cores

The synthetic approaches illustrated below demonstrate versatility regarding the choice of nucleophile incorporated into the core segments, the availability of both cis- and trans-isomers of the olefinic core and variability in the amine side chain segment length as well as number of segments desired. Several reaction schemes and tables are presented throughout the sections below, with both reaction intermediates and final products being assigned unique descriptive numbers. Specific descriptions of the synthesis of the key molecules are set forth in Example 1.

1. Amine Side Chains

In exemplary embodiments of the invention, amine side chains were synthesized using the reaction sequences in Scheme 1. Primary alkyl amine 1 was converted to mesitylene sulfonamide 2, which was alkylated to provide N-phthaloyl protected 3. It should be noted that the segment length can be adjusted from two carbons to six carbons in this sequence of steps, and this invention is not limited to the four-carbon chain length of molecule 3. Deprotection of the terminal nitrogen gave 4, which was readily converted to 5. The bis-sulfonamide 5 represents the shortest amine side chain with regard to number of segments. Molecule 5 also was used for chain elongation by adding segments. The three reaction steps that convert 2 to 5 were repeated and therefore represent an iterative process by which 5 was converted to 8, 8 elaborated to 11 and 11 to 14. Each of the mesitylene-sulfonyl protected amine side chains 5, 8, 11, 14, and related chain-extended derivatives, are suitable for attachment to a core segment. In sum, Scheme 1 describes how a single polyamine side chain may be produced. This process can be repeated to add additional polyamine side chain segments.

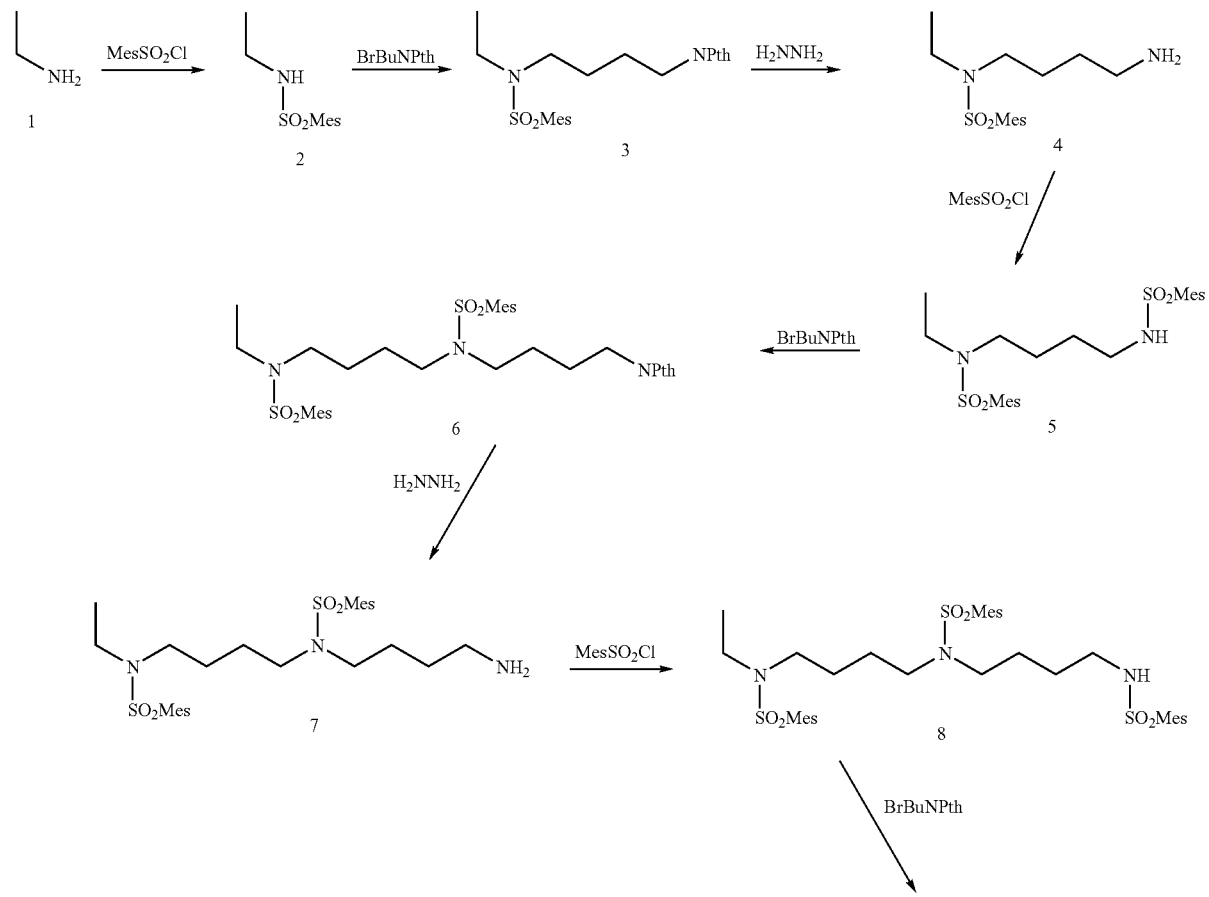

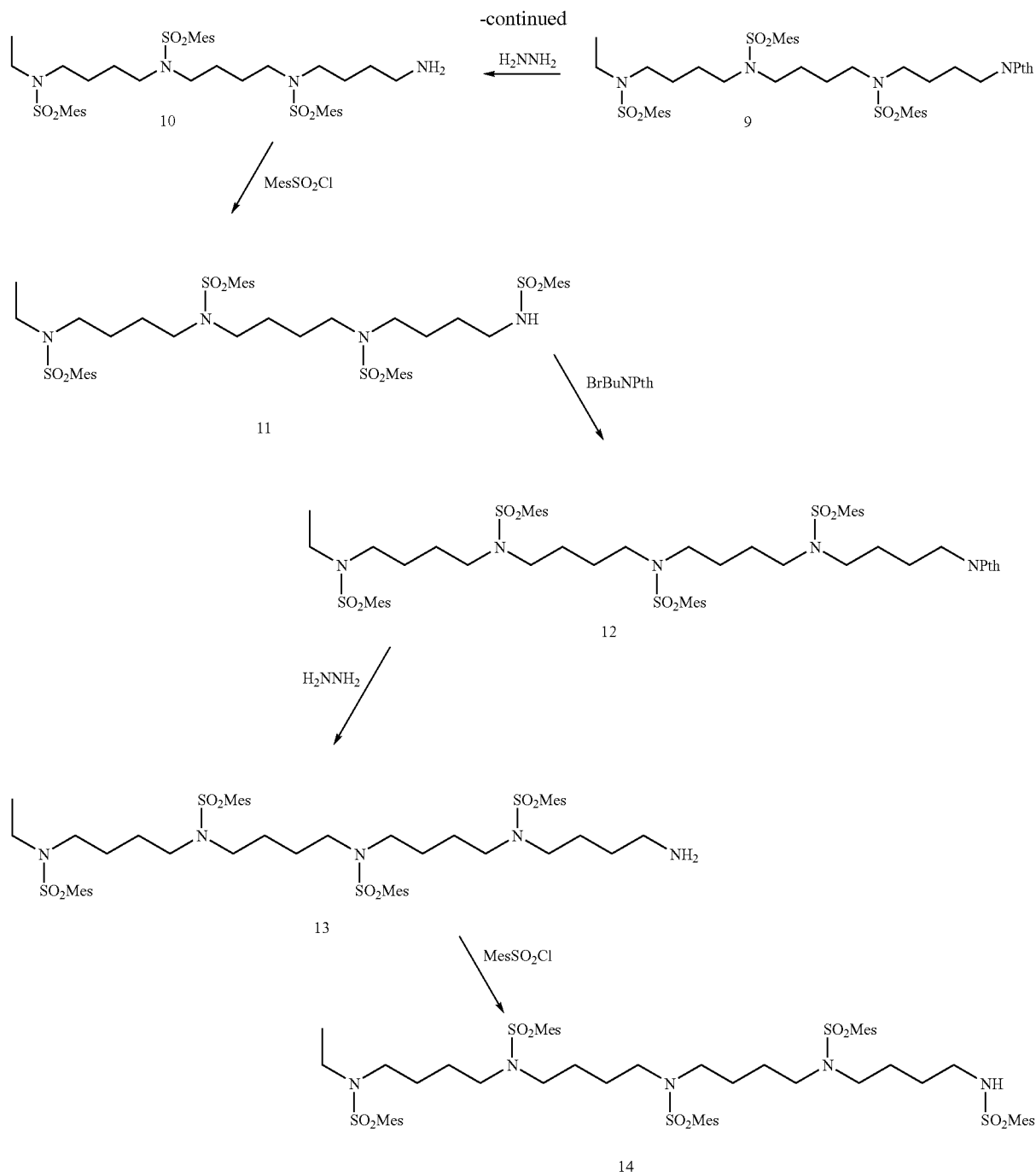

2. Synthesis of Olefinic Core and Side Chain Attachment

A general description of the olefinic core synthesis is illustrated in Scheme 2. Dihydroxyacetone dimer 15 was converted to ketone 16. Olefination of 16 provided ester 17, which was carefully reduced to the allylic alcohol 18 while maintaining the integrity of the silyl groups. Mesylation gave allylic mesylate 19, which was coupled to an amine side chain to provide 20, where A represents the mesitylenesulfonyl protected amine side chain. Acid treatment of 20 gave diol 21, which was monobenzoylated to provide 22. It should be noted that the cis- and trans-isomers of alcohol 22 can be separated by chromatography to provide the individual purified isomers. Alcohol 22 was then transformed to the allylic bromide 23, which was coupled to a second protected amine side chain to produce 24. For the purpose of this invention it should be noted that in 24, protected amine side chains A and A' can be identical, but can also vary in segment length as well as overall chain length. Hydrolysis of 24 gave mesitylenesulfonyl protected polyamine 25. Protected polyamine 25 can be deprotected (see polyamine 27 in Scheme 3), or serve as a versatile intermediate that can be further elaborated at the allylic alcohol position to insert alternative protective functional groups.

Scheme 2

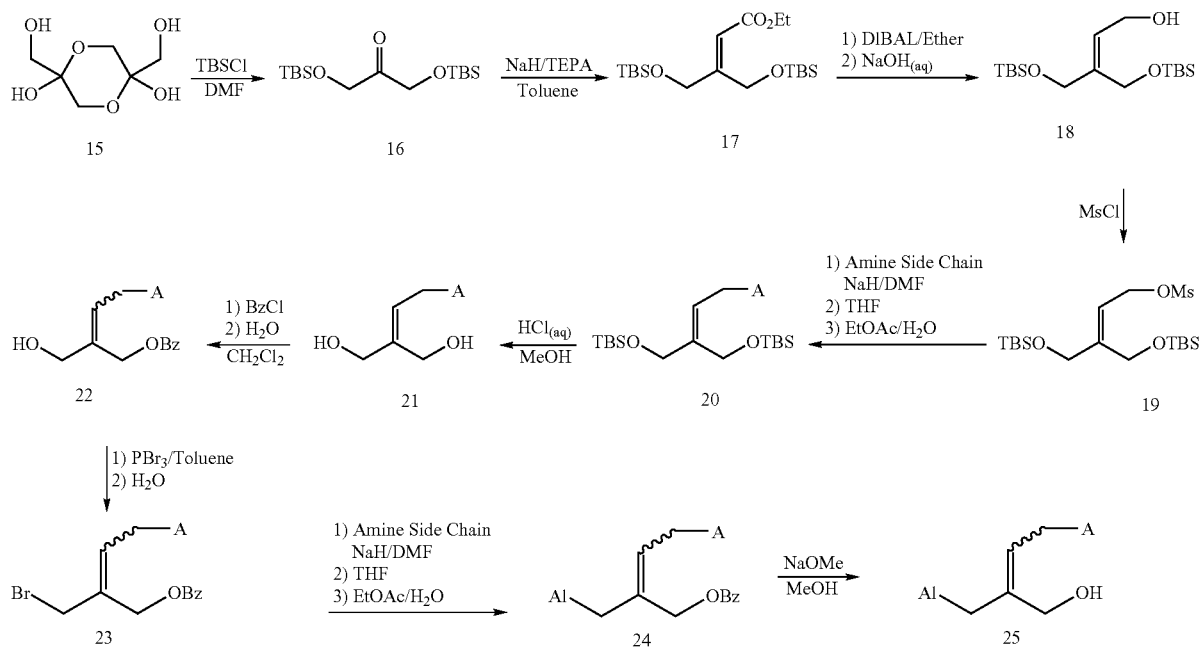

where A or A' are SO₂Mes protected polyamine side chains described in scheme 1.
where R or R' are the free polyamine side chains with the protecting groups removed.

3. Functional Groups on the Chemoprotective Polyamine Core

A method for introducing various protective functional groups onto a core segment is shown in Scheme 3. Alcohol 26 was converted to mesylate 27, which was subsequently reacted with various species having suitable nucleophilic character, to provide, for example, 29, 31, 33 or 35. Subsequent deprotection produced, for example, the chemoprotective polyamines 30, 32, 34 and 36.

Scheme 3

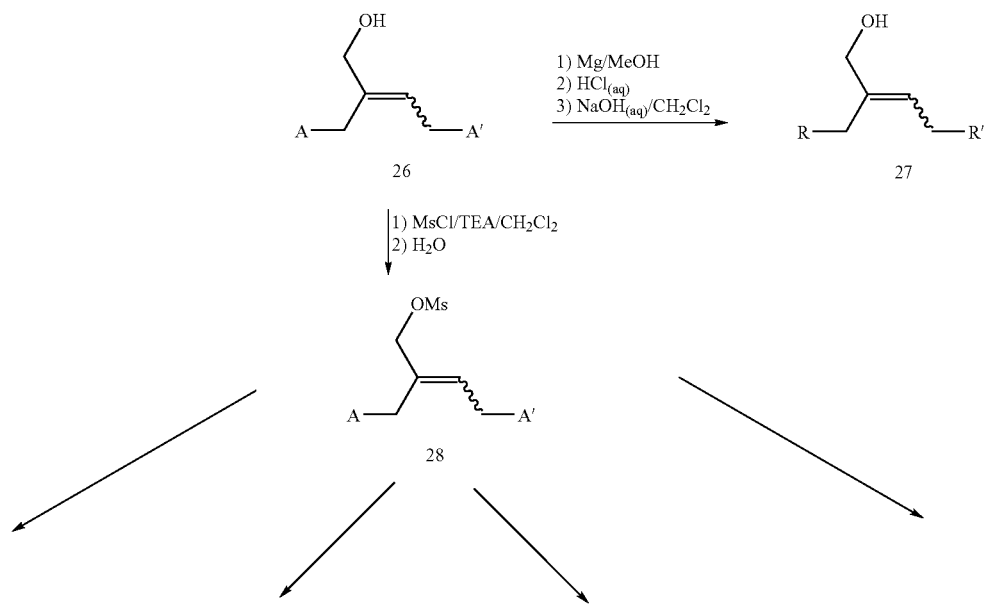

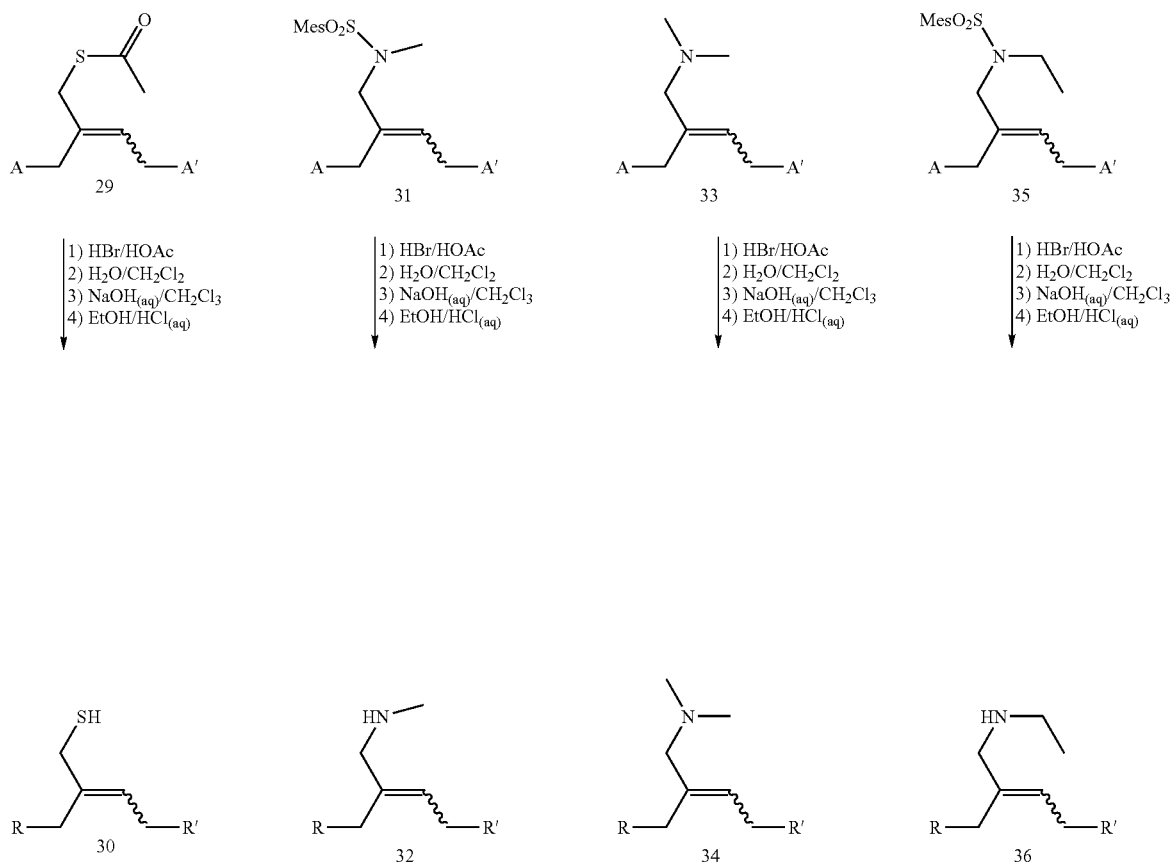
where A or A' are SO₂Mes protected polyamine side chains described in scheme 1.
where R or R' are the free polyamine side chains with the protecting groups removed
4. Functional Groups Displayed from an Aliphatic Core
A synthetic approach to chemoprotective polyamines bearing functional groups on an aliphatic core segment is shown in Scheme 4.
Scheme 4
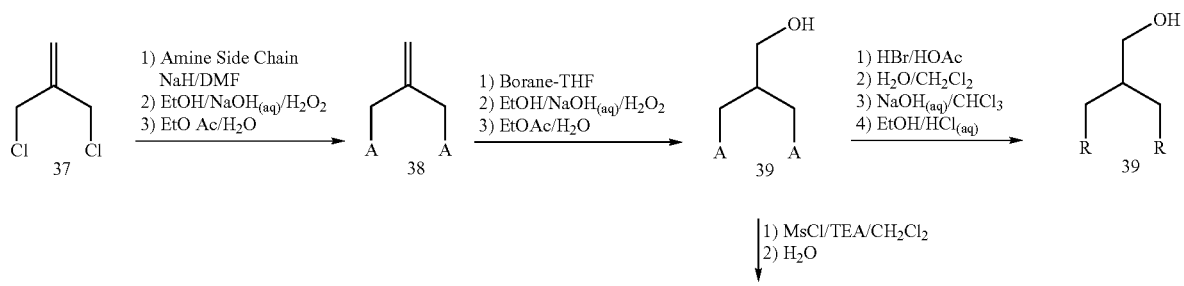

-continued

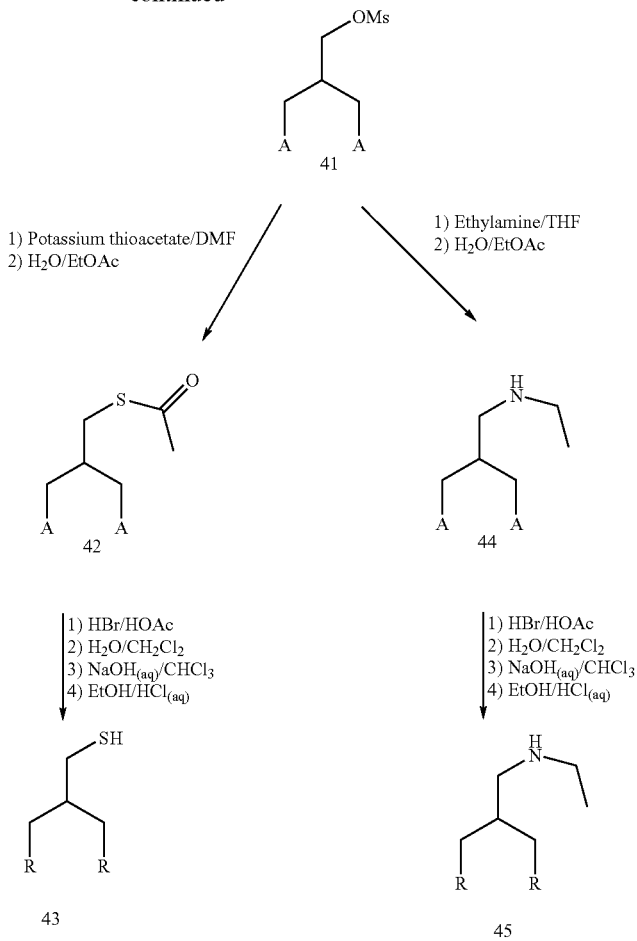

where A or A' are SO₂Mes protected polyamine side chains described in scheme 1.
where R or R' are the free polyamine side chains with the protecting groups removed.

Figure 1C:
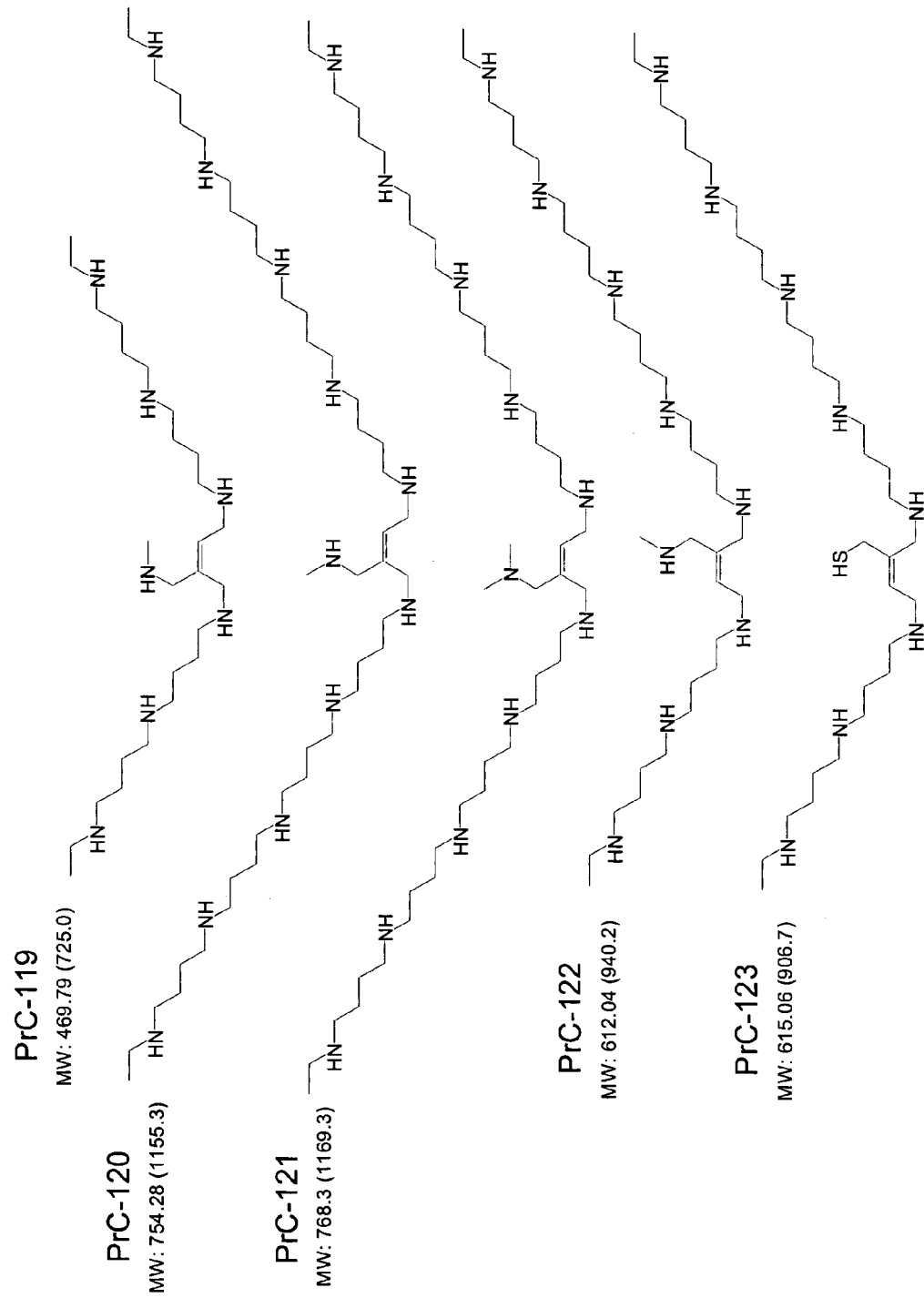
Figure 1D:
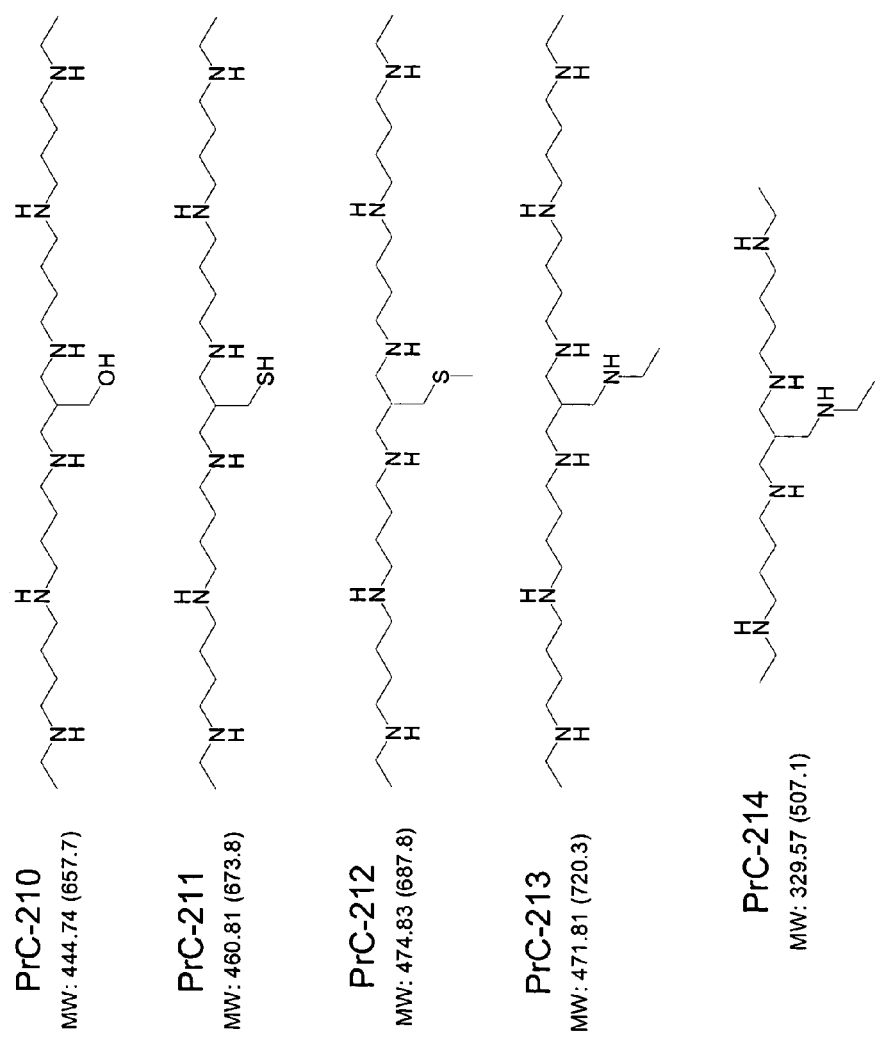

In some pharmacologic settings, there may be advantage in displaying a protective functional group from a flexible aliphatic core as has been done in molecules PrC-210, PrC-211, as well as the rest of the molecules shown in FIGS. 1D and 1E. Using chemoprotective polyamines to deliver nucleophiles/free radical scavengers to at-risk cells, while also binding DNA to enable DNA protection and growth regulation, requires optimization of each of the chemoprotective polyamine's structural parameters, including segment length, overall length, functional group, and the platform from which the functional group is displayed. For instance, displaying an alkyl-nucleophile side chain from a flexible core may change the interaction between polyamine and DNA, and with it, change the growth regulation "phenotype" that would be linked with the displayed nucleophile "phenotype" on a particular chemoprotective polyamine. This combination of functions within a given molecule may be optimized for each pharmacologic use of chemoprotective polyamines. In the reaction sequence of Scheme 4, dichloride 37 was converted to olefin 38, which was subsequently transformed to alcohol 39. Alcohol 39 can be deprotected to give 40, or converted to the mesylate intermediate 41. Mesylate 41 was then converted, with suitable nucleophiles, to 42 and 44, which upon deprotection, produce chemoprotective polyamines 43 and 45.

Other aliphatic polyamines may be prepared by hydrogenating olefinic polyamines of the invention. This is accomplished by employing hydrogenation catalysts in the presence of hydrogen or molecules that provide hydrogen during the course of a reaction, such as for example, hydrazine, cyclohexadiene, or alpha-terpinene. Further, as one ordinarily skilled in the art would recognize, one or more of the double bonds in any given olefinic polyamine may be selectively hydrogenated by selection of catalysts that preferably coordinate to one or more of the "D" moieties of the present compounds and transfer hydrogen selectively to the olefin adjacent to the "D" moiety. For a general overview, see J. March, Advanced Organic Chemistry: Reactions, Mechanisms, and Structure, Fourth Edition, John Wiley and Sons, New York (1992), pp 771-780.

5. Polyamines Containing Two or More Cores

The synthesis of a chemoprotective polyamine with more than one core unit is illustrated in Scheme 5. The core intermediate 23 (see Scheme 2) is reacted with sulfonamide 54 to give 55. Removal of the phthaloyl group provides 56, which upon sufonylation gives bis-sulfonamide 57. If the desired functional group on the core segments of the target polyamine is hydroxyl, 57 can be converted directly to silyl ether 60, where X=OH. Alternatively, the nucleophile can be modified by converting 57 to 58, followed by functional group transformation to 59. Sulfonamide 59 can likewise be converted to 60. Desilylation to 61, and subsequent benzoylation, gives 62. Conversion to the bromide 63 provides a pivitol intermediate. The chain-elongation process can be terminated by attaching an amine side chain, thus providing a polyamine bearing two core units. Alternatively, bromide 63 can be subjected to an iterative process that involves repeating the steps shown at the start of Scheme 5. This will install a third linker-core repeating unit in the polyamine chain. Manipulation of the functional group in a second or third core unit can be effected as shown in the conversion of 57 to 59.

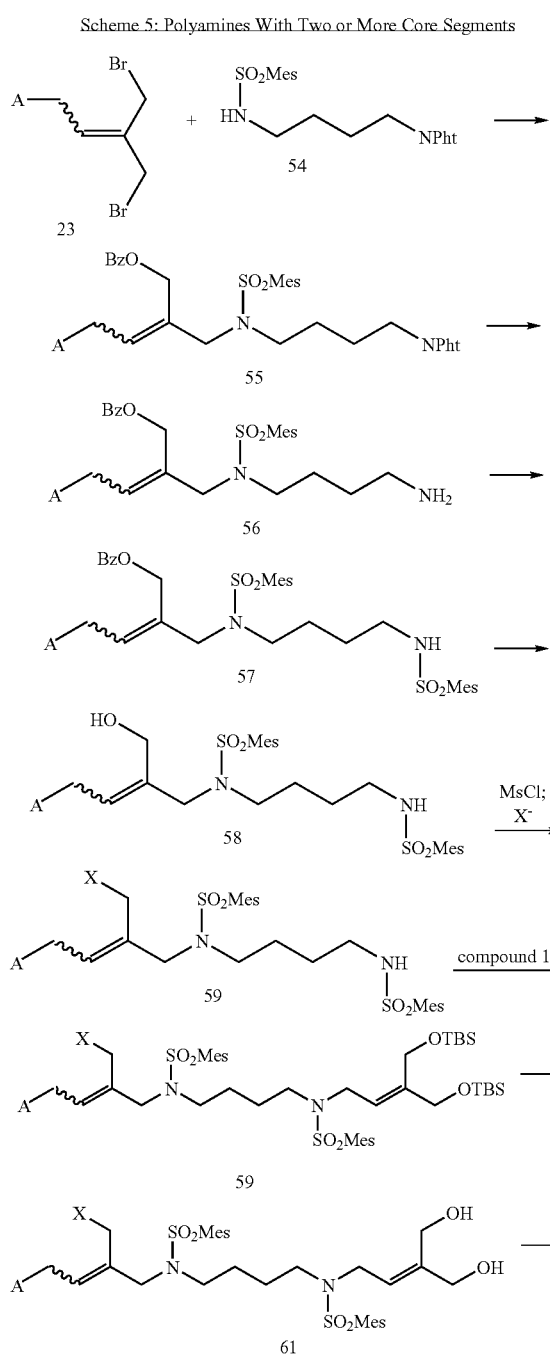

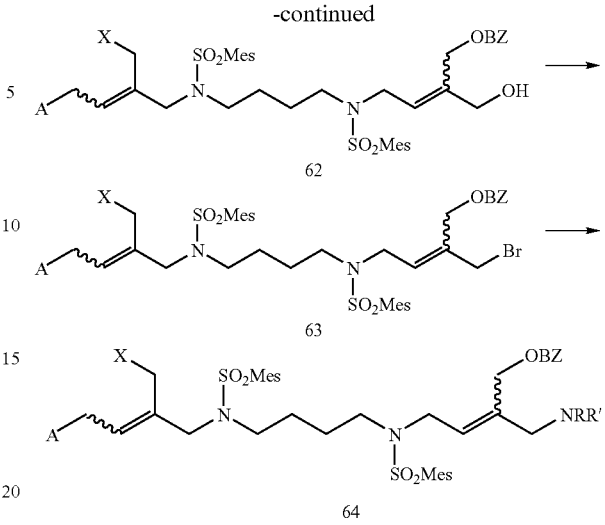

NRR' can be an amine side chain similar or, or equal to A.
NRR' can also be a repeating linker-core unit if oligomerization is desired.

B. Chemoprotective Amino Thiols

In addition to the chemoprotective polyamines described above, certain smaller amine compounds, particularly those containing thiol functional groups, have been designed for use in accordance with the present invention. Accordingly, in one embodiment, the present invention provides novel pharmaceutically active compounds of Formula II:

$$Q \smallsetminus NH \diagup A \diagdown NH \diagup Q \qquad II$$

wherein:
A is:

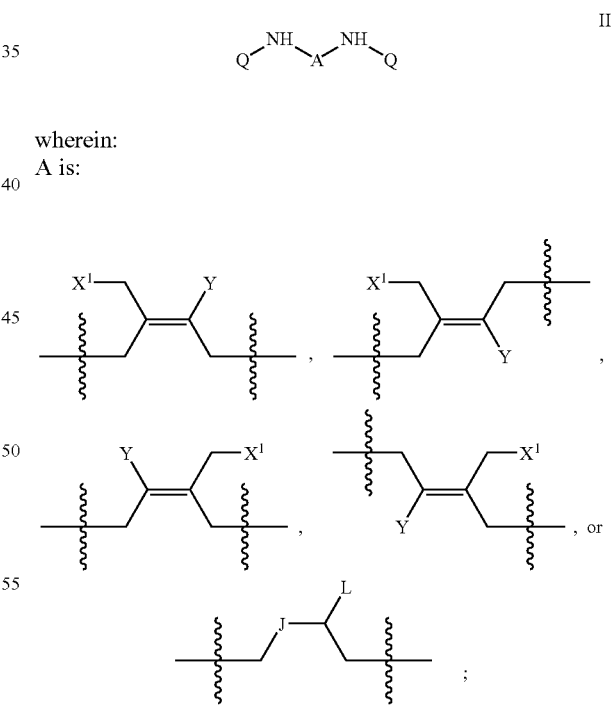

J is a single bond or —CH(Y)—;
L is —CH$_2$X$^1$, —SH, —CHX$^2$(X$^3$);
X$^1$ is —SH or —R$^1$—SH;
X$^2$ and X$^3$ are each independently H, —SH, or —R$^1$—SH, provided that at least one of X$^2$ and X$^3$ is other than H or —SH;

Y is H, alkyl, or —R²-D;
D is —OH, —SR³, or —NR³R⁴;
R³ is H or lower alkyl;
R⁴ is H, lower alkyl, or —R⁵-D;
each Q is independently H, lower alkyl, or —R⁶—SR³, provided that when L is SH, at least one of Q is other than H; and
each R¹, R², R⁵, and R⁶ is independently $C_{1-6}$ alkylene;
or a stereoisomer, prodrug, pharmaceutically-acceptable salt, or mono or polyprotonated acid salt thereof.

In some preferred embodiments of Formula II compounds, D is —SR³. More preferably, D is —SH. In other preferred embodiments of Formula II compounds, R³ is H.

In other preferred embodiments of Formula II compounds, A is:

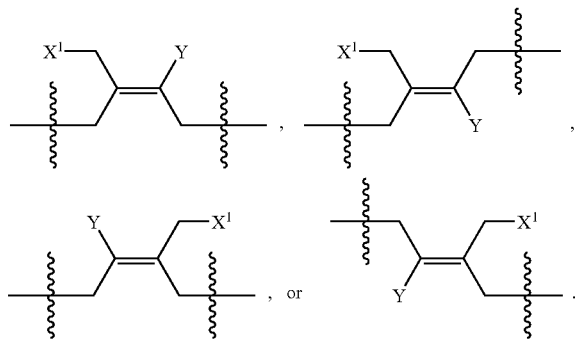

More preferably, in compounds of Formula II wherein A is as described above, Y is H or —R²-D. More preferably still, Y is H. Even more preferably, when Y is H, X¹ is —SH. Alternatively, Y is —R²-D, D is —SR³, and R³ is H. More preferably, when Y is —R²-D, D is —SR³, and R³ is H, X¹ is —SH. Yet more preferably, when Y is —R²-D, D is —SR³, and R³ is H, X¹ is SH, each Q is independently methyl or ethyl.

In other preferred embodiments of Formula II compounds, wherein A is as described above, each Q is independently H or lower alkyl. More preferably each Q is independently methyl or ethyl.

In other preferred embodiments of Formula II compounds, A is:

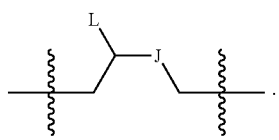

In some more preferred embodiments of Formula II compounds wherein A is as described above, L is —CH₂X¹. More preferably, when L is —CH₂X¹, X¹ is —SH. In other more preferred embodiments, when L is —CH₂X¹, X¹ is —R¹—SH. Alternatively, in other more preferred embodiments, L is —SH. In other preferred embodiments of Formula II compounds wherein A is as described above, J is —CH(Y)—. More preferably, when J is —CH(Y)—, Y is H or —R²-D. Even more preferably, Y is H. Alternatively, when Y is —R²-D, D is —SR³, and R³ is H. In some other more preferred embodiments of Formula II compounds wherein A is as described above, Q is H, methyl, or ethyl.

In other preferred embodiments of Formula II compounds wherein A is:

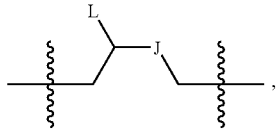

J is a single bond. In more preferred embodiments, wherein A is as described above and J is a single bond, L is —CH₂X¹ and X¹ is —SH. In other more preferred embodiments wherein L is —CH₂X¹, X¹ is —R¹—SH. In yet other more preferred embodiments, wherein A is as described above and J is a single bond, L is —SH. In other more preferred embodiments, wherein A is as described above and J is a single bond, Q is H, methyl, or ethyl. In still other more preferred embodiments, wherein A is as described above and J is a single bond, L is —CHX²(X³). In even more preferred embodiments when L is —CHX²(X³), X² and X³ are each —R¹—SH. Alternatively, when L is —CHX²(X³), X² is —SH and X³ is —R¹—SH.

In another embodiment, the present invention provides novel pharmaceutically active compounds of Formula III:

wherein:
X⁴ is —SH or —R¹—SH;
X⁵ is H, —SH or —R¹—SH, provided that at least one of X⁴ and X⁵ is other than —SH;
B¹ is —CH₂NHR⁷, —CH₂CH₂NHR⁷, —CH₂CH₂CH₂NHR⁷, or —CH(NH₂)CH₂NHR⁷; and
R⁷ is H or lower alkyl, provided that when B¹ is —CH₂NHR⁷, R⁷ is other than H;

or a stereoisomer, prodrug, pharmaceutically-acceptable salt, or mono or polyprotonated acid salt thereof.

In some preferred embodiments of Formula III compounds, X⁴ is —SH and X⁵ is —R¹—SH. More preferably, when X⁴ is —SH and X⁵ is —R¹—SH, X⁵ is —CH₂SH. In other preferred embodiments of Formula III compounds, X⁴ and X⁵ are each independently —R¹—SH. More preferably, X⁴ and X⁵ are each independently —CH₂SH or —CH₂CH₂SH. In yet other preferred embodiments of Formula III compounds, R⁷ is H or methyl. In still other preferred embodiments of Formula III compounds, B¹ is —CH₂NHR⁷, —CH₂CH₂NHR⁷, or —CH₂CH₂CH₂NHR⁷.

In another embodiment, the present invention provides novel pharmaceutically active compounds of Formula IV:

wherein:
X⁶ and X⁷ are each independently —R¹—SH;
B² is —R²—NHR⁸; and $R^8$ is H or lower alkyl, provided that when $B^2$ is —$CH_2CH_2NHR^8$, $R^8$ is other than H;

or a stereoisomer, prodrug, pharmaceutically-acceptable salt, or mono or polyprotonated acid salt thereof.

In some preferred embodiments of Formula IV compounds, wherein X and $X^7$ are each independently —$R^1$—SH, $X^6$ and $X^7$ are each independently —$CH_2SH$ or —$CH_2CH_2SH$. In other preferred embodiments wherein $B^2$ is —$R^2$—$NHR^8$, $R^8$ is H or methyl. In yet other preferred embodiments of Formula IV compounds, $B^2$ is —$CH_2NHR^8$, —$CH_2CH_2NHR^8$, or —$CH_2CH_2CH_2NHR^8$.

In another embodiment, the present invention provides novel pharmaceutically active amino thiol compounds 3-dimethylamino-butane-2-thiol, 4-amino-3-methyl-pentane-2-thiol, 2-methyl-3-methylamino-propane-1-thiol, 4-methylamino-pentane-1-thiol, 3-methylamino-butane-1-thiol, 3-(3-mercapto-propylamino)-propane-1-thiol, 3,4-diaminobutane-1,2-dithiol, or 2-amino-2-aminomethyl-propane-1,3-dithiol.

In addition to the novel chemoprotective amino thiol compounds described above, the present invention also encompasses the use of the known compound, cysteamine ($NH_2$—$CH_2$—$CH_2$—SH), as an active agent in pharmaceutical preparations and methods for protecting non-cancerous, rapidly dividing cells in a patient's body from the toxic effects of chemotherapeutic agents or radiotherapy administered to the patient.

Synthesis of Chemoprotective Amino Thiols

Schemes 6-15 below set forth schemes for synthesizing various chemoprotective amino thiol compounds of the invention.

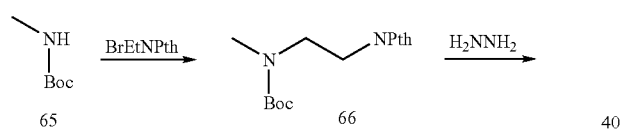

Scheme 6

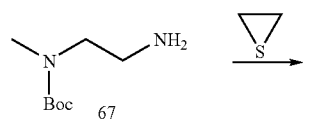

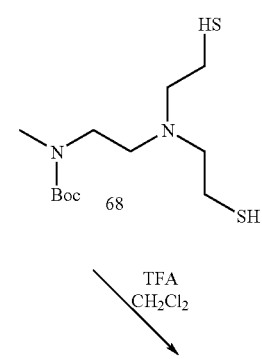

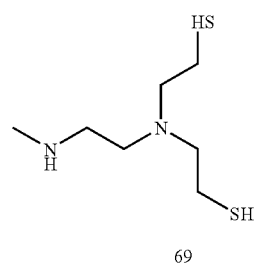

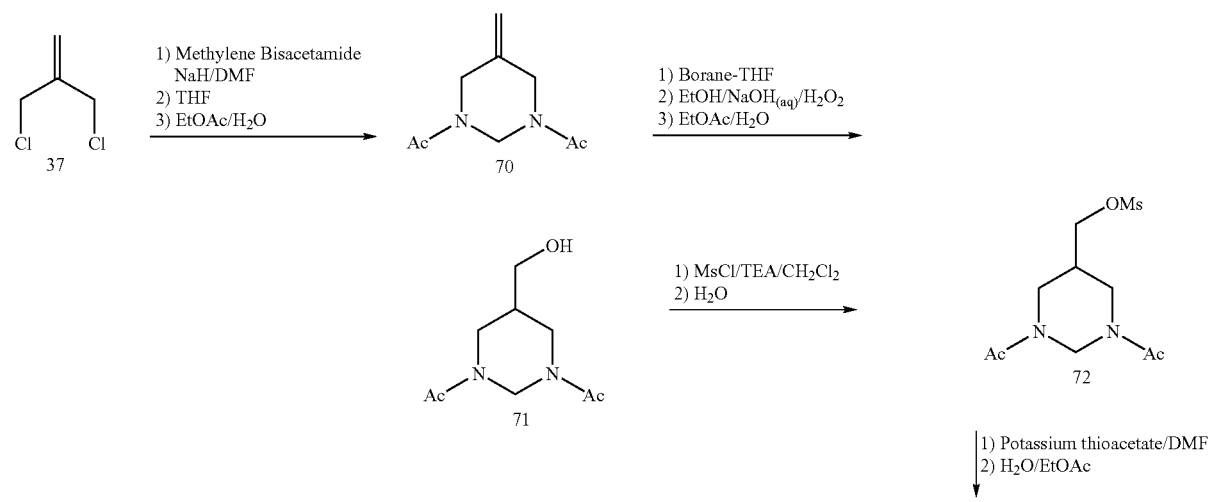

Scheme 7

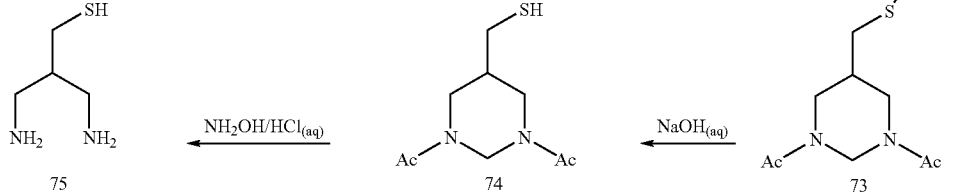
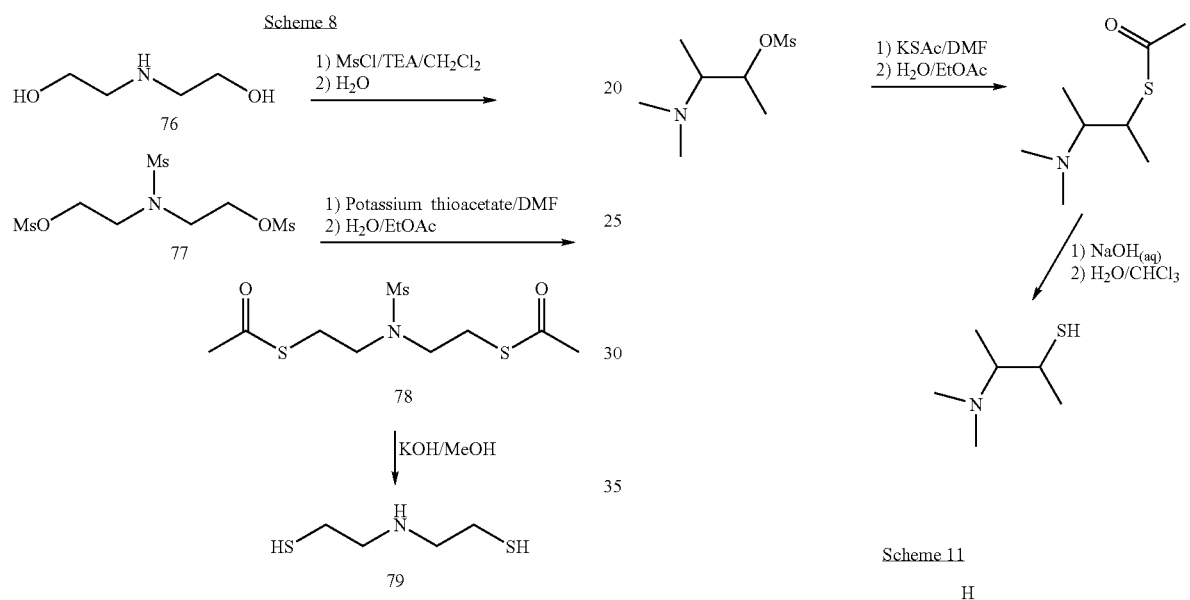
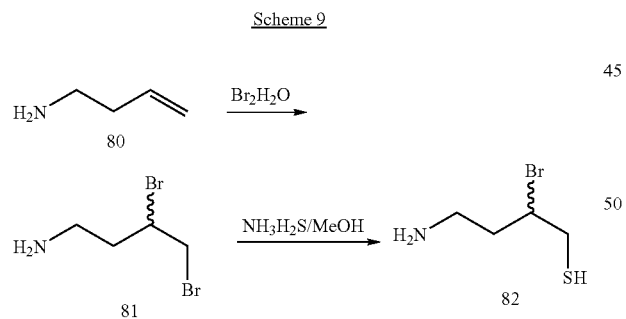
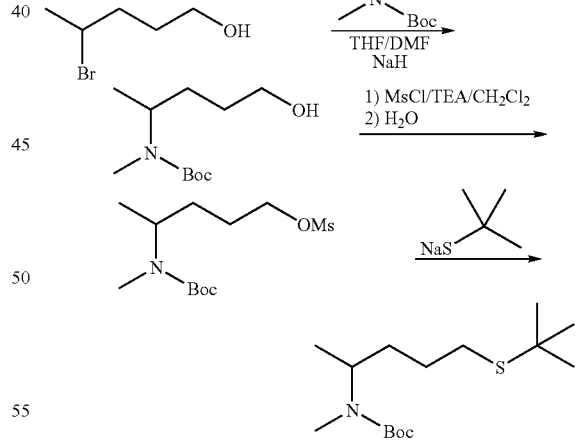
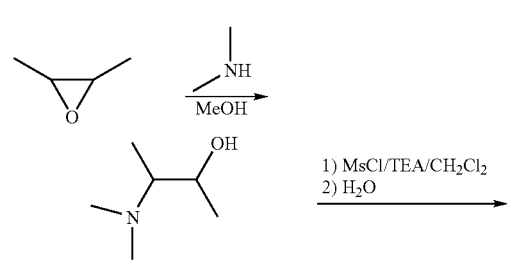
Scheme 11 methodology can be used to create 4-amino-3-methyl-pentane-2-thiol, 2-methyl-3-methylamino-propane-1-thiol, and 3-methylamino-butane-1-thiol.

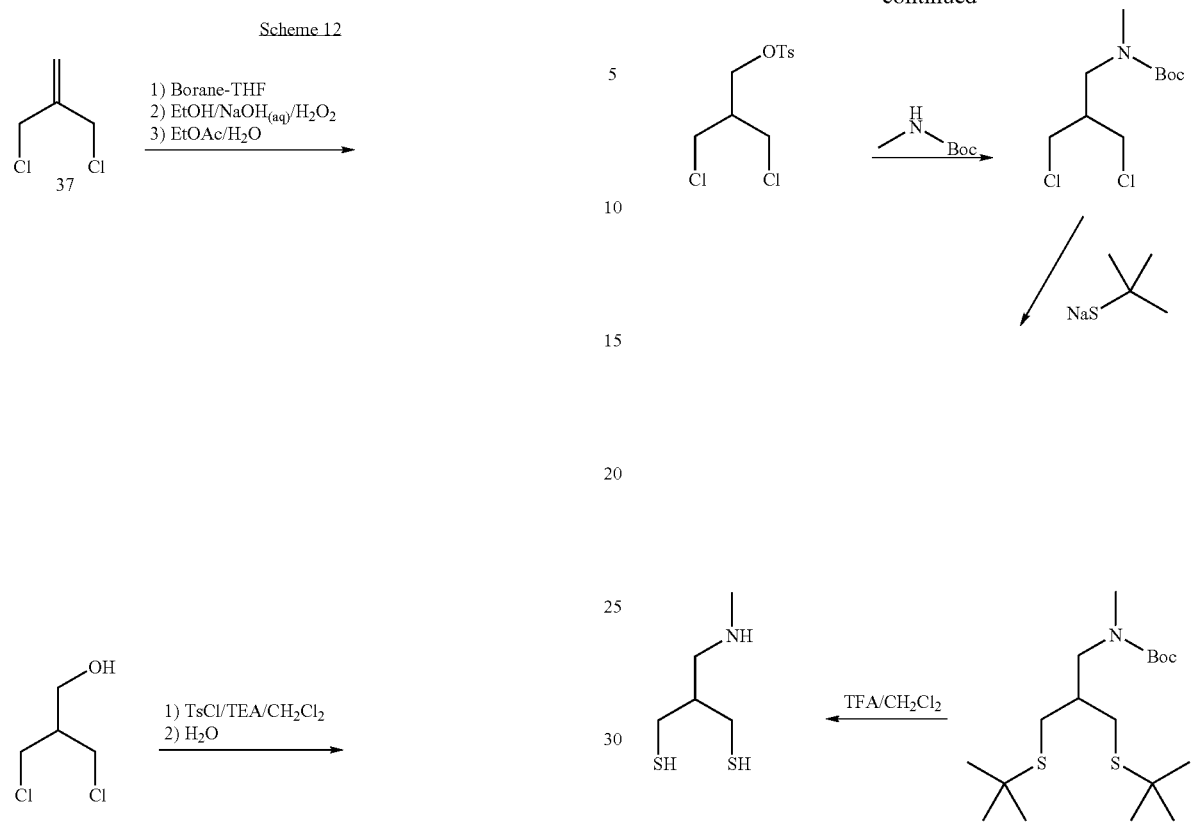
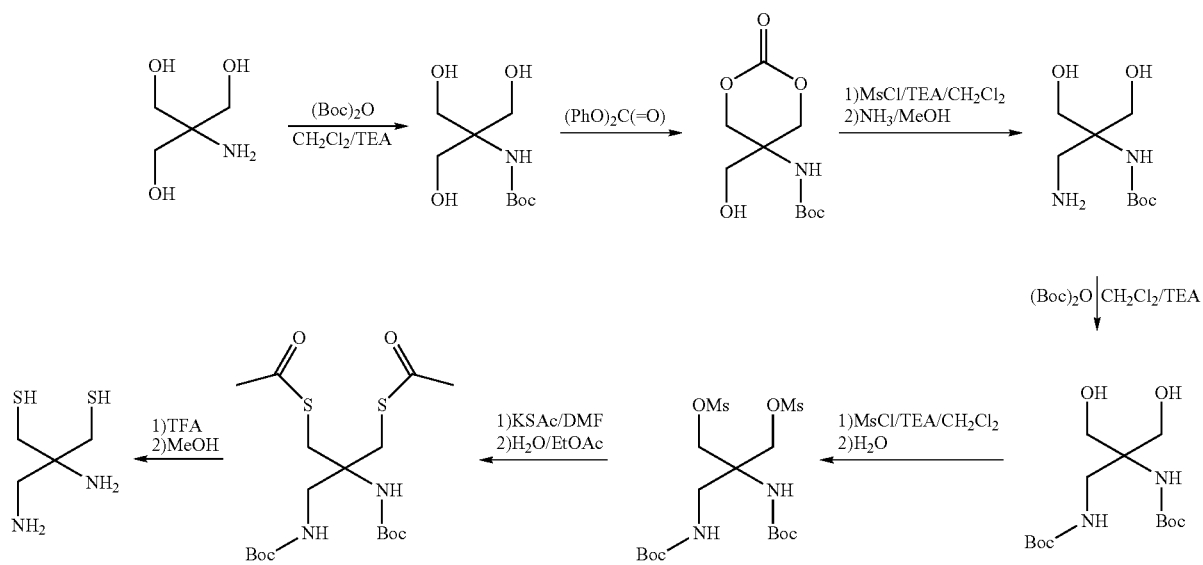

Scheme 14
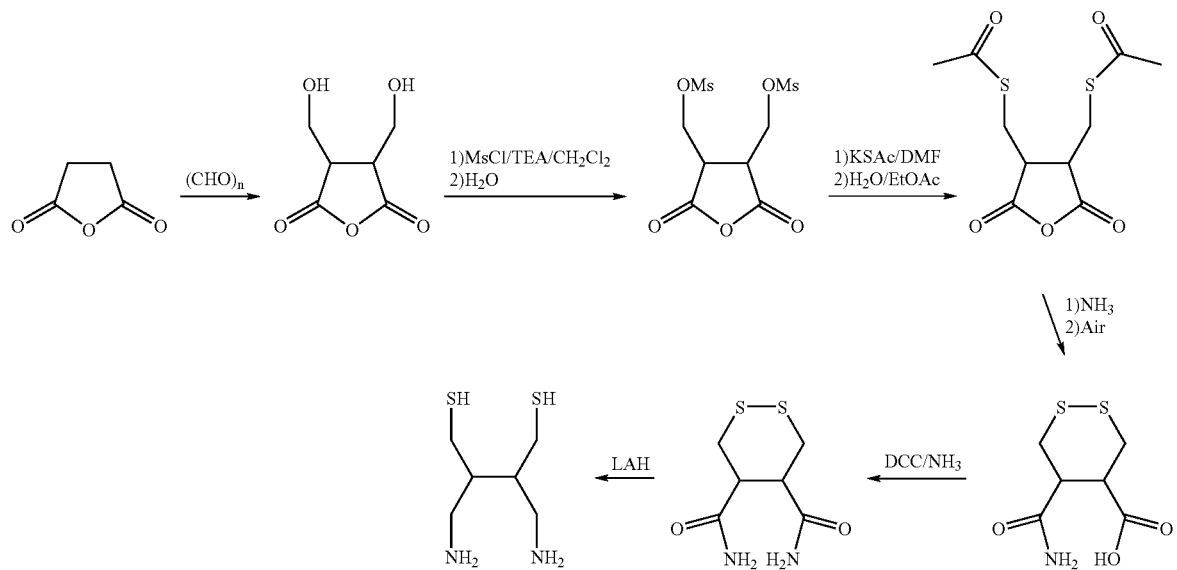
Scheme 15
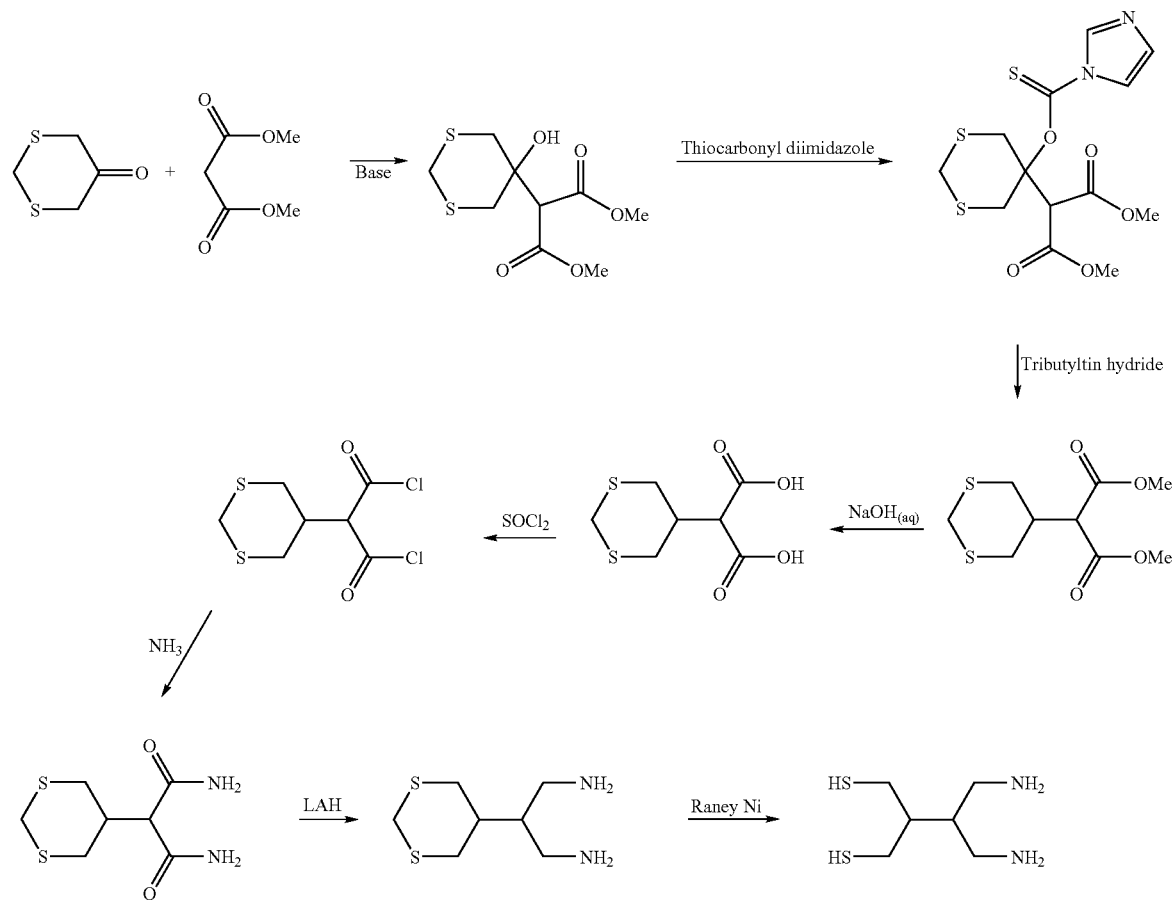
Scheme 15 methodology can be used to create 2-(2-Methylamino-1-methylaminomethyl-ethyl)-propane-1,3-dithiol.

C. Utility of Chemoprotective Polyamines and Amino Thiols in Regulating Cell Growth and Protecting Against Side Effects of Cancer Therapies To determine the activity of the described compounds as regulators of cell growth, as well as to provide mechanistic insight into ways by which these compounds regulate cell growth, we examined chemical interaction between the subject compounds and nucleic acids and assessed the extent to which these chemical and growth regulatory properties conferred protection in animal tissues against cancer chemotherapy and radiotherapy. Several exemplary compounds of the invention were tested using various in vitro and in vivo model systems. The subject compounds were found to inhibit growth of human skin cells at sub-micromolar to millimolar concentrations, in a manner that could be correlated to their chemical structure. Consistent with this inhibition of cell growth, the compounds were shown to bind avidly to helical DNA, to induce expression of the negative growth regulator, p21, and to block cells within the G1 phase of the cell cycle, also in a manner related to their structure. When the subject molecules were applied locally by topical administration to rodent skin, they protected the hair follicle cells and blocked the alopecia normally seen following systemic administration of a chemotherapy drug.

The in vitro growth inhibitory effects of certain of the chemoprotective polyamines of the invention were measured using primary, diploid fibroblasts isolated from human skin. As shown in Table 1, $IC_{50}$ concentrations (the drug concentration that caused a 50% inhibition of cell growth) for the polyamines ranged from sub-micromolar to millimolar.

TABLE 1

| Compound # [MW:HCl salt] | Expt. 1, | Expt. 2 |
|---|---|---|
| | $IC_{50}$ (uM) | |
| PrC-110 [523.9] | 1680 | 809 |
| PrC-111 [739.0] | 980 | 180 |
| PrC-112 [954.2] | 2.53 | |
| PrC-113 [1169.3] | 0.33 | 0.21 |
| PrC-114 [476.4] | 850 | 240 |
| PrC-115 [691.6] | 4100 | 1090 |
| PrC-116 [906.7] | 5.8 | |
| PrC-117 [1121.9] | 0.32 | 0.24 |
| PrC-118 [675.5] | 78 | |
| PrC-119 [725.0] | 470 | 202 |
| PrC-120 [1155.3] | 0.22 | 0.18 |
| PrC-121 [1169.3] | 0.15 | |
| PrC-122 [940.2] | 0.81 | |

Figure 2:
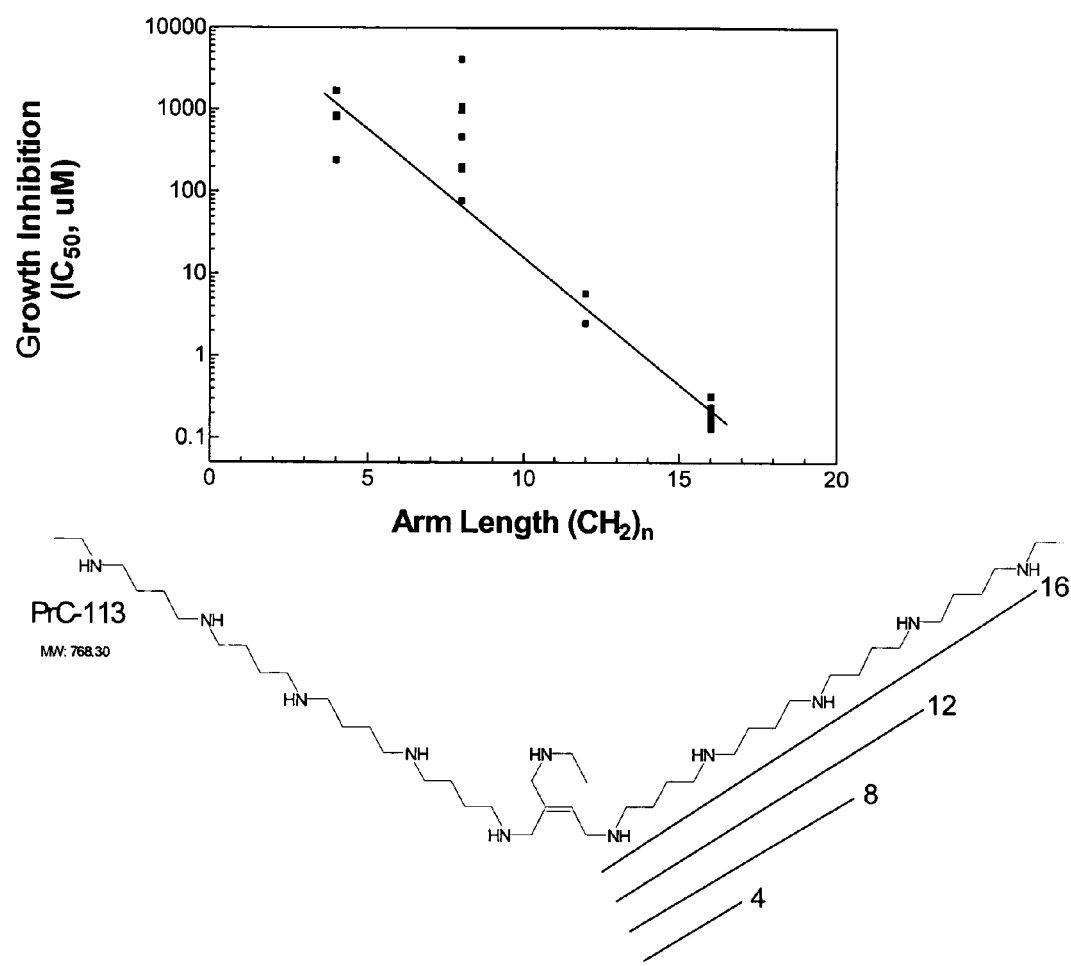
FIG. 2 illustrates the relationship between the number of aliphatic carbon atoms in each chemoprotective polyamine side chain ('arm') and the respective IC$_{50}$ dose for inhibition of human fibroblast growth.

FIG. 2 shows that the $IC_{50}$ concentration for each chemoprotective polyamine was tightly correlated with the length of the polyamine side chains ('arms') attached to a central butene core, with the long arms, i.e., those containing 16 aliphatic carbon atoms, associated with sub-micromolar $IC_{50}$ values.

The chemoprotective polyamines provided herein are also able to bind, denature and precipitate DNA from solution. As the skilled artisan will appreciate, as the concentration of polyamine is increased, there is a point where polyamine binding to helical B-DNA induces single-stranded 'bubbles' and conversion to other forms of DNA structure, such as Z-DNA (Feuerstein, B. et al., *Nuc. Acids Res.* 17:6883-6892, 1989; Basu, H. and Marton, L., *Biochem. J.* 244:243-246, 1987), as well as precipitating the DNA from solution. Table 2 shows that the four molecules that contain '16 carbon arms,' i.e., PrC-113, PrC-117, PrC-120 and PrC-121, all have $IC_{50}$ concentrations that are lower than all of the other molecules that contain shorter aliphatic arms.

TABLE 2

| Compound # [MW:HCl salt] | DNA Bind/ppt. Expt. 1, | Expt. 2 |
|---|---|---|
| | $IC_{50}$ (uM) | |
| PrC-110 [523.9] | 270 | |
| PrC-111 [739.0] | 88 | |
| PrC-112 [954.2] | 93 | |
| PrC-113 [1169.3] | 35 | |
| PrC-114 [476.4] | 94 | |
| PrC-115 [691.6] | 37, | 83 |
| PrC-116 [906.7] | 82, | 63 |
| PrC-117 [1121.9] | 58, | 57 |
| PrC-118 [675.5] | — | |
| PrC-119 [725.0] | 89 | |
| PrC-120 [1155.3] | 57 | |
| PrC-121 [1169.3] | 49 | |
| PrC-122 [940.2] | 102 | |
| PrC-123 [906.7] | 131, | 117 |
| Spermine | 2600 | |

This relationship between arm length of the chemoprotective polyamine and increased ability to disrupt and denature B-DNA structure is also a novel aspect of this aspect of the invention. The increased ability to bind DNA and disrupt its helical structure may also contribute to the molecule's ability to protect cellular DNA against electrophilic chemotherapy drug metabolites and against oxygen free radicals generated during radiotherapy. Both of these toxic modalities are believed to require normal B-DNA helical structure within the cell's nuclear DNA in order to achieve chemical or physical disruption of the cellular DNA, the first step in the apoptotic cascade.

Figure 4:
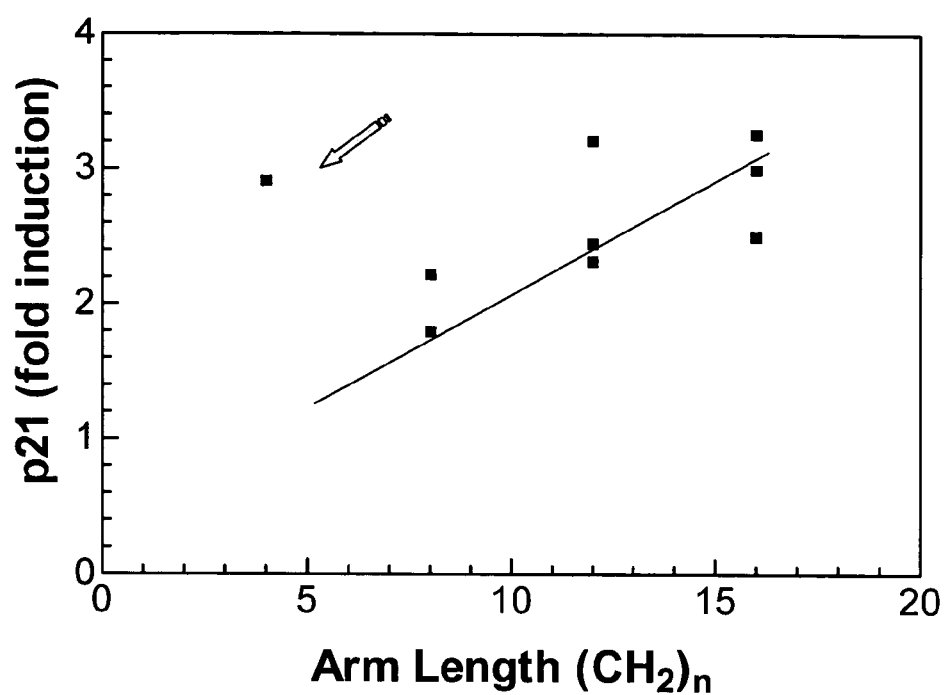
FIG. 4 illustrates the relationship between the number of aliphatic carbon atoms in each chemoprotective polyamine 'arm' and the respective induced p21 level in diploid human fibroblasts after a 30 hr exposure. The arrow points to the value for PrC-110, which also showed excellent efficacy in the in vivo alopecia test.
Figure 5A:
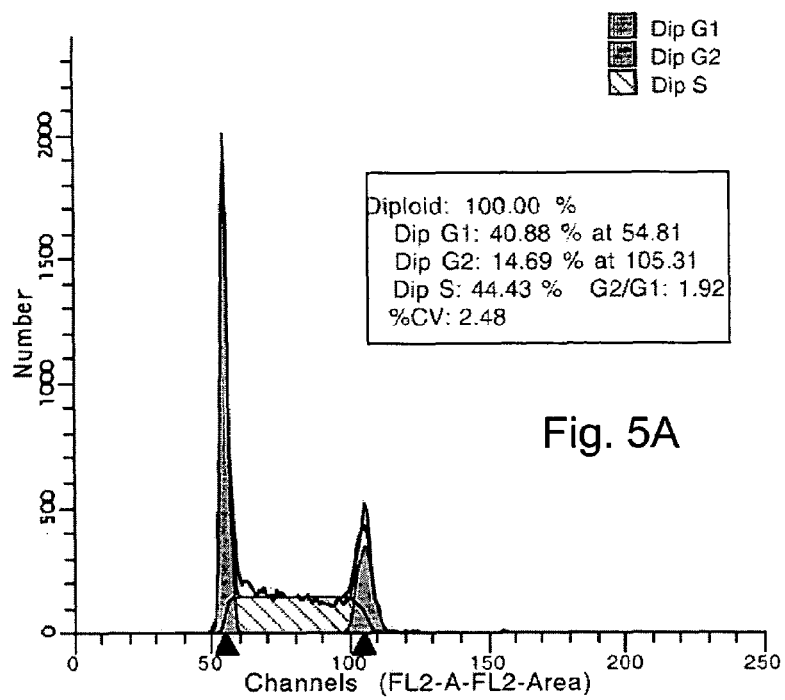
FIGS. 5A-5D are cell histograms showing the results from flow cytometry analysis of chemoprotective polyamine-treated 23SK skin cells.
Figure 5B:
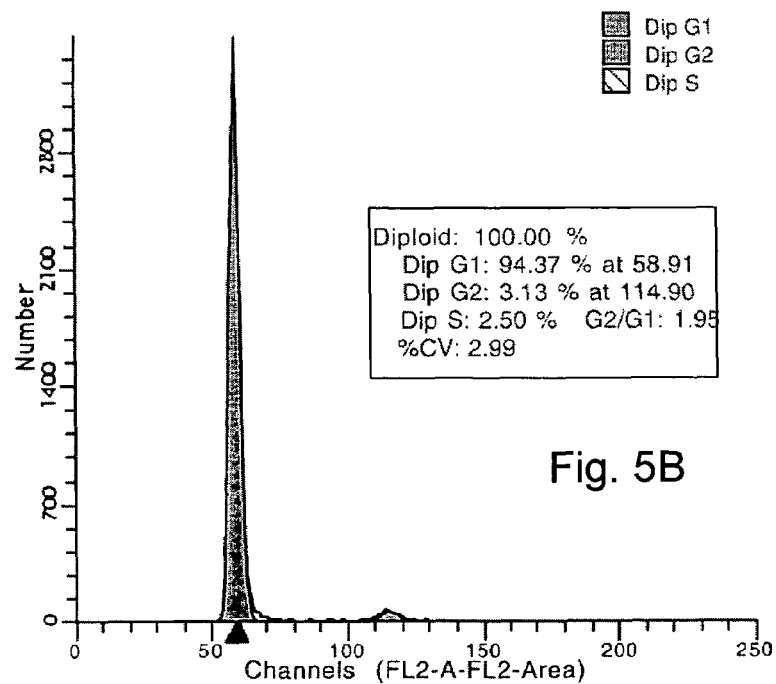
Figure 5C:
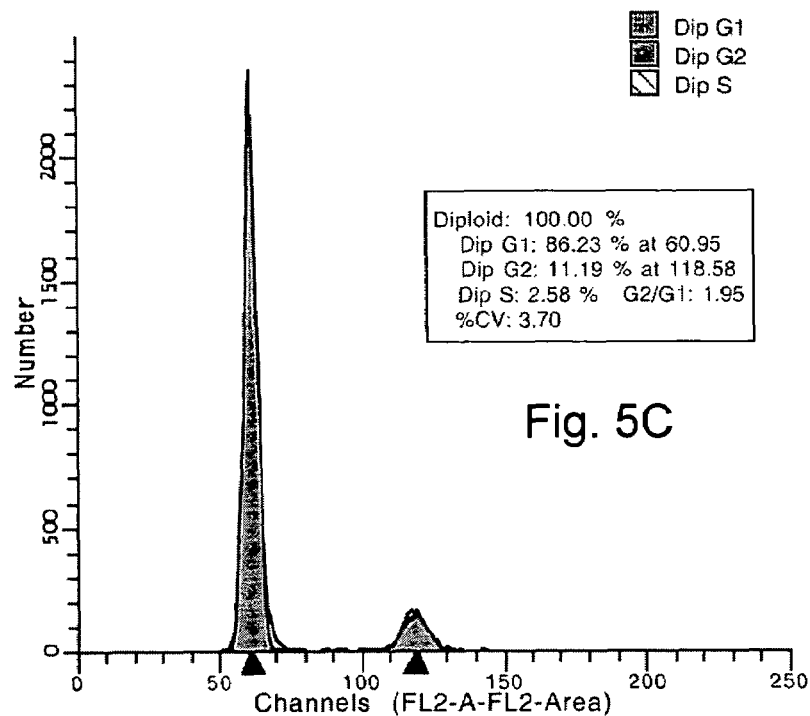
Figure 5D:
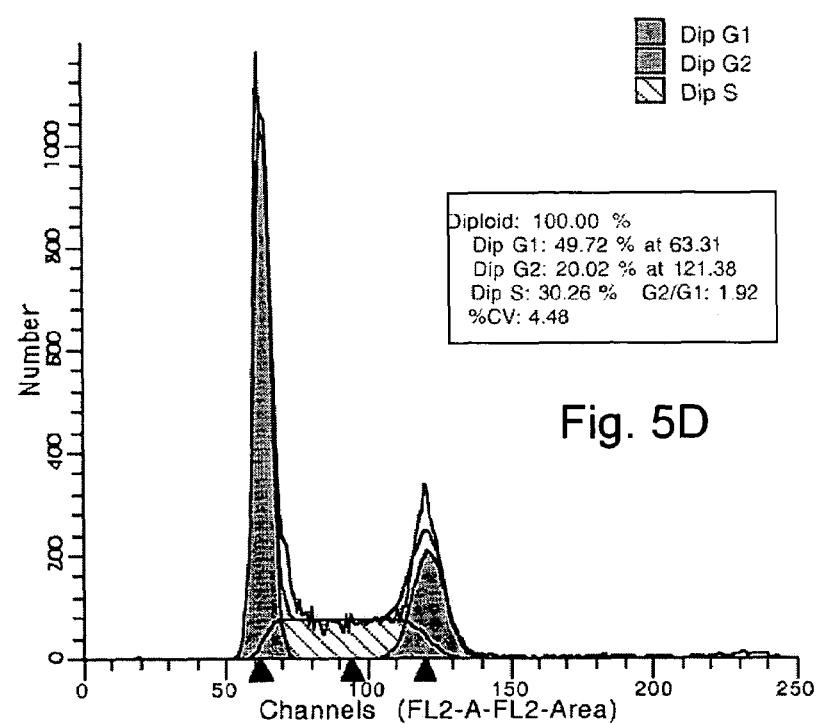
Figure 6A:
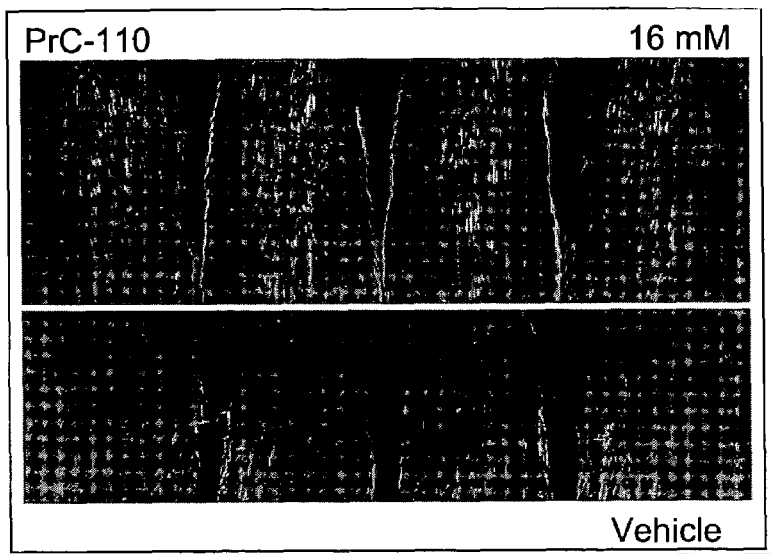
FIGS. 6A-6E illustrate the efficacy of topically-applied chemoprotective polyamines in protecting against chemotherapy-induced alopecia (hair loss) in a rodent model.
Figure 6B:
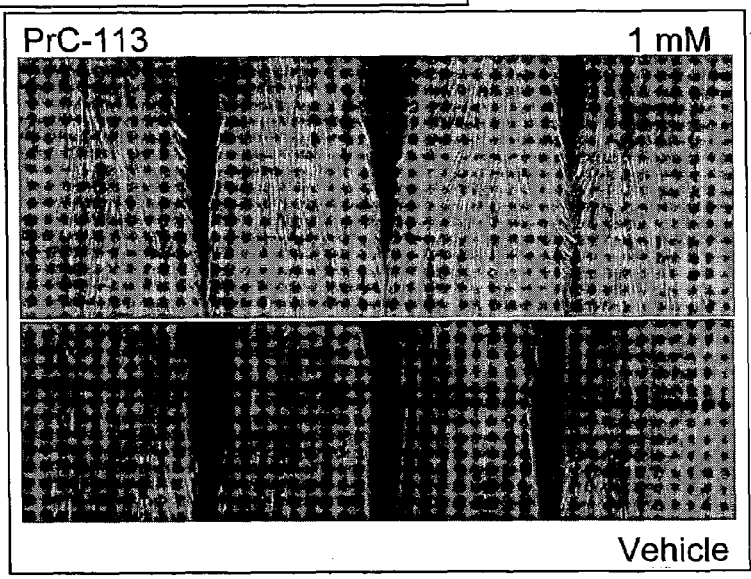
Figure 6C:
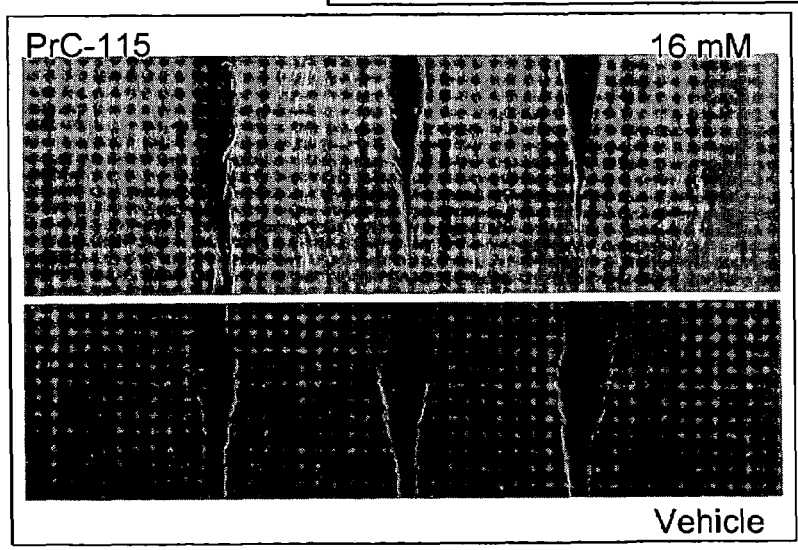
Figure 6D:
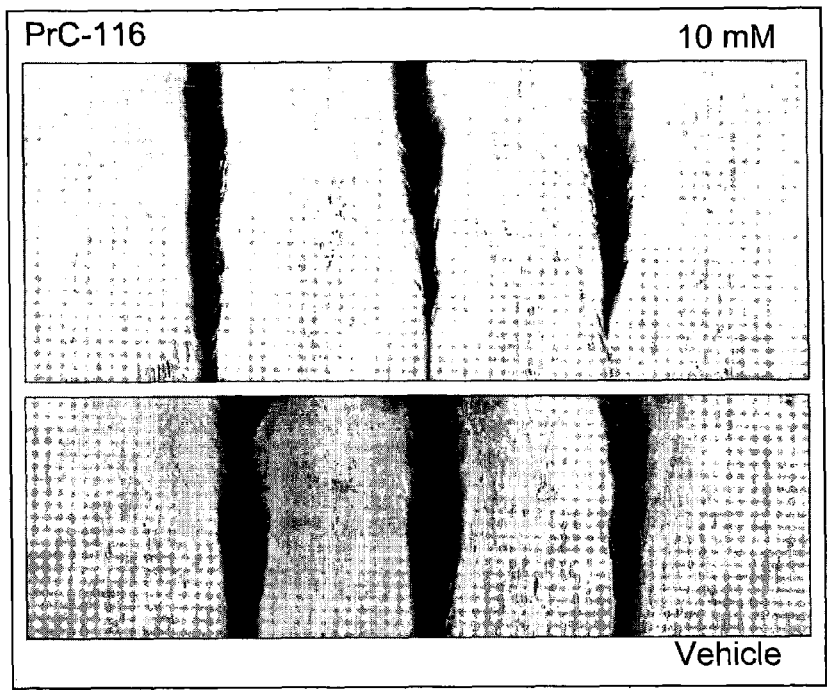
Figure 6E:
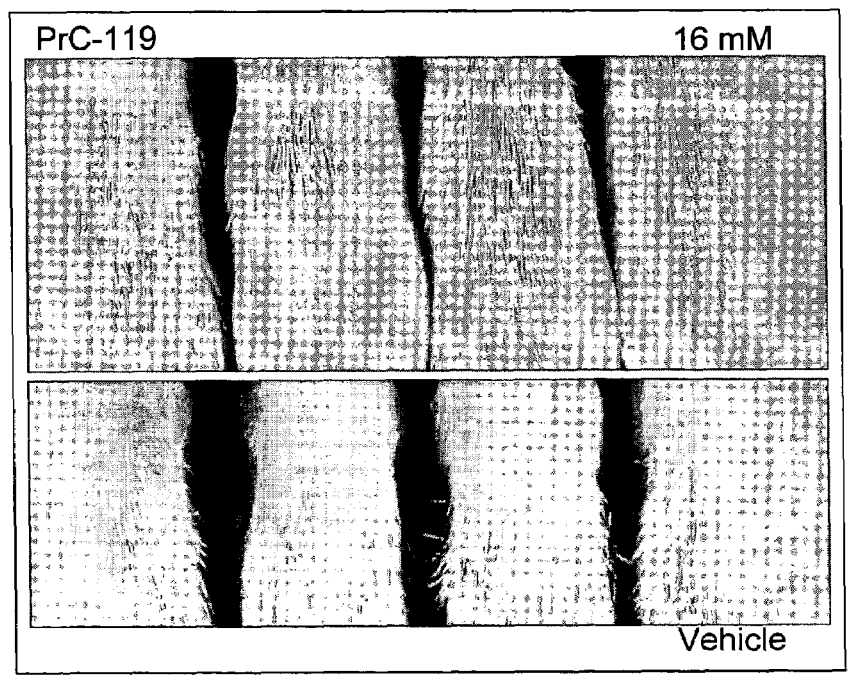
Figure 7A:
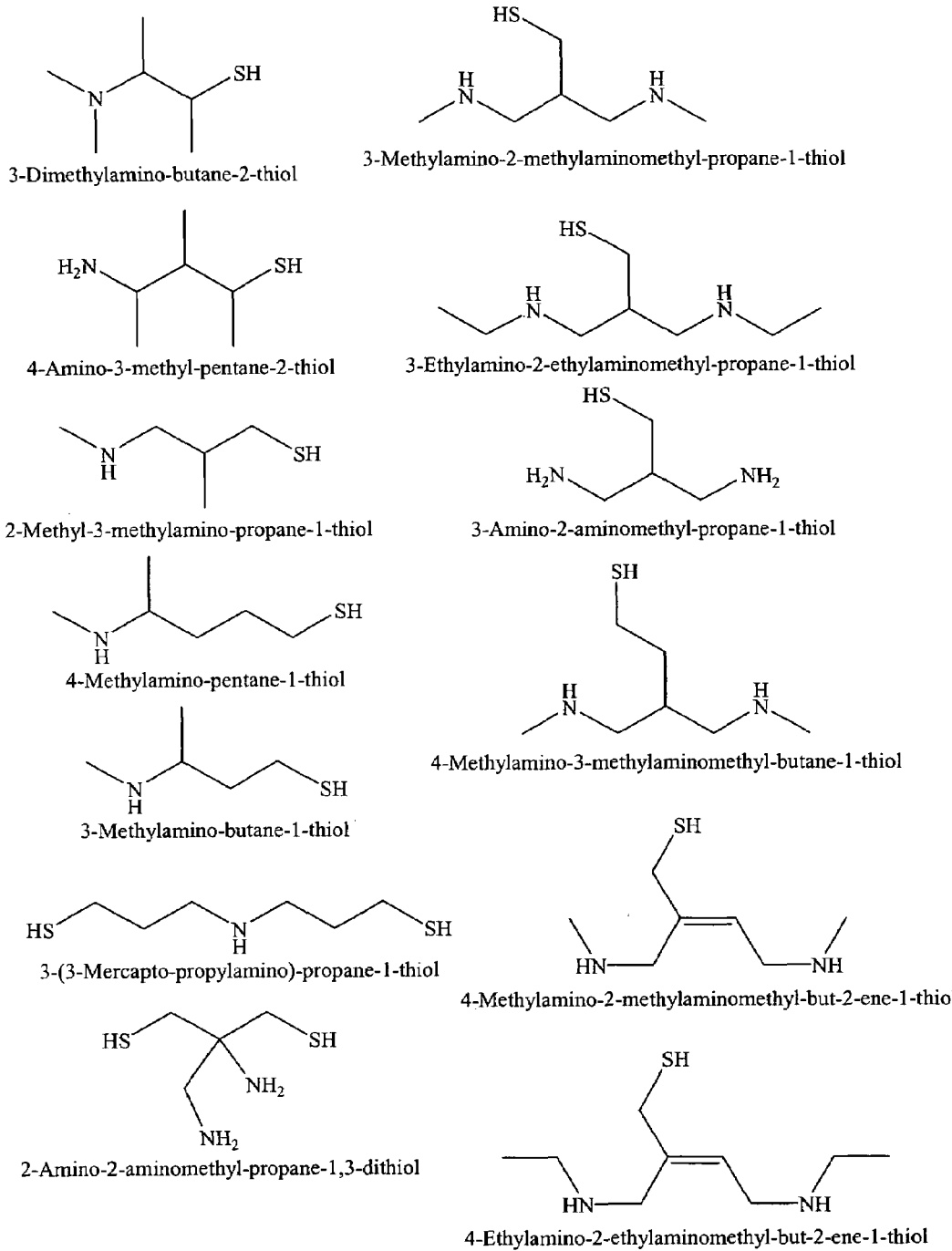
FIGS. 7A-7C illustrate exemplary chemoprotective amino thiol compounds of the invention.
Figure 7B:
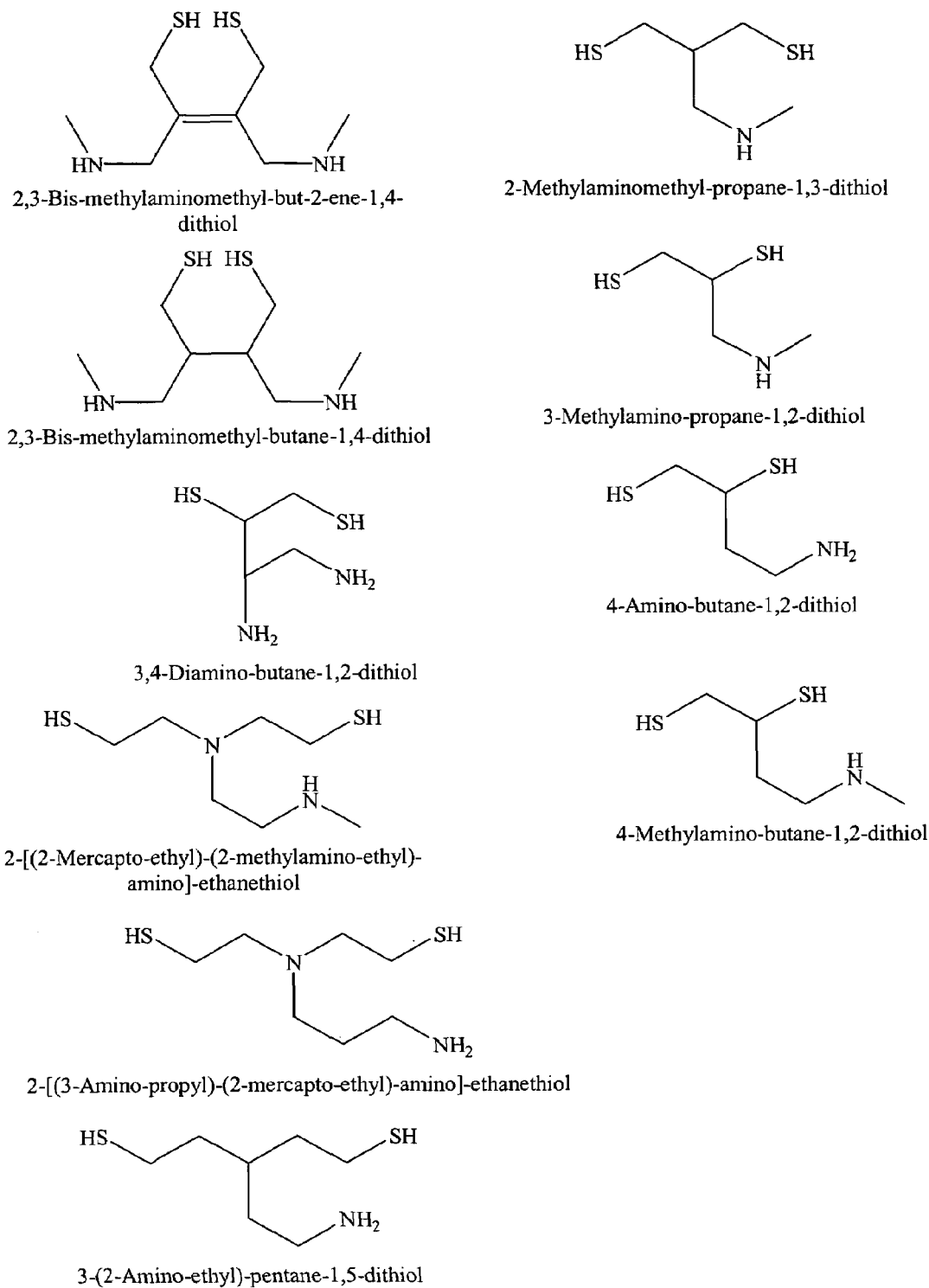
Figure 7C:
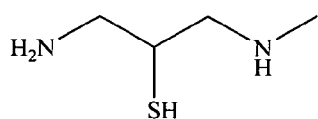
Figure 7C:
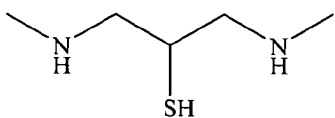
Figure 7C:
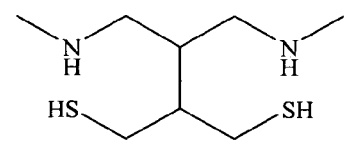
Figure 7C:
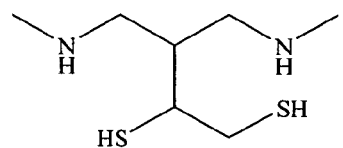
Figure 7C:
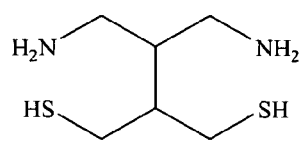
Figure 7C:
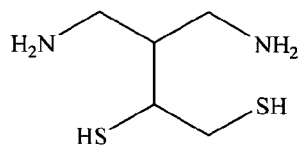
Figure 8A:
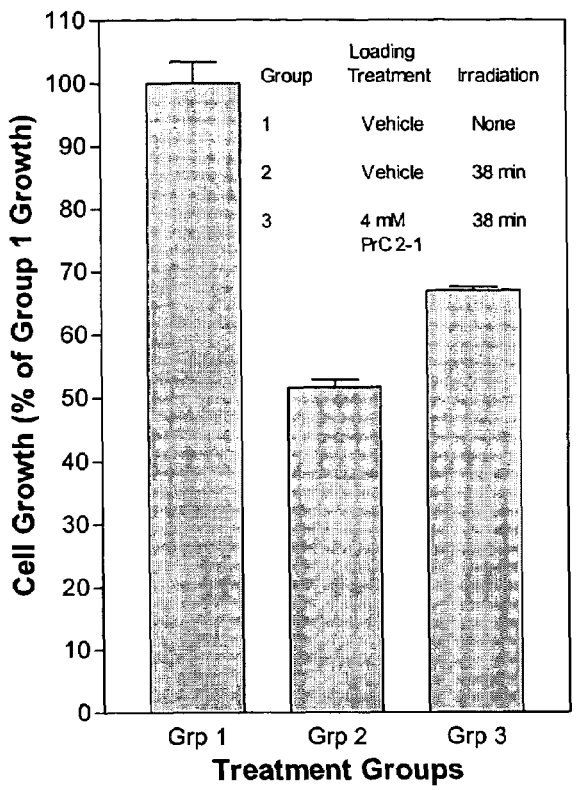
Figure 8B:
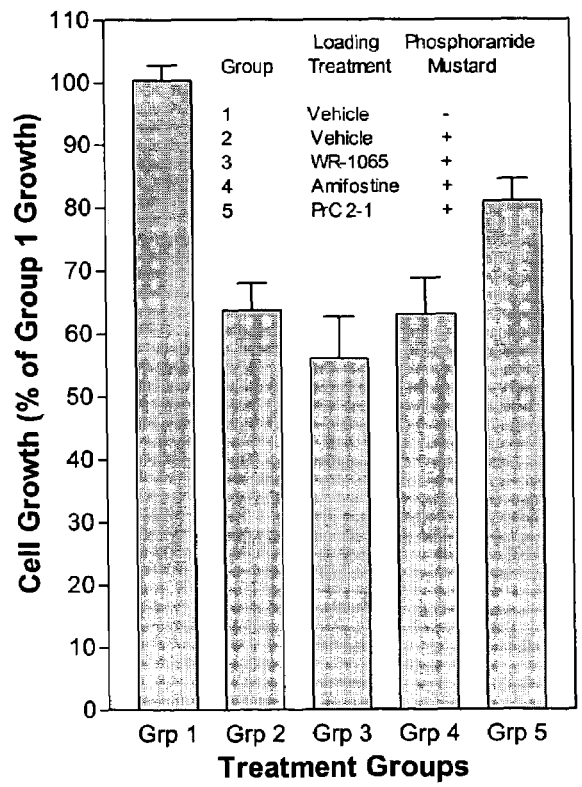

FIG. 3 illustrates that chemoprotective polyamines are able to induce expression of the negative cell cycle regulatory protein, p21, after exposing the human skin cells to the polyamine molecules. FIG. 3B shows that the induced p21 level is greater after a 30 hr exposure compared to a 50 hr exposure to drug. In these experiments, the 23SK human skin cells were exposed for 30 hr to an "$IC_{80}$" dose of each of the indicated chemoprotective polyamines and then lysed. Cell extracts were then prepared in order to measure p21 levels by western analysis (FIG. 3A). Results are summarized in Table 3. Although the ability of modified polyamines to induce p21 is known in the literature (Kramer, D. et al., *Cancer Res.* 59:1278-1286, 1999), it is a novel aspect of this invention that those chemoprotective polyamines with longer aliphatic "arms" were better able to induce expression of p21 as shown in FIG. 4.

TABLE 3

| Compound # [MW:HCl salt] | p21 fold-induction at $IC_{80}$ Dose |
|---|---|
| PrC-110 [523.9] | 2.91 |
| PrC-111 [739.0] | 2.22 |
| PrC-112 [954.2] | 2.45 |
| PrC-113 [1169.3] | 3.21 |
| PrC-114 [476.4] | — |
| PrC-115 [691.6] | — |
| PrC-116 [906.7] | 2.32 |
| PrC-117 [1121.9] | ~3.0 |
| PrC-118 [675.5] | — |
| PrC-119 [725.0] | 1.80 |
| PrC-120 [1155.3] | 2.01 |
| PrC-121 [1169.3] | 3.26 |
| PrC-122 [940.2] | 1.70 |
| PrC-123 [906.7] | 2.22 |
| Colcemid | 3.31 |

In FIG. 5, cell histograms showing the results from flow cytometry analysis of chemoprotective polyamine-treated 23SK skin cells are shown. FIG. 5A shows that for untreated, exponentially growing 23SK cells, 59.12% of the cells are present in the S+G2 cell cycle compartments, whereas only 40.88% of the cells are in the G1 compartment. FIG. 5B shows, as a control treatment, that incubation of cells in serum-free medium causes a sizable reduction in S+G2 cell compartments (down to 5.63% total), and a sizable increase in cells now present in the G1 compartment (up to 94.37%). FIG. 5C shows that cells treated with PrC-117 for 72 hr also show a marked reduction in S+G2 compartments (down to 13.77%) and a marked increase in the G1 compartment (up to 86.23%). FIG. 5D shows that after the cells treated with PrC-117 for 72 hr are switched for 48 hr to medium devoid of the PrC-117 molecule, the distribution within cell cycle compartments is basically returned to that seen in cells previously untreated with chemoprotective polyamine (i.e., FIG. 5A). The transient nature of the cell cycle block induced by chemoprotective polyamines is believed to be an important aspect of their efficacy, i.e., their ability to block cell cycle progression in stem cells during the course of chemo- or radiotherapy, and the resumption of normal stem cell division after a given cancer therapy course has been completed. Table 4 shows that, of the nine chemoprotective polyamine molecules tested, three caused G1 cell cycle blocks with greater than 75% of the cells present in the G1 compartment, and each of these three molecules contained 16 carbon aliphatic arms.

TABLE 4

| Compond # [MM:HCl salt] | Cell Cycle Distribution At IC$_{80}$ Dose (%) | | |
|---|---|---|---|
| | G1 | S | G2/M |
| PrC-110 [523.9] | 60 | 26 | 14 |
| PrC-111 [739.0] | 60 | 25 | 14 |
| PrC-112 [954.2] | 61 | 23 | 16 |
| PrC-113 [1169.3] | 77 | 8 | 14 |
| PrC-114 [476.4] | — | | |
| PrC-115 [691.6] | — | | |
| PrC-116 [906.7] | 66 | 11 | 23 |
| PrC-117 [1121.9] | 86 | 11 | 3 |
| PrC-118 [675.5] | — | | |
| PrC-119 [725.0] | — | | |
| PrC-120 [1155.3] | — | | |
| PrC-121 [1169.3] | 76 | 4 | 20 |
| PrC-122 [940.2] | 67 | 15 | 18 |
| PrC-123 [906.7] | 68 | 10 | 21 |
| Colcemid | 8 | 11 | 81 |

Natural polyamines such as spermine, with a 3-4-3 configuration of aliphatic carbon chains containing terminal amine groups and separated by intervening amine groups, are known to bind avidly to cellular DNA in the cell setting. Synthetic polyamines, containing longer aliphatic carbon segments, typically of four carbons, have been shown to displace natural polyamines like spermine from DNA because of their greater binding affinity for helical DNA. At physiologic pH ranges, each of the amine groups of a polyamine backbone can protonated to yield an ammonium cation. Therefore, as the length of a polyamine increases, achieved by oligomerizing a —$(CH_2)_4$—NH— segment, for example, there are typically an increased number of ammonium cations distributed along the polyamine backbone for bonding with anions distributed along the DNA backbone. As a result, longer, synthetic polyamine analogs compete more effectively with spermine in vitro and in vivo for binding to DNA. Binding of polyamines to helical DNA has also been shown to confer conformational changes to the DNA, such as conversion of helical B DNA to A or Z forms of DNA. And, in vivo, polyamine analogs have also been shown to cause condensation and aggregation of DNA and chromatin within mammalian cells (Basu, H., et al., *Cancer Res.* 49: 5591, 1989; Basu, H. et al., *Biochem. J.* 269:329, 1990). Though not intending to be bound by any particular theory, it is possible that the tight binding and associated distortion of normal helical structure, which is optimized in the design of chemoprotective polyamines as provided herein, provides pharmacologic benefit in at least three ways. First, the pharmacologic, growth inhibitory activity is reversible, as shown, for example, for the PrC-117 molecule in FIG. 5, i.e., by simply stopping topical application, the treated cells are released from growth inhibition thus yielding a 'transient' growth regulation. Second, distortion of helical DNA and the formation of single-stranded bubbles is likely to be a cause, or to be closely related to a cause, of the induced expression of p21 and the G1 cell cycle block that is associated with its induced expression. Third, for many electrophilic, alkylating drugs, reaction with DNA occurs in two steps, the first step requiring intercalation of the drug molecule between nucleoside bases in helical B DNA, and a rapid second step involving alkylation of the adjacent DNA base by the drug molecule. By condensing and altering normal DNA helical form, chemoprotective polyamines are expected to significantly reduce alkylation of cellular DNA by electrophilic drugs. Likewise, condensation and alteration of DNA helical form by polyamine binding in vitro has also been shown to dramatically reduce the number of single strand breaks induced when the DNA is directly irradiated in vitro (Spotheim, M., *Int. J. Radiat. Biol.* 68: 571-577, 1995).

When comparing chemoprotective polyamines to those polyamine analogs that have been previously described, there are a number of marked differences. For instance, Edwards (U.S. Pat. Nos. 5,217,964 and 5,434,145) attached one or more alkyl-thiophosphate or alkyl-thiol groups to one or more of the backbone amines of short aliphatic polyamines, or to one or more backbone amines as well as to one or more terminal benzyl groups on equally short polyamines. In comparison, the present inventors have designed and synthesized chemoprotective polyamine molecules which: i) optimize both the polyamine side chain ("arm") length and overall molecule length to achieve tight DNA binding, ii) project or "display" a protective functional group physically away from the DNA to which the chemoprotective polyamine is strongly bound, iii) attach the functional group to a polyamine backbone carbon atom instead of to one of the backbone amine groups, iv) in certain embodiments, display functional groups from allylic positions of olefinic core segments that are present in chemoprotective polyamines; this is done by design to enhance reactivity of the group, v) include a range of functional groups that are "displayed," including —SH, —OH, —$NH_2$, —NHR, —$NR_2$, —SH and —$SCH_3$ moieties, singly or in combination, as well as other groups that are known to vary in their degree of nucleophilicity or ability to scavenge free radicals, vi) include the display of more than one functional group per polyamine molecule, and vii) in some embodiments, include a rigid platform from which the functional group is projected or displayed on a spacer aliphatic chain away from the DNA in a manner that better enables the "sentinel group" to scavenge or trap electrophiles/oxygen radicals from the cellular milieu before they attack other known nucleophilic groups within DNA, such as the 2-amino group of deoxyguanosine.

This ability to scavenge and trap chemical/physical reactants within a cell does not require the chemoprotective polyamine to be physically attached to cellular DNA or RNA. Rather, simple molar presence of such nucleophilic or other protective functional groups in cells would be expected to be protective. For instance, previous work in the field has shown a positive, linear correlation between the intracellular concentration of the physiologic nucleophile, glutathione (GSH), and the concentration of an electrophile required to kill the exposed cells (Ho, D. and Fahl, W. E., *J. Biol. Chem.* 259: 11231-11235, 1984). In another mechanism by which chemoprotective polyamines might protect cells against cytotoxic threats, they may serve as a "stealth" vehicle by which to load cells with —SH or other nucleophilic or protective groups. Whereas, it is well known in the field (Levy, E. et al., *Proc. Natl. Acad. Sci.* USA 90:9171-9175, 1993) that the SH-containing nucleophile, glutathione, is not taken up by cells in a physiologic setting, the cell membrane polyamine transporter (PTS), which is known to mediate the uptake of polyamines, molecules containing multiple charged sites, should efficiently transport functional group-displaying polyamines into cells, and that this would provide an efficient means to "load" cells with, e.g., an SH-containing polyamine, which could serve as a glutathione surrogate. Once loaded with the polyamine, these cells would be protected from subsequent toxic challenges, such as those seen with transient chemotherapy and radiotherapy regimens. The results in the tables and figures that show the same growth regulating efficacy for each of the SH-containing chemoprotective polyamines (i.e., PrC-114, PrC-115, PrC-116, PrC-117) as for those chemoprotective polyamines without SH groups implies that the SH-containing molecules are transported into the human fibroblasts equally well, and that they bind with equal affinity to cellular DNA. Moreover, the fact that each of the SH-displaying chemoprotective polyamines exemplified herein has shown protective activity in the rat cytoxan-induced alopecia assay demonstrates that the displayed nucleophile is also active within the cell milieu.

One distinction between chemoprotective polyamines and chemoprotective amino thiols is the overall mass of the molecule to which the single or multiple —SH group(s) is/are attached. With chemoprotective polyamines, the inventors found that by attaching a single —SH to a polyamine with 4, 6, 8, or 10 amines per molecule, the majority of the protective effect resulted from the growth suppression associated with the long polyamine "arms." Indeed, efforts to achieve very high concentrations of —SH in cells were hampered because very high concentrations of long polyamine arms were highly growth suppressing. In the case of the smaller chemoprotective amino thiols of this invention, the ratio of sulfur to carbon within a given molecule is much higher, and this enables topical therapies where very high concentrations (e.g., 800-1200 mM) of amino thiol can be applied to skin, thus achieving very high concentrations of tissue —SH level prior to a toxic threat, without any apparent toxicity to the skin resulting from the topical amino thiol itself. Thus, attaching one or two thiol groups to a small, mono- or diamine, enables very high tissue —SH levels with only modest growth inhibition achieved through interaction of the mono- or diamine with cellular DNA.

The structures of the chemoprotective amino thiols of the present invention are significantly different from the structures of amifostine and its metabolites, particularly WR-0165. First, in amifostine, the terminal —SH group is capped with a phosphate group that must be enzymatically removed to enable protective activity. In contrast, the preferred amino thiol structures of the present invention are not phosphate-capped, and thus, they require no metabolic activation by epithelial cells that are at-risk from radiotherapy or chemotherapy. Second, the displayed —SH group in preferred and exemplary amino thiols of the present invention is "displayed" in a plane that is perpendicular to the backbone of the amino thiol that interacts with DNA rather than in the same linear plane as seen with amifostine. Third, the —SH groups in the present amino thiols are generally tethered to the perpendicular amine backbones by a —$CH_2$—chain that displays the —SH further away from the DNA helix than that seen with the amifostine metabolite WR-1065. Fourth, in several of the exemplary amino thiol structures, more than one —SH is present on the same molecule; thus, for every mole of amino thiol taken up by at-risk cells, two moles of —SH are delivered. Fifth, terminal amines are "capped" with methyl or ethyl groups to prevent or diminish molecule catabolism and thus, enable higher drug concentrations in mammalian cells, Sixth, whereas the linear aminothiols WR-1065 and cysteamine caused a cell cycle block in G2, PrC-210 was shown to cause a cell cycle block at a different point in the cell cycle, for example, in the G1 phase of the cell cycle. Seventh, whereas the G2 cell cycle block induced by cysteamine and WR-1065 are not reversible, the G1 cell cycle block induced by PrC-210 is reversible, for example upon washout or removal of the drug. Eighth, PrC-210 treatment of human skin cells induces expression of the cell cycle regulator, p21, whereas treatment with the linear aminothiol, cysteamine, does not induce such expression.

It has also been discovered in accordance with the present invention that cysteamine ($NH_2$—$CH_2$—$CH_2$—SH) is useful as an active agent in pharmaceutical preparations for use in methods for protecting non-cancerous, rapidly dividing cells in a patient's body from the toxic effects of chemotherapeutic agents or radiotherapy administered to the patient. Using rodents as a model, application of 600-1200 mM cysteamine to the backs of rats two hours prior to radiation treatment was found to eliminate radiation dermatitis in the treated animals. Furthermore, in the in vitro assay described in Example 5, pre-loading of cultured cells with 4 mM cysteamine 30 minutes before exposure to phosphoramide mustard conferred a protective effect to the cells, thus demonstrating the efficacy of this compound for protecting against the side effects of chemotherapeutic agents, as well as radiation therapy.

Another difference relates to the particular stage of the cell cycle affected by the compounds. In some studies, cysteamine acted by causing cells to arrest in G2/M (Jeitner T M and Renton F J, *Cancer Lett.* 1996 May, 15;103(1): 85-90). Similarly, it has been shown that WR-1065 and amifostine interfere wth cell division by arresting cells in the G2 phase, possibly because of interference with topoisomerase II (Snyder and Grdina, *Cancer Res.* 2000 Mar. 1;60(5):1186-8). The compounds of the present invention, however, appear to induce a reversible cell cycle block during the G1 phase (see Example 10).

Another way to increase the molar presence of nucleophiles/scavengers within the nuclear environs is to display more than one such functional group on each chemoprotective polyamine molecule. In embodiments where two —SH groups are displayed on a single polyamine, then a reducing agent such as sodium borohydride or others as known in the art may added to the pharmaceutical preparation to reduce any —S—S— disulfide bonds that might be formed when —SH groups are present in an oxygen containing medium. An alternate strategy to avoid disulfide bond formation is to "cap" the displayed sulfur atom with a $CH_3$ group to prevent interaction of the sulfur atoms, while still retaining the capacity of the sulfur atom to scavenge electrophiles/oxygen radicals.

The use and placement of protective functional groups on the backbone of chemoprotective polyamines is also significantly different from the attachment of —$CH_2CH_2SPO_3H_2$ or —$CH_2CH_2SH$ groups to polyamines described by Edwards in U.S. Pat. Nos. 5,434,145 and 5,217,964. In U.S. Pat. No. 5,434,145, Edwards showed bonding of alkyl-thiophosphate or alkyl-thiol groups to one or more of the 3-4 backbone amines present in the short polyamine molecules. By modifying the secondary amines in the polyamine backbone with alkyl-thiophosphate groups, the amines were converted to tertiary amines, which markedly alters the basicity of the individual modified amine, as well as the overall polyamine molecule. The attenuated basicity of the individual amine groups is accompanied by an alteration in 3-dimensional structure at these sites. With added alkyl functionality on the amine nitrogen atoms, steric bulkiness increases, so the ability or freedom of the molecule to rotate and twist at these sites is markedly reduced. The altered basicity and steric constraints in these short spermine-like polyamines perturbs DNA binding by the polyamine as compared to their natural polyamine counterparts. Given the already very high $IC_{50}$ concentration of spermine for DNA binding/precipitation (nearly 1,000-fold higher than for most chemoprotective polyamines; see Table 2), it is possible that the modification of backbone amines described by Edwards would eliminate DNA binding altogether in cells at the concentrations of drug that could be pharmacologically achieved. The attenuated basicity of the amine-modified polyamine molecules in Edwards could also affect their pharmacologic delivery characteristics. In topical applications to skin and other epithelial surfaces, there is an accepted relationship between the degree of ionization at physiologic pH of an applied drug and the degree to which it permeates or traverses the surface cells. In contrast to Edwards, the functional group used in the chemoprotective polyamines provided herein, whether —SH or one of several other groups (e.g., OH, N-ethyl, N-methyl, N-dimethyl; see FIG. 1), is bound to a carbon atom within the polyamine backbone. This designed tends to avoid perturbing the DNA binding characteristics of each of the backbone amine groups, while still achieving the display of reactive functional groups.

In U.S. Pat. No. 5,217,964, Edwards discloses the linking of one or more alkyl-thiophosphate or alkyl-thiol groups to the polyamine backbone through one or more terminal benzyl group(s) or through one or more of the backbone amine groups. Huber (*J. Biol. Chem.* 271:27556-27563, 1996) has shown that polyamines containing one or more aromatic groups can serve as inhibitors of the membrane polyamine uptake transporter, and predictably, they are not themselves taken up into cells. Consistent with the above observations, Edwards provides no information regarding biological activity for any of the structures proposed in U.S. Pat. No. 5,217,964 or 5,434,145.

FIGS. 6A-6E illustrate the efficacy of each of the indicated chemoprotective polyamines in protecting against Cytoxan-induced alopecia in the rat model (Hussein et al., 1990, infra). In this protocol (See Example 2), chemoprotective polyamines are applied topically to the rat pups' backs in an alcohol:water delivery vehicle, once per day, for five days before and five days after a single systemic dose of Cytoxan. As seen, topical chemoprotective polyamines conferred significant protection against the generalized alopecia that was seen to occur in the vehicle-treated rat pups.

D. Pharmaceutical Preparations and Methods for Topical and Local Administration

As described above, the chemoprotective amines of the present invention have been shown to inhibit the growth of normal human skin cells, to modify normal B-DNA helical structure, to induce expression of the negative cell cycle regulator, p21, to cause a G1-specific cell cycle block, and to protect against chemotherapy-induced alopecia and dermatitis in an animal model. Thus, the compounds of the invention are particularly suitable for treatment of humans to prevent the local side effects of cancer chemotherapy and radiotherapy. Based upon their growth regulatory effects, chemoprotective polyamines may also find utility in other applications where inhibition of cell growth would be advantageous, including regulating proliferative conditions of the skin, such as psoriasis and dermal nevus.

Two important targets for delivery of such protective therapies are (1) the epithelial cells of the skin, including hair follicles and the epidermis, and (2) the epithelial cells lining the oral and entire gastrointestinal (GI) or urogenital tract. The method of protection of these tissues with chemoprotective amines comprises administering to a population of epithelial cells a composition consisting of a chemoprotective amine and a delivery vehicle for a time and in an amount effective to protect the non-neoplastic cells from damage during the cancer chemotherapy or radiotherapy. In one embodiment, the method is used to prevent alopecia during cancer therapy, by topically applying the composition to the scalp. In another embodiment, the method is used to prevent gastrointestinal distress due to cancer therapy by administering the composition orally. In another embodiment, the method is used to prevent mucositis from chemotherapy or radiotherapy by administering the composition topically to the appropriate region of the body. In yet another embodiment, the method is used to prevent radiation-induced dermatitis, skin rash, and ulceration at the site of irradiation by applying the composition to the skin.

Administration of chemoprotective amines to human or non-human subjects can be achieved in several ways. The preferred administration route is topical, to tissue sites including the skin, as well as oropharyngeal and gastrointestinal mucosal surfaces. It can also be delivered locally to an internal organ, tissue or regions thereof. It should be noted, as with all pharmaceuticals, the concentration and total amount of amine administered will vary depending upon the tissue being treated, the mode of administration, the size and condition of the subject being treated, and the particular chemoprotective amine being used.

Compositions of chemoprotective amines formulated in delivery vehicles are well-suited to be administered topically to the skin or surfaces of the mouth, GI or urogenital tract. Pharmacologic concentrations of chemoprotective amines can protect normal, non-neoplastic cells from cancer therapy-associated cell damage. By producing a local gradient effect within the tissues, the topically applied amine produces a local protective effect at the intended region. This dose-dependant gradient of topical drug can effectively protect normal proliferating cells rendering them less susceptible to radiation or chemotherapy. Importantly, while this local effect would protect normal cells, in contrast, any deeper-seated tumor cells would be less affected by the topical amine composition, and would remain sensitive to the cancer therapeutic. Moreover, topical delivery of a chemoprotective amine, which has a highly positive charge at physiologic pHs, should diminish any systemic exposure and limit the effect on any tumor cells or normal host organ cells. Given the host toxicity that has been previously observed when polyamine analogs were administered systemically (Creaven, P. et al., *Invest. New Drugs* 15:227-234, 1997; Streiff, R and Bender, J., *Invest. New Drugs* 19:29-39, 2001), this provides another important reason to avoid systemic delivery of the chemoprotective amine molecules. The intended protection of normal tissue is achieved by an appropriate formulation of chemoprotective amine in combination with an appropriate delivery vehicle depending on the administration site (e.g. dermal/intradermal or mucosal). A pharmaceutical composition comprising a chemoprotective amine formulated with an appropriate delivery vehicle will have utility in any normal cell type susceptible to the side effects of cancer therapy that is accessible by topical delivery.

Thus, the chemoprotective amines of the invention are administered topically (or locally) to protect patients from the side effects of cancer therapy. The term "topical" denotes the administration of a drug intended to act locally rather than systemically. In the present invention, "topical" or "local" delivery is directed to epidermal and dermal cells of the skin and scalp (including cells lining hair follicles), as well as mucosal cells of the mouth, salivary glands, throat, gastrointestinal system and urogenital tract. For some of these latter locations, compositions may be formulated for oral or nasal delivery, or as suppositories. The goal of such delivery systems is to contact these internal surfaces topically with the chemoprotective amine.

The local delivery of drug molecules within the skin or mucous membranes using a noninvasive delivery system has many attractions, including patient acceptability due to the noninvasiveness of the procedure, avoidance of gastrointestinal digestion and disturbances, and first-pass metabolism of the delivered molecule. Topical delivery is not an efficient means for systemic drug delivery. It is estimated that only between 1%-15% of a drug in most topical formulations is systemically bioavailable. In preferred embodiments of the invention, less than 10%, preferably less than 5% and most preferably less than 1% of the chemoprotective amine, provided topically e.g., dermal, intradermal, mucosal or GI epithelial delivery, move to reach the dermis and/or other underlying tissues.

Topical delivery vehicles can take the form of aqueous or aqueous:alcohol solutions, emulsions, creams, lotions, ointments, gels or liposomes.

Solutions are the most traditional types of formulations for topical dermal drugs, where the agent is solubilized in a solvent. Solvent-based systems are simple and effective constituents of topical delivery vehicles for some drugs. Alcohols are the most commonly used solvents for topical solutions. Typically, the drug is combined into a water and alcohol mixture. The alcohol content varies between 10-100%. Alcohols used include ethanol, propylene glycol, polyethylene glycols, methanol, or butanediol. Each of these types of alcohols is suitable for use in the present invention; others not listed are also suitable, as would be understood by one of skill in the art. High alcohol content solutions, such as solutions of 70% ethanol in water, or solutions containing 60% ethanol, 20% propylene glycol and 20% water, are particularly good at penetrating the *stratum corneum* of the epidermis. Topical minoxidil, a hair regrowth treatment, uses the latter formulation as the delivery vehicle.

Solution-based delivery systems are particularly suitable for the delivery of small organic molecules. In one preferred embodiment, particularly for administration of chemoprotective amines to the epidermis, alcoholic solutions, as described above, are utilized. An aqueous alcohol-based delivery vehicle has been proven to be highly effective for topical administration of chemoprotective amines. Advantages of this delivery system include, ease of manufacturing, ease of application, fast drying, lack of residue on skin, and ease of analysis of active drug compound after formulation. Solution-based formulations are typically administered using dropper bottles or as aerosols.

Emulsions form the basis of cream and lotion-type formulations. Typically, these formulations are colloidal dispersions composed of two immiscible phases; an oil phase and an aqueous phase with an emulsifier. Typical oils used in emulsions include stearyl alcohol, isopropyl lanolate, isopropyl myristate, cetyl alcohol, and vitamin E. Emulsifiers are essentially surfactants that lower the surface tension of the immiscible phases. Useful emulsifiers include fatty acid esters or stearates of glycerol, sorbitan, or polyoxyethylene (POE) and the like. Depending on the location of the oil and water, emulsions are oil-in-water, water-in-oil or combinations thereof. The preparation of an emulsion commonly requires some mechanical shear force with heat to mix the internal and external phases. Most topical emulsions contain viscosity builders such as natural gums (alginates, carrageenan, tragacanth, pectin, xanthan or collagen) at 1-5% to thicken the preparation. Higher percentages of viscosity builders produce creams, a lower percentage form lotions. Complete formulations for emulsions (creams and lotions) include, for example, water, alcohol, propylene glycol, sodium lauryl sulfate and white wax. In alternative formulations, they include water, alcohol, glycerol, phosphatidyl choline, lysophosphatidyl choline and triglycerides. For administration of chemoprotective amines to the epidermis, emulsions are particularly useful. Ease of administration, good local retention and slow release of drug are some of the attractive characteristics of emulsions for a topical delivery system.

Ointments are composed of fluid hydrocarbons meshed in a matrix of higher melting solid hydrocarbons. The hydrocarbon ointment base is typically petrolatum and white ointment. In one embodiment, ointments are prepared by melting the base, followed by the addition of excipients, such as antioxidants to the fluid. The drug is then suspended into the ointment by milling. Due to the high oil content, ointments tend to be greasy. Adding components, such as microcrystalline cellulose, which gives the ointment a dry feel on the skin, can reduce greasiness. All ingredients listed above for preparation of ointments are suitable for use with the pharmaceutical compositions and methods provided herein, as well as unlisted ingredients typically employed for such purposes by one of skill in the art.

Gels are semisolids consisting of a gelling agent that is penetrated with liquid solvent. The concentration and the molecular weight of the gelling agent affect the consistency of vehicle formulation. The gelling agent is a suspension of either large organic or small inorganic molecules. The large organic molecules consisting of either natural or synthetic polymers exist as randomly coiled chains that entangle and form the gel structure. Some common polymers of this kind are natural gums, cellulose derivatives and acrylic acid polymers. Another class of these gels, called thermally sensitive gels, is prepared from poloxamers. In contrast, the small inorganic molecules form the gel structure by forming a somewhat organized three-dimensional network. Common small inorganic polymers include colloidal solids found in silica and clays. The nature of the solvent determines whether the gel is a hydrogel (water-based) or an organogel (non-aqueous solvent based). Gels are attractive topical delivery vehicles for chemoprotective amines because they are relatively easy to prepare and tend to have a long residence time at the site of application allowing the slow release of compound at the desired site. All ingredients listed above for preparation of gels are suitable for use herein. Unlisted ingredients typically employed by one skilled in the art for such purposes are also contemplated for use herein in conjunction with or as substitutes for the exemplified ingredients and components.

Liposomes are vesicles consisting of amphipathic lipids arranged in one or more concentric bilayers. When lipids are placed in aqueous medium, the hydrophilic interaction of the lipid head groups with water results in the formation of multilamellar and unilamellar systems or vesicles which resemble biological membranes in the form of a spherical shell. Liposomes may be small (0.025-0.05 um) to large multilamellar vesicles (0.05-10 um). Lipids used to prepare the liposomes include phospholipids, sphingolipids, glycosphingolipids, saturated glycerides, steroids (e.g., cholesterol) and synthetic phospholipids. Liposomes are typically prepared by melting the lipid together in aqueous solvent with an emulsifier like POE. The drug is then added and the liposomes are generated through mixing or sonication. The drug is usually entrapped in the vesicle structure. These basic liposomes are sometimes referred to as "conventional liposomes." Several other types of liposomal preparations exist, including (1) sterically stabilized liposomes, which are surface coated with an inert hydrophilic polymer, such as polyethylene glycol; (2) targeted liposomes, to which are attached targeting ligands, such as antibodies or fragments thereof, lectins, oligosaccharides or peptides (e.g., choleratoxin B (CTB) is used to target liposomes to the gastrointestinal epithelium); and (3) reactive or "polymorphic" liposomes, which change their phase and structure in response to a particular interaction (this group includes liposomes sensitive to ions (pH, cations), heat and light, among other stimuli.

Liposomes are good vehicles for dermatological applications. Liposomal delivery offers certain advantages over more conventional formulations, including: (1) reduced serious side effects and incompatability from undesirably high systemic absorption; (2) significantly enhanced accumulation of the delivered substance at the site of administration due to high compatability of liposomes with stratum corneum; (3) ready incorporation of a wide variety of hydrophilic and hydrophobic molecules into the skin; (4) protection of the entrapped compound from metabolic degradation; and (5) close resemblance to the natural membrane structure and their associated biocompatibility and biodegradability. All ingredients listed above and for preparation of various types of liposomes are suitable for use in the present invention, as well as any other such ingredients typically employed by one skilled in the art for such purpose.

In order to achieve efficient delivery of a chemoprotective amine into the skin, one embodiment of the invention includes various formulations of liposomes (including but not limited to luminallipid-based vesicles, phospholipid-based vesicles, cationic liposomes, nonionic liposomes, non ionic/cationic liposomes, pegylated liposomes, PINC polymer, and propylene glycol and ethanol mixture (commonly used vehicle for administering minoxidil), and nonionic liposome/propylene glycol and ethanol mixtures. Reactive liposomes may be preferred for other embodiments of the present invention. Inclusion of cationic amphiphiles as a minor component of liposomes facilitates the association with negatively charged solutes, the rapid binding of liposomes to the cell surface, and the cellular uptake of liposomes. pH-sensitive liposomes have been developed to improve the efficiency of the cytoplasmic delivery of anti-tumor drugs, proteins, and nucleic acids. Most pH-sensitive liposomes have been prepared using phosphatidylethanolamine (PE). PE alone does not form liposomes and is prone to form the inverted hexagonal phase (HII). However, liposomes can be prepared by adding another bilayer-stabilizing, amphiphilic lipid component to PE. Titratable amphiphiles having a carboxyl group have been used as a component for the preparation of pH-sensitive liposomes. Because the ability to stabilize a bilayer membrane by these titratable amphiphiles decreases under acidic conditions, destabilization results in the fusion of the liposomes. pH-sensitive liposomes are stable at physiological pH, and are internalized by cells through an endocytic pathway, which exposes the liposomes to an acidic pH. Liposomes within the endosome are destabilized and possibly fuse with the endosome membrane, resulting in release of their contents into the cytoplasm without degradation by lysosomal enzymes.

In other embodiments of the invention, sterically stabilized, inert liposomes are particularly suitable. In still other embodiments, targeted liposomes may be used to advantage.

For many applications, mucosal delivery will be used for delivery of chemoprotective amines. Mucosal delivery defined here is the local delivery of chemoprotective amines to the mucosa of the mouth, GI, and urogenital tract. Mucosally active drugs, can be formulated as either solutions, emulsions or creams, ointments, gels or liposomes using the ingredients described above. In addition, there are also special excipients specifically designed for mucosal delivery. The description, composition, and applicability of these major types of mucosal delivery forms are set forth below. Each is considered suitable for practice of various embodiments of the present invention.

In general, the structure of the mucosal surface is composed of an outermost layer of stratified squamous epithelium, below which lie a basement membrane, a lamina propria followed by the submucosa as the inner-most layer. The mucosae of areas subject to mechanical stress such as the gingivae or the hard palate are also keratinized, similar to the epidermis. Depending on the keratinization, the mucosa is somewhat permeable. The permeability of oral mucosa is 4-4000 times greater than that of the skin. Permeability of intestinal mucosa is even greater. The cells of the epithelia are surrounded by an intercellular ground substance, mucous, the principal components of which are complexes of proteins, carbohydrates, lipids and ceramides. Primarily, special mucous-secreting cells, called goblet cells, synthesize mucous. However, in the oral mucosa, most of the mucous is produced by the major and minor salivary glands. Mucous forms a strongly cohesive gel structure that will bind to the epithelial cell surface as a gelatinous layer. The penetration of this mucous layer and the local retention of compound because of its permeability must be achieved for effective mucosal drug delivery. However, this route of administration is very important for the delivery of compounds designed to protect mucosal surfaces from cancer therapy. Since the mucosal surface is a common site in which many of the unwanted side effects occur, the use of formulated mucosally-active drugs designed to prevent these effects is warranted.

Issues to be considered with mucosal delivery are (1) low flux or drug transport through the mucous layer and (2) poor retention and bioadhesion at the mucosal site. Mucosal permeation enhancers are designed to improve drug flux or penetration at the mucosal surface. The use of these enhancers can increase drug permeability by 100-fold or more. Various permeation/absorption enhancers vary in molecular weight and physicochemical properties. In a preferred embodiment for mucosal delivery, permeation enhancers are included in formulations for delivery of chemoprotective amines to the mucosal surface. Most types of enhancers are detergents that include: sodium glycocholate, sodium taurocholate, polysorbate 80, sodium lauryl sulfate, lauric acid, and various alkyl glycosides. Other examples of enhancers include: dextrins (cyclodextrin, dextran sulfate), fatty acids (phosphatidylcholine, lysophosphatidylcholine), heterocyclic compounds (azone), and small molecules (benzalkonium chloride, cetyltrimethylammonium bromide). Each is contemplated for use in the present invention as are other unlisted ingredients typically used for such purpose, as would be appreciated by one of skill in the art.

The addition of mucoadhesives to the formulation can improve local retention of mucosally delivered compounds. In another preferred embodiment for mucosal delivery, mucoadhesives are included in the formulations of the invention. Mucoadhesive compounds are primarily synthetic or natural polymers that can adhere to the wet mucosal surface. These include synthetic polymers such as monomeric alpha cyanoacrylate, polyacrylic acid, hydroxypropyl methylcellulose, and poly methacrylate derivatives. Glue-like polymers include epoxy resins and polyurethanes. Naturally occurring mucoadhesives include chitosan, hyaluronic acid and xanthan gum. Each is contemplated for use in the present invention as are other unlisted ingredients typically used for such purpose, as would be appreciated by one of skill in the art.

Other delivery vehicles are also suitable for use in the present invention, particularly for administration of chemoprotective amines to the mucosa and lumen of the GI and urogenital tract. Nonlimiting examples include: (1) oils such as vegetable oils or fish oils (which can be encapsulated into standard gel capsules); and (2) emulsions prepared, for example, by dispersing polyoxyethylene ethers, e.g., 10-stearyl ether (Brij 76) in aqueous buffer.

Other examples of delivery vehicles suitable for the GI or urogenital mucosa include biodegradable microparticles (preferably in the range of 0.1-10 uM diameter) of polylactic polyglycolic acid, which have been used to deliver proteins to Caco-2 cells as an in vitro model system for gastrointestinal uptake via oral drug delivery (Desai et al., Pharm. Res. 14: 1568-1573, 1997). Significant uptake of proteins carried by polystyrene particles into cells lining the small intestine of the rat has been demonstrated (Hillery et al., J. Drug Targeting 2: 151-156, 1994). Indeed, delivery of protein-containing microparticles has been reported from the GI lumen all the way to the submucosal vasculature (Aphramaian et al., Biol. Cell 61: 69-76, 1987). Therefore, such polymeric microparticles are quite suitable for oral delivery of chemoprotective amines to gastrointestinal epithelial cells, which are found on the surface of the GI lumen.

Thus, chemoprotective amines are formulated as pharmaceutical preparations for topical or local administration to patients. The following sites of local administration of these pharmaceutical preparations are contemplated: oral, nasal, ophthalmic, gastrointestinal, urogenital and dermal (cutaneous). The term "patient" or "subject" as used herein refers to human or animal subjects (animals being particularly useful as models for clinical efficacy of a particular composition). Selection of a suitable pharmaceutical preparation depends upon the method of administration chosen, and may be made according to protocols well known to medicinal chemists.

The pharmaceutical preparation comprising the compositions of the invention are conveniently formulated for administration with a biologically acceptable medium such as water, buffered saline, alcohols, polyol (for example, glycerol, propylene glycol, liquid polyethylene glycol and the like), dimethyl sulfoxide (DMSO), oils, detergents, suspending agents or suitable mixtures thereof, as compatible with the specific delivery vehicles described above. The concentration of a particular composition in the chosen medium will depend on the hydrophobic or hydrophilic nature of the medium, in combination with the specific properties of the delivery vehicle and active agents disposed therein. As used herein, "biologically acceptable" or "pharmaceutically-acceptable" refers to those compounds, materials, compositions, and/or dosage forms that are, within the scope of sound medical judgment, suitable for contact with the tissues of human beings and animals without excessive toxicity, irritation, allergic response, or other problem complications commensurate with a reasonable benefit/risk ratio.

As used herein, "pharmaceutically-acceptable salts" refer to derivatives of the disclosed compounds wherein the parent compound is modified by making acid or base salts thereof. Examples of pharmaceutically-acceptable salts include, but are not limited to, mineral or organic acid salts of basic residues such as amines; alkali or organic salts of acidic residues such as carboxylic acids; and the like. Thus, the term "acid addition salt" refers to the corresponding salt derivative of a parent compound that has been prepared by the addition of an acid. The pharmaceutically-acceptable salts include the conventional salts or the quaternary ammonium salts of the parent compound formed, for example, from inorganic or organic acids. For example, such conventional salts include, but are not limited to, those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like. Certain acidic or basic compounds of the present invention may exist as zwitterions. All forms of the compounds, including free acid, free base, and zwitterions, are contemplated to be within the scope of the present invention.

The topical formulation can contain a variety of excipients that function to stabilize and solubilize the drug formulation, increase permeation, and protect and aid in the application to the skin. Oil or water-based excipients are primarily added to improve drug solubility and spreadibility to the formulation. Surfactants may be added to topical formulations as detergents, solubilizers, emulsifiers, and wetting agents.

It will also be appreciated by persons of skill in the art that pharmaceutical formulations of the invention may contain more than one chemoprotective amine. Various combinations of such agents may be useful for certain applications, and formulations of such combinations would be prepared according to the general guidelines set forth above. Moreover, one or more chemoprotective amines may be combined with other agents, such as other anti-proliferative agents or chemoprotective drugs, to provide a pharmaceutical formulation that is effective by two different modes of action. An anti-proliferative agent suitable for such use is the cyclin-dependent kinase II inhibitor described in PCT Application US00/05186, published Dec. 28, 2000 as WO 00/78289 or genistein, an inhibitor of tyrosine protein kinase. A chemoprotective agent suitable for such use is resveratrol (trihydroxy-trans-stilbene). Several classes of "chemoprotective inducing agents" (agents that induce the cell's endogenous defense processes) that may be combined with the chemoprotective amines of the invention are described in detail in commonly-owned, co-pending U.S. patent application Ser. No. 09/565,714, filed May 5, 2000, and International Patent Application No. PCT US01/14464, filed May 4, 2001, the entireties of each of which are incorporated by reference herein. Further, certain of those chemoprotective inducing agents also possess anti-proliferative activity.

The pharmaceutical preparation in one embodiment is formulated in dosage unit form for ease of administration and uniformity of dosage. Dosage unit form, as used herein, refers to a physically discrete unit of the pharmaceutical preparation appropriate for the patient undergoing treatment. Each dosage preferably contains a quantity of the chemoprotective amine calculated to produce the desired protective effect in association with the selected pharmaceutical carrier. Procedures for determining the appropriate dosage unit are well known to those skilled in the art. As used herein, "therapeutically effective amount" of an amount "effective" for a refers to an amount of a compound as described herein that may be effective to inhibit, or treat the symptoms of particular disorder or side effect, so as to obtain some improvement in condition or diminishment or reduction or symptoms. The term "prophylactically effective amount" refers to an amount of a compound as described herein that may be effective to prevent, inhibit, or diminish the onset the symptoms of a particular disorder or side effect.

Dosage units may be proportionately increased or decreased based on the height and weight of the patient. Appropriate concentrations for achieving protection of a target cell population or tissue from the toxic effect of a particular chemotherapeutic agent may be determined by dosage concentration curve calculations, as known in the art.

As one example, for topical applications, the chemoprotective amine may be used at concentrations ranging from 1-1200 mM in an appropriate carrier (e.g., alcohol solvent) applied to the scalp or other dermal site. The higher concentrations in that range, e.g., 400-1200 mM, are more suitable for the amino thiols of the invention, while the lower concentrations, e.g., 1-400 mM, more specifically 1-100 mM, are more suitable for the polyamines of the invention. These dosages are arrived at from results of experiments using a rodent model and the range of dosages is a function of results obtained from experiments using several different molecules that ranged in dose effectiveness. The volume of material applied to the skin ranges by size of surface area to be covered; e.g., scalp treatment for young children requiring 3-5 ml, the amount being increased in adults to 10-20 ml per application.

As another example, for gastrointestinal administration, the oral dose of the chemoprotective amine in an appropriate medium (e.g., solvent, liposome emulsion) is normalized to the lumenal surface area of the stomach and duodenum. This would assume that the patient consumes the material on an empty stomach upon rising in the morning.

The pharmaceutical preparation comprising the compositions of the invention may be administered at appropriate intervals, before, during, or after a regimen of chemotherapy and/or radiotherapy. The appropriate interval in a particular case would normally depend on the nature of the chemotherapy or radiotherapy and the cell population targeted for protection.

For instance, for prevention of chemotherapy-induced alopecia, solvents, liposomes or other delivery vehicles containing the chemoprotective amine can be further formulated to be delivered, (e.g., as a topical cream, or gel) to the scalp of a patient prior to scheduled administration of chemotherapy. By protecting the epithelial cells that line the exposed surface of hair follicles from the chemotherapy drug, the loss of hair commonly associated with cancer chemotherapy is prevented. Likewise, for the treatment of radiation-induced dermatitis, the chemoprotective amine can be further formulated as a gel, ointment or cream containing moisturizers. This would further protect the epidermis from radiation damage. Administration of topical formulations comprising longer polyamines preferably is initiated several days prior to the cancer therapy, to ensure that the epithelial and mucosal cells are adequately treated. For smaller compounds, topical application may be initiated as late as 30 minutes prior to cancer therapy, or at intermediate times prior to therapy, e.g., 2 hours, 4 hours, or incrementally up to 18-24 hours, prior to therapy. The formulation may then continue to be applied during the course of chemotherapy.

In connection with the treatment of alopecia, and particularly radio- or chemotherapy-induced alopecia, the pharmaceutical preparations of the invention may further comprise, or may be coadminstered with, a vasoconstrictor. Pharmaceutically-acceptable vasoconstrictors are known to the skilled artisan. Exemplary vasoconstrictors presently preferred for use for treatment of alopecia according the present methods include epinephrine, capoten, enalapril, lisinopril, zolmitriptan, tetrahydrozaline, phenylephrine, procainimide, and nitric oxide. Epinephrine is presently preferred as a vasoconstrictor for use herein. The use of epinephrine as a topical vasoconstrictor used in conjunction with exemplary compounds of the invention is shown in the examples. Vasoconstrictors appear to be able to potentiate the effect of the aminothiols and other compounds disclosed herein by Vasoconstrictor can provide a benefit by any one of several means. For example, without limiting the invention to any one theory of operation, vasoconstrictors may act by:

1) constricting skin blood vessels, thereby reducing systemic absorption of topically applied aminothiol; thus reducing any potential systemic toxicity;
2) constricting skin blood vessels, thereby increasing or maintaining the effective amount and time that an active compound, e.g. an aminothiol is present at the site of action, thus increasing efficacy;
3) at least transiently constricting skin blood vessels, thereby reducing the amount of systemic chemotherapy arriving at epidermal and follicular matrix stem cells; and
4) at least transiently constricting skin blood vessels thereby reducing the amount of oxygenated blood arriving at epidermal and follicular matrix stem cells.

The use of vasoconstrictors as described herein may include topical application of the vasoconstrictor before, during (e.g at the time of), or following the application of the pharmaceutical preparation or composition comprising the aminothiol or other active compound. For the treatment of alopecia, the topical application of epinephrine is preferred. Most preferred is the application of the vasoconstrictor just prior to or in conjunction with the application of the aminothiol, to allow any benefits of transient constriction of the blood vessels to accrue to the patient. In one embodiment, the application of the vasoconstrictor is repeated during the treatment with the active compound. Presently preferred are vasoconstrictors which increase the efficacy of the aminothiol or other active compound in terms of treatment of, for example, the alopecia.

For protection of the gastrointestinal epithelium, the chemoprotective amine is formulated to be delivered by mouth to a patient prior to scheduled administration of cancer therapy. Administration of the protective formulation in the 1-5 days prior to radiotherapy or the infusion of the chemotherapeutic agent thus confers protection to susceptible mucosal epithelial cells. For example, the patient would be instructed to consume a "shake" containing the chemoprotective amine in an orally acceptable solution or liposome emulsion before breakfast in the morning, in the 1-5 days preceding chemotherapy. This would allow the chemoprotective amine to be present when the chemotherapy drugs or radiotherapy act on the GI mucosal epithelium.

The examples that follow are included to aid in a more complete understanding of the present invention. The examples do not limit the invention disclosed and claimed herein in any fashion. Reference numerals are to the reaction schemes described above. All purification columns were carried out using silica gel (230-400 mesh) with eluant noted. Silica gel plates (250 micron) were used for all thin layer chromatography (TLC) with the appropriate solvent system noted.

EXAMPLE 1

Preparation of Compounds Used in Synthetic Schemes

Scheme 1:

Compound 2: 2 M ethylamine (compound 1) in tetrahydrofuran was stirred in a pressure bottle at <0° C. and mesitylene sulfonyl chloride (3 molar equivalents wrt ethylamine) was added in portions so that the temperature did not exceed 10° C. Dichloromethane and triethylamine were added and the pressure bottle sealed. The reaction was stirred in a 30° C. water bath for one hour and at RT for 30 minutes. The reaction progress was monitored by TLC using 8:2 heptanes: ethyl acetate as the mobile phase. Water was added and the organic layer was separated, the water layer was extracted once with dichloromethane, the combined organic layers were washed twice with water and condensed under vacuum. The product was used without further purification.

Compound 3: NaH (1.2 molar equivalents wrt compound A) was stirred, under $N_2$, at 10° C. and dimethylformamide was added. Compound 2 dissolved in tetrahydrofuran was added and stirred until the evolution of $H_2$ gas ceased. Bromobutyl (or any N-alkyl depending on desired distance between amines)-phthalimide (1.1 molar equivalents wrt to compound 2) was added in one portion and NaI was added. The reaction was heated to 60° C. and the progress monitored after several hours by TLC using 7:3 heptanes: ethyl acetate as the mobile phase. The reaction contents were condensed under vacuum and dissolved in ethyl acetate and water. The organic layer was separated, the aqueous layer was extracted with ethyl acetate, and the combined organic layers were washed with dilute brine and condensed under vacuum. The product was used without further purification.

Compound 4: Ethanol was heated to 70° C. and compound B dissolved in hot ethanol was added. Hydrazine hydrate (2.5 molar equivalents wrt compound 3) was added all at once and the reaction was stirred at 70° C. overnight. The reaction progress was monitored by TLC using 6:4 heptanes: ethyl acetate as the mobile phase. The completed reaction was cooled on ice and a white precipitate formed. The precipitate was removed by filtration and the filtrate condensed under vacuum. The resulting semisolid was dissolved in dichloromethane and water. The organic layer was separated, the aqueous layer was extracted with dichloromethane and the combined organic layers were washed with water and condensed under vacuum. The product was purified by column chromatography using silica gel and 90:9:1 dichloromethane: methanol: ammonium hydroxide as the eluant.

Compound 5: Mesitylene sulfonyl chloride (1.1 molar equivalents wrt compound 4) dissolved in dichloromethane was stirred, under $N_2$, at 10° C. Compound C dissolved in dichloromethane was slowly added so that the temperature did not exceed 15° C. The reaction was cooled to 10° C. and triethylamine (1.2 molar equivalents wrt compound 4) was added. The reaction was stirred at RT for several hours. The progress was monitored by TLC using 1:1 heptanes: ethyl acetate as the mobile phase. The reaction was quenched by adding water and stirring for 20 minutes. The organic layer was separated, the aqueous layer was extracted with ethyl acetate then dichloromethane, and the combined organic layers were washed with water and condensed under vacuum. The product was purified by column chromatography using silica gel and 6:4 heptanes: ethyl acetate as the eluant.

The polyamine side chains are elongated by repeating steps 2-4 until the desired length is reached.

Scheme 2:

Compound 16: Dihydroxyacetone dimer, compound 15, was stirred in dimethylformamide, under $N_2$, at 2° C. Imidazole (5.02 molar equivalents wrt. Compound 15) then tert-butyl dimethylsilyl chloride (4.99 molar equivalents wrt compound 15) were added. The reaction was stirred at RT for 2 hours. Ice water was added and the reaction stirred for 20 minutes. The organic layer was separated, the aqueous layer extracted two times with ethyl acetate, the combined organic fractions were washed with dilute brine, dried over anhydrous MgSO4, filtered, and condensed under vacuum to yield brown oil. The oil was purified by column chromatography using silica gel and 97:3 heptanes: ethyl acetate then 95:5 heptanes: ethyl acetate as the eluant.

Compound 17: NaH (1.1 molar equivalents wrt compound 1) was stirred, under $N_2$, in an ice bath and toluene was added. Triethyl phosphonoacetate (1.01 molar equivalents wrt compound 16) was slowly added so that the temperature did not exceed 10° C. The reaction was stirred on ice until all observed effervescence stopped. The reaction was removed from the ice bath and compound 16 (bis-OTBS acetone) was added drop-wise. The reaction was stirred at RT for 1.5 hours and ethanol was added to dissolve a precipitate that had formed. Water was added to quench the reaction. The organic layer was separated, the aqueous layer extracted once with ethyl acetate, and the combined organic layers were washed with brine and dried over anhydrous $MgSO_4$. The organic solution was filtered and condensed under vacuum to yield yellow oil. The oil was purified by column chromatography using silica gel and 98:2 heptanes: ethyl acetate.

Compound 18: Compound 2 was stirred in ether and cooled, under $N_2$, to −80° C. in an acetone/dry ice bath. Diisobutyl aluminum hydride (1.5 molar equivalents wrt compound 17) was added drop wise. The reaction was removed from the acetone/dry ice bath, warmed to RT, and stirred at RT for 50 minutes. The reaction was cooled in an acetone/dry ice bath and water was added drop wise to quench the reaction. The acetone/dry ice bath was removed and 20% NaOH (molar equivalents wrt compound 17), dichloromethane, and Rochelle salt (KNa tartrate tetrahydrate) were added. The organic layer was separated, the aqueous layer extracted two times with dichloromethane, and the organic fractions were combined, washed with water and dried first with $K_2CO_3$ and then $MgSO_4$. The dried organics were filtered and condensed under vacuum to yield clear oil. The clear oil was purified by column chromatography using silica gel and 9:1 heptanes: ethyl acetate as the initial eluant then changing to 8:2 heptanes: ethyl acetate.

Compound 19: Compound 18 was stirred in dichloromethane, under $N_2$, and cooled to below 0° C. in an acetone/ice bath. Triethylamine (1.2 molar equivalents wrt compound 18) was added and the reaction cooled to below 0° C. Methane sulfonyl chloride (1.3 molar equivalents wrt compound 18) was added slowly while monitoring the temperature to assure that it did not exceed 5° C. The reaction stirred cold for 1 hour then dichloromethane and water were added. The organic layer was separated, the aqueous layer extracted with dichloromethane, the combined organic layers were dried with $K_2CO_3$ and $MgSO_4$, filtered and condensed under vacuum to yield the mesylate intermediate. The product was used without further purification.

Compound 20: NaH (1.25 molar equivalents wrt compound 18) was stirred with dimethyl formamide, under $N_2$, and a polyamine side chain (1.15 molar equivalents wrt compound 18), of chosen length, dissolved in tetrahydrofuran was slowly added. The reaction stirred at RT until the evolution of $H_2$ gas ceased. Starting material mesylate was slowly added (compound 4, step 1 product) and stirred at RT for several hours. Upon completion, as evidenced by TLC, the reaction contents were condensed under vacuum. The crude semi-solid was dissolved in ethyl acetate and water. The organic layer was separated; the aqueous layer extracted twice with ethyl acetate, the combined organic layers were washed with water and condensed under vacuum. The product was purified by column chromatography using silica gel and 75:25 heptanes: ethyl acetate as the eluant.

Compound 21: Compound 20 was stirred in methanol at RT. Concentrated HCl (2 molar equivalents wrt compound 20) was slowly added. The reaction stirred at RT for 30 minutes or until reaction was complete as evidenced by TLC with 60:40 heptanes: ethyl acetate as the mobile phase. The reaction contents were condensed under vacuum and purified by column chromatography using silica gel and 95:5 dichloromethane: methanol as the eluant.

Compound 22: Compound 21 diol was stirred in dichloromethane, under $N_2$, in an ice/MeOH bath. Benzoyl Chloride (1.03 molar equivalents wrt compound 21) was added. Once the reaction reached <10° C., pyridine (1.04 molar equivalents wrt compound 21) was slowly added. The reaction was stirred in the ice/methanol bath for 1 hour and completeness was determined by TLC using 1:1 heptanes: ethyl acetate as the mobile phase. Once reaction was complete, water was added and the reaction stirred for 15 minutes in the ice/methanol bath. The organic layer was separated; the aqueous layer extracted with dichloromethane, the combined organic layers were washed once with water, dried over anhydrous $MgSO_4$, filtered and condensed under vacuum. The product was purified by column chromatography using silica gel and 7:3 heptanes: ethyl acetate as the eluant.

Compound 23: Compound 22 was stirred in toluene, under $N_2$, at <5° C. Phosphorus tribromide (1.1 molar equivalents wrt compound 22) was slowly added. The reaction was removed from the ice bath and stirred at RT for 30 minutes or until the reaction was complete as determined by TLC using 95:5 dichloromethane: methanol as the mobile phase. Upon completion the reaction was returned to the ice bath, water was slowly added, and the reaction was stirred for 15 minutes. The organic layer was separated, the aqueous layer extracted two times with ethyl acetate, the combined organic layers were washed with 2% (w:v) NaHCO3 and then brine, dried over $K_2CO_3$ and $MgSO_4$, filtered and condensed under vacuum. The product was used without further purification.

Compound 24: NaH (1.2 molar equivalents wrt compound 23) was stirred in dimethyl formamide, under $N_2$, at RT and a polyamine side chain (1.2 molar equivalents wrt compound 23), of chosen length, dissolved in tetrahydrofuran was added slowly. The reaction stirred at RT until the evolution of $H_2$ gas ceased. Compound 23, dissolved in tetrahydrofuran, was slowly added and the reaction was stirred at RT for several hours. Reaction completeness was determined by TLC using 80:20 toluene: ethyl acetate as the mobile phase. The reaction was condensed under vacuum; the crude was dissolved in ethyl acetate and water. The organic layer was separated, the aqueous layer was extracted with ethyl acetate, and the combined organic layers were washed with brine, and condensed under vacuum. The product was used without further purification.

Compound 25: Compound 24 was stirred in tetrahydrofuran, under $N_2$, at RT. Methanol then sodium methoxide (1.5 molar equivalents wrt compound 24) were added and the reaction was stirred at RT for 30 minutes. Reaction completeness was determined by TLC using 80:20 toluene: ethyl acetate as the mobile phase. Concentrated HCl (molar equivalents wrt sodium methoxide) was added to neutralize the sodium methoxide and the reaction contents were condensed under vacuum. Ethyl acetate and water were added to the crude product. The organic layer was separated, the aqueous layer washed once with ethyl acetate and once with dichloromethane, the combined organic layers dried with $NaSO_4$, filtered and condensed under vacuum. The product was purified by column chromatography using silica gel and 8:2 toluene: ethyl acetate as the eluant.

Scheme 3:

Compound 28: Compound 26 was stirred in dichloromethane, under $N_2$, at −10° C. in an ice/methanol bath. Triethylamine (2 molar equivalents wrt to compound 26) was added and the reaction was again cooled to −10° C. Methane sulfonyl chloride (2.5 molar equivalents wrt compound 26) dissolved in methylene chloride was added slowly and the reaction stirred cold for 1 hour. Reaction completeness is monitored by TLC using 8:2 heptanes: ethyl acetate. Water was slowly added to quench the reaction. The organic layer was separated, the water layer extracted with dichloromethane, the combined organic layers were washed with brine and condensed under vacuum. The reactive intermediate was used immediately without further purification.

Compound 29: Potassium thioacetate (2.5 molar equivalents wrt compound 26) in dimethylformamide was stirred, under $N_2$, at RT. Compound 28 mesylate in dimethylformamide was slowly added and the reaction was stirred overnight. The reaction was condensed under vacuum and the solids dissolved in ethyl acetate and water. The organic layer was separated, the aqueous layer back extracted with ethyl acetate, the combined organic layers were washed with brine and condensed under vacuum. The product was purified by column chromatography using silica gel and 8:2 toluene: ethyl acetate as the eluant.

Compound 31: NaH (1.25 molar equivalents wrt compound 26) was stirred, under $N_2$, at RT and dimethylformamide was added. Mesitylene methyl sulfonamide dissolved in tetrahydrofuran was slowly added and the reaction was stirred until the evolution of $H_2$ gas ceased. Compound 28 mesylate dissolved in tetrahydrofuran was slowly added and the reaction was stirred overnight. The reaction was condensed under vacuum and the solids dissolved in ethyl acetate and water. The organic layer was separated, the aqueous layer extracted with ethyl acetate, the combined organic layers were washed with brine and condensed under vacuum. The product was purified by column chromatography using silica gel and 8:2 toluene: ethyl acetate as the eluant.

Compound 33: NaH (1.25 molar equivalents wrt compound 26) was stirred, under $N_2$, at RT and dimethylformamide was added. Mesitylene dimethyl sulfonamide dissolved in tetrahydrofuran was slowly added and the reaction stirred until the evolution of $H_2$ gas ceased. Compound 28 mesylate dissolved in tetrahydrofuran was slowly added and the reaction was stirred overnight. The reaction was condensed under vacuum and the solids dissolved in ethyl acetate and water. The organic layer was separated, the aqueous layer extracted with ethyl acetate, the combined organic layers were washed with brine and condensed under vacuum. The product was purified by column chromatography using silica gel and 8:2 toluene: ethyl acetate as the eluant.

Compound 35: NaH (1.25 molar equivalents wrt compound 26) was stirred, under $N_2$, at RT and dimethylformamide was added. Mesitylene ethyl sulfonamide dissolved in tetrahydrofuran was slowly added and the reaction stirred until the evolution of H2 gas ceased. Compound 28 mesylate dissolved in tetrahydrofuran was slowly added and the reaction stirred overnight. The reaction was condensed under vacuum and the solids dissolved in ethyl acetate and water. The organic layer was separated, the aqueous layer extracted with ethyl acetate, the combined organic layers were washed with brine and condensed under vacuum. The product was purified by column chromatography using silica gel and 8:2 toluene: ethyl acetate as the eluant.

Removal of Mesitylene Protective Groups:

Compounds 30, 32, 34, and 36: Starting material was stirred in dichloromethane at RT and phenol (11 molar equivalents per mesitylene group) was added. 30% HBr in acetic acid was slowly added (13 molar equivalents per mesitylene group) and the reaction was tightly sealed and stirred for 24-72 hours at RT. Water was added and the reaction stirred for 30 minutes at RT. The organic layer was separated, the aqueous layer was washed five times with dichloromethane, and the water layer was condensed under vacuum. 30% NaOH was added to the oil and stirred for several minutes to make the free base. Dichloromethane was added and stirred for several more minutes. The organic layer was separated, the water layer was extracted five times with dichloromethane, and the combined organic layers were condensed under vacuum. The HCl salt was made by stirring the free base in ethanol and slowly adding concentrated HCl (4 molar equivalents per free amine). The reaction was condensed under vacuum and the solids were recrystallized in a hot ethanol/water mixture.

Scheme 16:

Compound 83: Potassium phthalimide (2.4 molar eqivalents wrt to 37) was dissolved in 3 volumes of anhydrous DMF. Compound 37 was then added, and the reaction stirred for 16 to 24 hours at RT. The reaction material was concentrated down to an oily semi-solid, and then water and methylene chloride were added to the mixture. The layers were separated and the aqueous was back-extracted with methylene chloride. The organics were combined, washed with brine, and then concentrated down to solids. The solids were stirred in hot isopropanol, allowed to cool to RT, then filtered. The crude solids were dried to give compound 83 as an off-white solid.

Compound 84: Compound 83 was dissolved in 10 volumes of warm (ca. 60° C.) ethanol. Hydrazine hydrate (1.1 molar equivalents wrt 83) was added, and the reaction stirred warm for 4 hours. The reaction was cooled in an ice bath to <5° C., concentrated hydrochloric acid (2.5 molar equivalents wrt 83) was added, and the mixture was stirred for 30 minutes. The cold mixture was filtered, and then concentrated. Ethanol was added to the solids, heated to reflux, and the material was cooled to RT. The crude crystalline product was filtered and dried to give compound 84.

Compound 85: Compound 84 was dissolved into 15 volumes of chilled (<5° C.) 10% NaOH(aq). Mesitylenesulfonyl chloride (1.1 equivalents wrt 84) in methylene chloride (a volume equal to the amount of aqueous) was slowly added, and the reaction stirred for 1 hour while chilled. The reaction then was allowed to warm to RT and stir for 16 hours. The layers were separated and the aqueous back-extracted with methylene chloride. The organics were combined, washed with brine, and then concentrated down to solids. The crude product was recrystallized from 5 volumes of isopropanol to give compound 85.

Compound 86: Compound 85 was dissolved in 6 volumes of anhydrous THF and chilled to <5° C. 1 M borane-THF complex in THF (2 molar equivalents wrt 85) was slowly added and the reaction was stirred cold for 30 minutes. The reaction then warmed to RT while stirring for 16 hours. Ethanol (2.5 volumes wrt 85) was slowly added as off-gassing and exotherm allowed, followed by 4 M NaOH(aq) (6.5 volumes wrt 85), and finally 30% hydrogen peroxide (5.5 volumes wrt 85). The reaction then stirred for 16 hours. Ethyl acetate was added and the layers separated. The organics were washed with brine and concentrated to an opaque white oil. The oil was chromatographed on silica gel (10:1 loading) using 6:4 heptanes: ethyl acetate as the eluent. Positive fractions were combined and concentrated to give pure compound 86.

Compound 87: Compound 86 was dissolved in 10 volumes of methylene chloride, chilled to <5° C., and triethylamine (3 molar equivalents wrt 86) was added. Methanesulfonyl chloride (2 molar equivalents wrt 86) in methylene chloride (5 volumes wrt 86) was slowly added and the reaction stirred cold for 1 hour. Water was added, and the reaction stirred for 15 minutes. The layers are separated and the aqueous back-extracted with methylene chloride. The organics were combined, washed with brine, and then concentrated to a pale-yellow oil. The crude oil was chromatographed on silica gel using 4:1 toluene: ethyl acetate. Positive fractions were combined and concentrated to give compound 87.

Compound 88: Compound 87 was dissolved in 10 volumes of anhydrous DMF. Potassium thioacetate (2.5 molar equivalents wrt 87) dissolved in anhydrous DMF (an equal volume used to dissolve 87) was added, and the reaction stirred at RT for ca. 16 hours. The solvent was removed by rotary evaporation and the oily semi-solid dissolved in methylene chloride and water. The layers were separated and the aqueous back-extracted with methylene chloride. The organics were combined and washed with brine. The organics were concentrated and dissolved in hot isopropanol. The inorganic salts were filtered away, and the product crystallized. Compound 88 was isolated as white crystalline material.

Scheme 17:

Compound 91: Methylamine hydrochloride (compound 90, 1.5 molar equivalents wrt mesitylenesulfonyl chloride) was dissolved into 15 volumes of chilled (<5° C.) 10% NaOH(aq). Mesitylenesulfonyl chloride in methylene chloride (a volume equal to the amount of aqueous) was slowly added, and the reaction stirred for 1 hour while chilled. The reaction then was allowed to warm to RT and stir for 16 hours. The layers were separated and the aqueous back-extracted with methylene chloride. The organics were combined, washed with brine, and then concentrated down to solids. The crude product was recrystallized from 5 volumes of isopropanol to give compound 91.

Compound 92: Sodium hydride (1.2 molar equivalents wrt compound 91) was stirred in anhydrous dimethylformamide, under N2, at RT and compound 91 (1.1 molar equivalents wrt compound 37) dissolved in anhydrous tetrahydrofuran was added slowly. The reaction stirred at RT until the evolution of H2 gas ceased. Compound 37, dissolved in tetrahydrofuran, was slowly added and the reaction was stirred at RT for several hours. Upon reaction completion, a small amount of water was added, and the reaction concentrated to a thick oily semi-solid. Water is added, and the crude product is collected by filtration. The solids (compound 92) are dried and then recrystallized from ethyl acetate.

Compound 93: Compound 92 was dissolved in 6 volumes of anhydrous THF and chilled to <5° C. 1 M borane-THF complex in THF (2 molar equivalents wrt 92) was slowly added and the reaction was stirred cold for 30 minutes. The reaction then warmed to RT while stirring for 16 hours. Ethanol (2.5 volumes wrt 92) was slowly added as off-gassing and exotherm allowed, followed by 4 M NaOH(aq) (6.5 volumes wrt 92), and finally 30% hydrogen peroxide (5.5 volumes wrt 92). The reaction then stirred for 16 hours. Ethyl acetate was added and the layers separated. The organics were washed with brine and concentrated to an opaque white oil. The oil was chromatographed on silica gel (10:1 loading) using 6:4 heptanes:ethyl acetate as the eluent. Positive fractions were combined and concentrated to give pure compound 93.

Compound 94: Compound 93 was dissolved in 10 volumes of methylene chloride, chilled to <5° C., and triethylamine (3 molar equivalents wrt 93) was added. Methanesulfonyl chloride (2 molar equivalents wrt 93) in methylene chloride (5 volumes wrt 86) was slowly added and the reaction stirred cold for 1 hour. Water was added, and the reaction stirred for 15 minutes. The layers are separated and the aqueous back-extracted with methylene chloride. The organics were combined, washed with brine, and then concentrated to a pale-yellow oil. The crude oil was chromatographed on silica gel using 4:1 toluene: ethyl acetate. Positive fractions were combined and concentrated to give compound 94.

Compound 95: Compound 94 was dissolved in 10 volumes of anhydrous DMF. Potassium thioacetate (2.5 molar equivalents wrt 94) dissolved in anhydrous DMF (an equal volume used to dissolve 94) was added, and the reaction stirred at RT for ca. 16 hours. The solvent was removed by rotary evaporation and the oily semi-solid dissolved in methylene chloride and water. The layers were separated and the aqueous back-extracted with methylene chloride. The organics were combined and washed with brine. The organics were concentrated and dissolved in hot isopropanol. The inorganic salts were filtered away, and the product crystallized. Compound 95 was isolated as white crystalline material.

EXAMPLE 2

Biological Assay for Efficacy in Preventing Alopecia

The efficacy of chemoprotective polyamines and aminothiols in reducing or preventing chemotherapy- or radiation-induced alopecia in a rat model was examined. This animal model mimics many of the features found in chemotherapy-induced alopecia in humans. It is particularly useful for testing and optimizing novel therapeutics.

Induction of alopecia by cytoxan (CTX). Lactating Sprague Dawley mother rats with rat pups were purchased from Harlan Sprague Dawley (Indianapolis, Ind.). The mother rats were given food and water ad libitum. The rats pups were tested in the model of chemotherapy-induced alopecia described by Hussein A. M. et al., Science: 249, 1564 (1990). Cytoxan (CTX), a chemotherapeutic widely used in the treatment of cancer, was used to induce alopecia in the rats. A common side effect of cytoxan treatment in patients is alopecia. Lyophilized vials of Cytoxan were obtained from Mead-Johnson. To produce CTX-induced alopecia, 11 day old rat pups, which are at the peak of coat growth, were injected i.p. with 30-35 μg of CTX/gm body weight. CTX was dissolved in water. By day 18 of life, the animals have shed virtually 100% of their coat leaving bare skin on their backs. Thus, topical application of protective drugs to the animal's back prior to the CTX insult provides a suitable test for prevention of chemotherapy-induced alopecia. A separate alopecia assay was also developed in which whole-body irradiation on day 11 of life was used as the insult. This assay is described in further detail in Example 12 which follows.

In the earliest studies with chemoprotective polyamines, the molecules were prepared in a topical delivery vehicle consisting of from 50-70% ethanol in water, depending on the solubility of the compound. The compounds in ethanol/water solution from 50-150 □l in volume were topically administered to the backs of the pups once per day before and after CTX challenge. Using a micropipette, the formulation was applied to an approximately 2 cm2 section of skin on the backs of the rat pups. Specifically, the pups were treated once daily for the 4-5 days before CTX challenge, once on the day of CTX challenge and once daily for 5 days afterwards. Control groups consisted of pups receiving only delivery vehicle. Control groups treated with delivery vehicle were tested as part of every treatment study. Three or more animals were tested per group in both the control and test groups. In the later studies exploring the efficacy of aminothiols in preventing alopecia, animals generally received 4-6 topical applications to the back prior to the chemotherapy or radiation insult, and the vehicle was generally composed of an ethanol:propylene glycol:water mixture.

In the earliest studies with chemoprotective polyamines, hair loss was evaluated using a modified alopecia-scoring index described by Chen G. et al., Int. J. Cancer: 75, 303 (1998). A score of 0=no hair loss; a score of 1=10-30% hair loss; a score of 2=40-60% hair loss; a score of 3=70-90% hair loss; and a score of 4=100% hair loss. In the later studies with aminothiols a simpler scoring scale was adopted in which coat density was scored on a 0-100 scale as "% of normal coat density."

EXAMPLE 3

Biological Assay for Efficacy in Preventing Dermatitis

To determine efficacy of chemoprotective polyamines in preventing radiation-induced dermatitis, adult rats were topically treated with the compounds before and after radiation treatment. Rats were exposed to medically relevant levels of radiation that could induce clinical radiation dermatitis. Sprague Dawley rats (Harlan Spraque Dawley) at 4-6 weeks-old were anesthetized with sodium pentobarbital at 40 mg/kg body weight (Sigma, St. Louis, Mo.) prior to radiation exposure. A defined area (1.5×2 cm) on the backs of rats was irradiated using a Mark I, Model 30, Cs 137 irradiator (J. L. Sheppard & Associates). Before topical drug treatment or irradiation, the backs of the rats were clipped using an Oster clipper at the closest setting. The rest of the body was protected from radiation exposure using a lead shield (2.5 cm thick). A dose response study was initially performed to reproduce relevant dermatitis that matched the Grade (I-IV) scale used to score the severity of radiation-induced dermatitis in humans. The severity of the dermatitis was scored 12-13 days post-irradiation at the peak of the dermal inflammation. Radiation doses of 4-5 Gray (1 Gray (Gy)=100 mrem) produced Grade I dermatitis while radiation doses of 6-7 Gy produced Grade II dermatitis. More severe radiation dermatitis was produced at 8-10 Gy (Grade III dermatitis) or at 11-13 Gy (Grade IV). Radiation dermatitis of Grade II-III was considered most clinically relevant, so a radiation dose of 8.7 Gy was typically used in the rats. The clipped back region on the rats was treated topically with aminothiol in delivery vehicle four times in the two hours immediately preceding irradiation (at −2 hr, −1 hr, −30 min, and −10 min; irradiation was at 0 min The polyamines or amino thiols were prepared in a delivery vehicle, consisting of ethanol:propylene glycol: water, ranging from 0:95:5 to 50:30:20 depending upon the solubility characteristics of the topical molecule, and the degree of dermal penetration desired. A vehicle composed of an emulsion formed by sonication of 'nonionic liposomes' and isopropyl myristate was also used (Jayaraman, S. et al., *J. Pharm. Sci.* 85:1082-1084, 1996). In a commonly used protocol, 220 µl of topical drug/vehicle was applied to an area ~2 cm×3 cm on the back in the 2 hr just prior to irradiation. Rats treated with only the delivery vehicle served as controls. Twelve to thirteen days post-radiation, the rats were evaluated for dermatitis within the irradiated area. In early studies, a modified scoring scale described by Masuda K. et al., *Int. J. Radiation Oncol. Biol. Phys*: 12, 1645 (1986) was used, and in later studies, including those described here, a simplified scoring system was used in which the percentage of the irradiated, rectangular field covered with scrab material was estimated between 0 and 100% to provide scores on a scale between 0 and 100.

EXAMPLE 4

Radiation-Induced Mucositis Model in Hamsters

The model for radiation-induced oral mucositis was developed for the purpose of screening and identifying effective polyamines and aminothiols useful for treatment. The model used in this example was derived from the oral mucositis model described by Alvarez et al. (*Clin. Cancer Research* 9:3454-3461, 2003). Male golden Syrian hamsters (70-95 gram, Charles River Laboratories, Wilmington, Mass.) were used. Animals were individually numbered, housed in small groups and fed and watered ad libitum. Hamsters were anesthetized with sodium pentobarbital (80 mg/kg body weight, Sigma, St. Louis, Mo.). The left buccal cheek pouch was everted and secured. A protective lead shield covered the remainder of the animal. Subsequently, the cheek pouch was irradiated with a single dose of radiation from 20 to 40 Gy delivered to the targeted mucosa in the $^{137}$Cs irradiator. Starting 10 to 12 days after radiation, the severity of mucositis was assessed every two days. The severity level of mucositis was evaluated using a modified mucositis scoring system described by Sonis S. T. et al. (*Oral Oncology* 36:373-381, 2000)

The scoring system was as follows:
0=Pouch completely healthy. No erythema or vasodilatation.
1=Erythema.
2=Severe erythema, vasodilatation
3=Severe erythema/vasodilatation. Superficial erosion on radiated pouch surface area.
4=Formation of ulcers in one or more places. Cumulative ulcer formation about up to 50% of radiated pouch surface area. Diminished pliability of mucosa
5=More then 50% ulceration of the radiated pouch mucosa. Loss of pliability.

Manifestations of radiation-induced mucositis were observed by day 12. The hamster buccal pouches were evaluated for the presence of mucositis and photographed every two days from day 12 to day 20. Mucositis was found to increase in severity, reaching a peak at day 16. An obvious dose response of radiation was seen, and the grades of mucositis at day 16 were scored as follows:

| Treatment | Mucositis Grade* |
|---|---|
| 0 Gy | 0 |
| 10 Gy | 1 |
| 20 Gy | 2 |
| 30 Gy | 2.5 |
| 40 Gy | 4 |
| 50 Gy | 5 |

*0 = Pouch completely healthy - no erythema or vasodilatation.
1 = Erythema.
2 = Severe erythema, vasodilatation.
3 = Severe erythema and vasodilatation; superficial erosion on radiated pouch surface area.
4 = Formation of ulcers in one or more places; culmulative ulcer formation about up to 50% of radiated pouch surface area; diminished pliability of mucosa.
5 = More than 50% or complete ulceration of the radiated pouch mucosa; loss of pliability.

EXAMPLE 5

Amino Thiol-Conferred Protection to Human Skin Cells in Tissue Culture

An in vitro cell culture assay was developed to determine the ability of chemoprotective polyamines, chemoprotective amino thiols and other molecules to confer radioprotection or chemoprotection to human skin cells. Diploid, human foreskin fibroblasts (23SK cells) were maintained in DMEM supplemented with 20% fetal bovine serum and gentamycin.

For toxicity experiments, cells were seeded at a density of 750 cells/100 µl of DMEM+20% FBS+gentamycin into each well of 96 well plates (Corning, Corning, N.Y.). The next day, solutions of protective drug molecules, typically at a 4 mM concentration, were prepared in Dulbecco's phosphate-buffered saline (D-PBS); each stock was titrated back to pH 7.0-7.5, if necessary, using sterile HCl or NaOH. Media was aspirated from cell wells, wells were rinsed with D-PBS, and loading solutions were then added to wells. Cells were typically exposed to loading solutions for 30 min. Following this drug loading period, plates were either placed directly into a Shepherd Mark II $Cs^{137}$ irradiator for irradiation (38 min), or wells were aspirated and the solution immediately replaced with a solution of D-PBS containing 350 µM phosphoramide mustard (obtained from NCI Chemical Repository) for a 40 min incubation at room temperature. After either treatment, wells were aspirated, rinsed and then given 100 µl of DMEM+20% FBS+gentamycin. Plates were maintained in 5% $CO_2$ within a humidified chamber within a humidified incubator for 4-5 days at 37° C. Twenty 1 of MTT solution (Promega Corp., Madison, Wis.) was then added to each well, and color development occurred over the next 3 hr at 37° C. Absorbance at 490 nm was then determined using a plate reader, and cell growth in treated wells compared to cell growth in wells loaded with vehicle and not irradiated or exposed to phosphoramide mustard was plotted using GraphPad software.

EXAMPLE 6

Evaluation of Efficacy of Amino Thiols in Preventing Radiation-Induced Dermatitis in a Rat Skin Model This example relates to the use of a rat skin model to evaluate the efficacy of two amino thiol compounds in preventing radiation-induced dermatitis. To test whether topically-applied aminothiols could prevent the radiodermatitis caused by external beam radiotherapy, the rodent model described in Example 3 was slightly modified. Briefly, the radiodermatitis model involved:
  i) shaving the backs of 6-7 week old rats or mice;
  ii) applying four topical doses of aminothiol in a delivery vehicle composed of ethanol:propylene glycol (PG): water in the 2 hr prior to irradiation;
  iii) irradiating a small, 3 cm² (1.5×2 cm) area on the animal's back (through a window in a lead plate) with 8.7 Gy of γ radiation from a $Cs^{137}$ source; and
  iv) scoring the severity of the dermatitis 12-13 days later, at the peak of the inflammatory skin reaction. Radiodermatitis severity was scored by estimating the percentage of the irradiated field that was covered by scrab material.

Figure 9A:
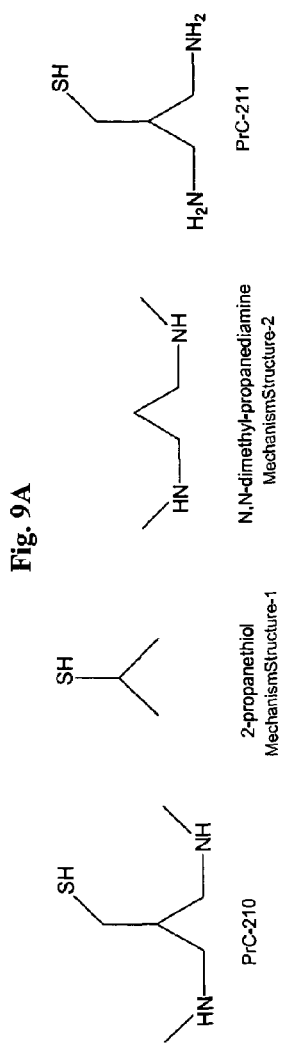
FIG. 9A illustrates the structures, as well as the structures of experimental intermediates.

The chemical structures of the PrC-210 and PrC-211 aminothiol compounds tested in this experiment are shown in FIG. 9*a*.

Figure 9B:
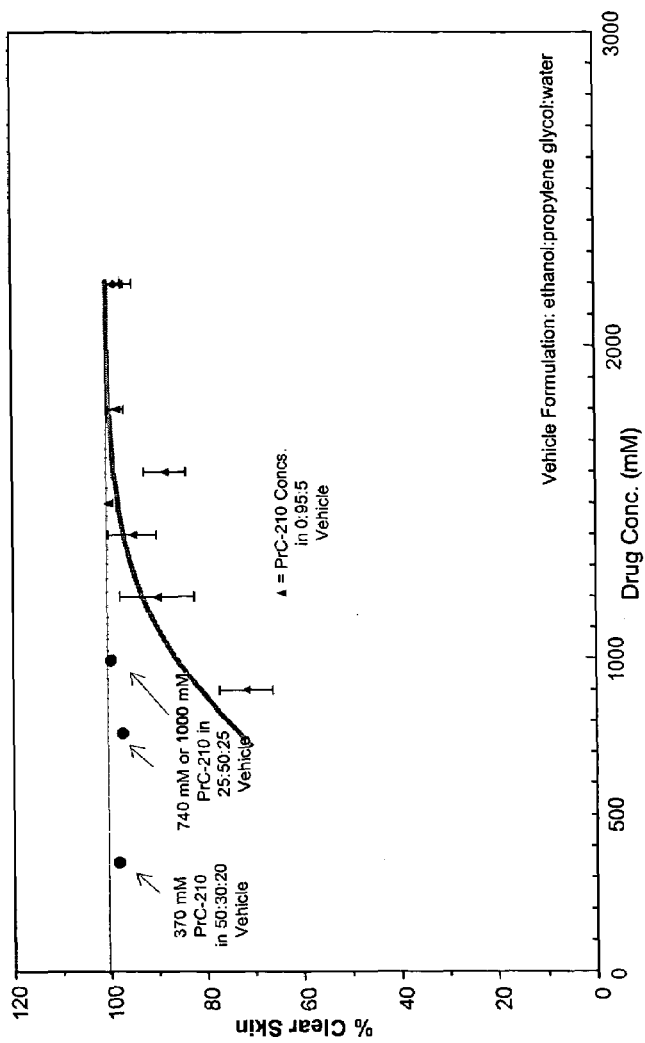
FIGS. 9B and C present data comparing the effects of increasing concentrations of test compounds on the percentage of clear skin, as an indication of the effectiveness of each in preventing radiation-induced dermatitis.
Figure 9D:
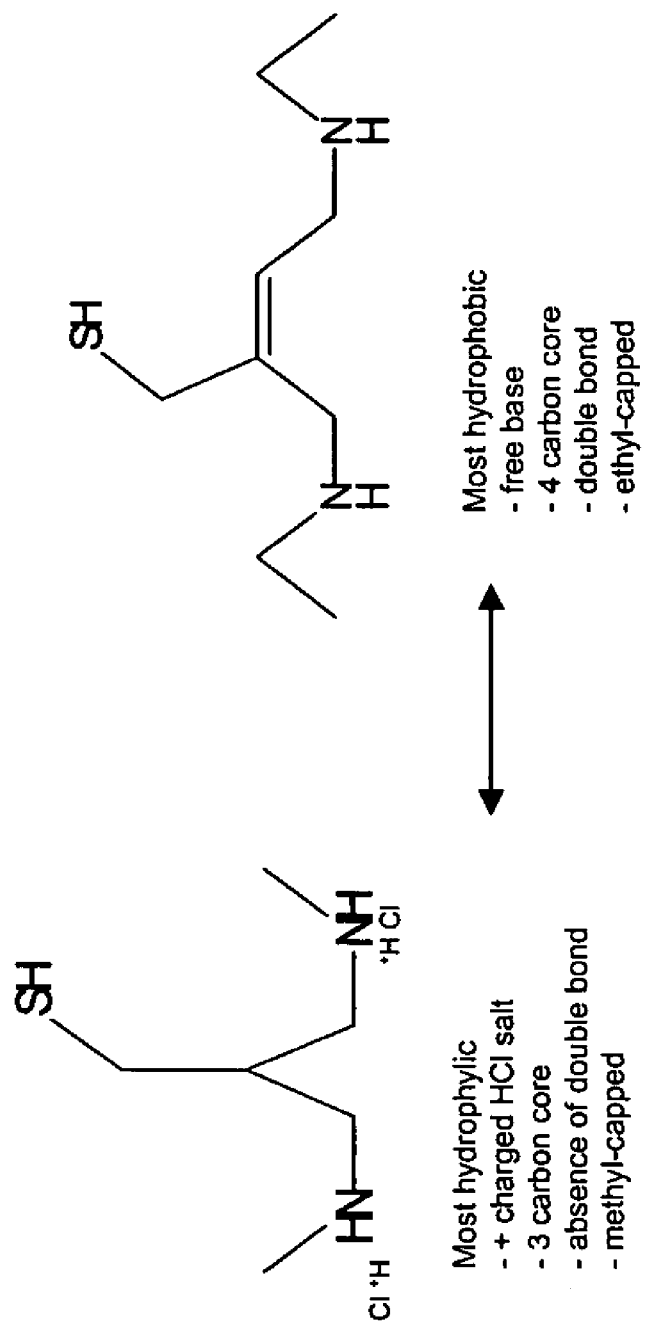
FIG. 9D illustrates some parameters relating to Pre-210 and 211.

The aminothiols PrC210 and 211 were dissolved in either 95:5 PG:water or 50:30:20 ethanol:PG:water. Results presented in FIGS. 9B and C (Drug conc vs % clear skin) indicate that concentrations of PrC-210 as low as 370 mM with accompanying total applied volumes of 105 ul (2.8 mg/cm² skin) could confer complete protection against radiation-induced dermatitis if it was delivered in a highly penetrating delivery vehicle (50:30:20; ethanol:PG:water). When the PrC-210 molecule was delivered using a 0:95:5 ethanol:PG:water vehicle, complete protection (100% Clear Skin) against radiodermatitis required a dose about 10 times higher (~24 mg/cm skin). Further results indicated that 1200-1500 mM PrC-210 in the 95:5 PG:water vehicle conferred complete protection. PrC-211 required a larger percentage of water to exert complete protection due to lower solubility. The vehicle for 1400 mM PrC-211 was 0:65:35 (ethanol:PG:water), and the water content was raised to 0:50:50 for 2200 mM PrC-211). FIG. 9D describes shows the structure of these two aminothiols. Parameters used in the design included fro example: capped amines to decrease catabolism; backbone length and DNA binding characteristics; "display" of nucleophile from flexible or rigid platforms; and overall molecule hydrophobicity for delivery.

An experiment was carried out to investigate whether two molecules (see FIG. 9A, Mechanism Structure 1 and Mechanism Structure 2), each comprising a single functional element within the PrC-210 molecule, exhibited protective activity in this system. Each molecule was dissolved at the same concentration (370 mM) and in the same delivery vehicle (50:30:20; ethanol:PG:water) as that used for PrC-210 and was then applied topically to animals using the same schedule as that used for PrC-210. The animals received the standard radiation dose of 8.7 Gy and were scored for dermatitis severity 13 days later. The results indicated that neither molecule exhibited discernable protective activity, suggesting that there may be a synergistic effect of the two functional elements in the single PrC-210 molecule that leads to its effects in protecting against development of radiation-induced dermatitis.

EXAMPLE 7

Evaluation of Candidate Compounds in Protection Against Mucositis in a Hamster Cheek Pouch Model This example relates to the use of a hamster cheek pouch model to evaluate the efficacy of PrC-210 and 211 in preventing radiation-induced mucositis. To test whether topically-applied aminothiols could prevent the mucositis caused by external beam radiotherapy, the hamster cheek pouch model was used essentially described in Example 4. Briefly, hamsters were anesthetized (Nembutal, 80 µg/gm b.w.), their left cheek pouch everted and any debris removed prior to re-positioning them in the mouth. Aliquots of 250 ul of a solution (vehicle=94% phosphate-buffered saline, 5% ethanol, 1% hydroxypropyl-methylcellulose) containing 50 mM to 2000 mM PrC-210 were then delivered to the cheek pouch which is enough to wet and distend the inside surface of the cheek pouch; after 30 min, the cheek pouch was everted, spread and immobilized on an inert disk (2 cm diameter) using small clips. The hamster and its immobilized cheek pouch were then positioned on a lead plate (2.5 cm thick) with the cheek pouch placed and secured over the hole (1.5 cm diameter) in the plate. The plate was placed in a $Cs^{137}$ irradiator (J. L. Shepherd) with the plate between the source and the hamster. Each animal was checked to see that it had normal, rhythmic breathing and that all visible tissues are red indicating normal oxygenation. After the cheek pouch was exposed for 10-20 min (17-34 Gy) to the source, the animal was returned to its cage. Sixteen days later, the animals were again anesthetized (60 ug/gm) with Nembutal, and the everted left cheek pouch was photographed, and then the everted right cheek pouch was photographed as a control. As part of scoring the radiation-induced damage to the left cheek pouch, a score was also assigned for the degree of erythema (0-5), the degree of edema (0-3), and the degree of tissue inflexibility (0-2), and scores for the right cheek pouch served as controls. Occasionally, both cheek pouches were also surgically removed and weighed to further assess radiation-induced edema.

Figure 10:
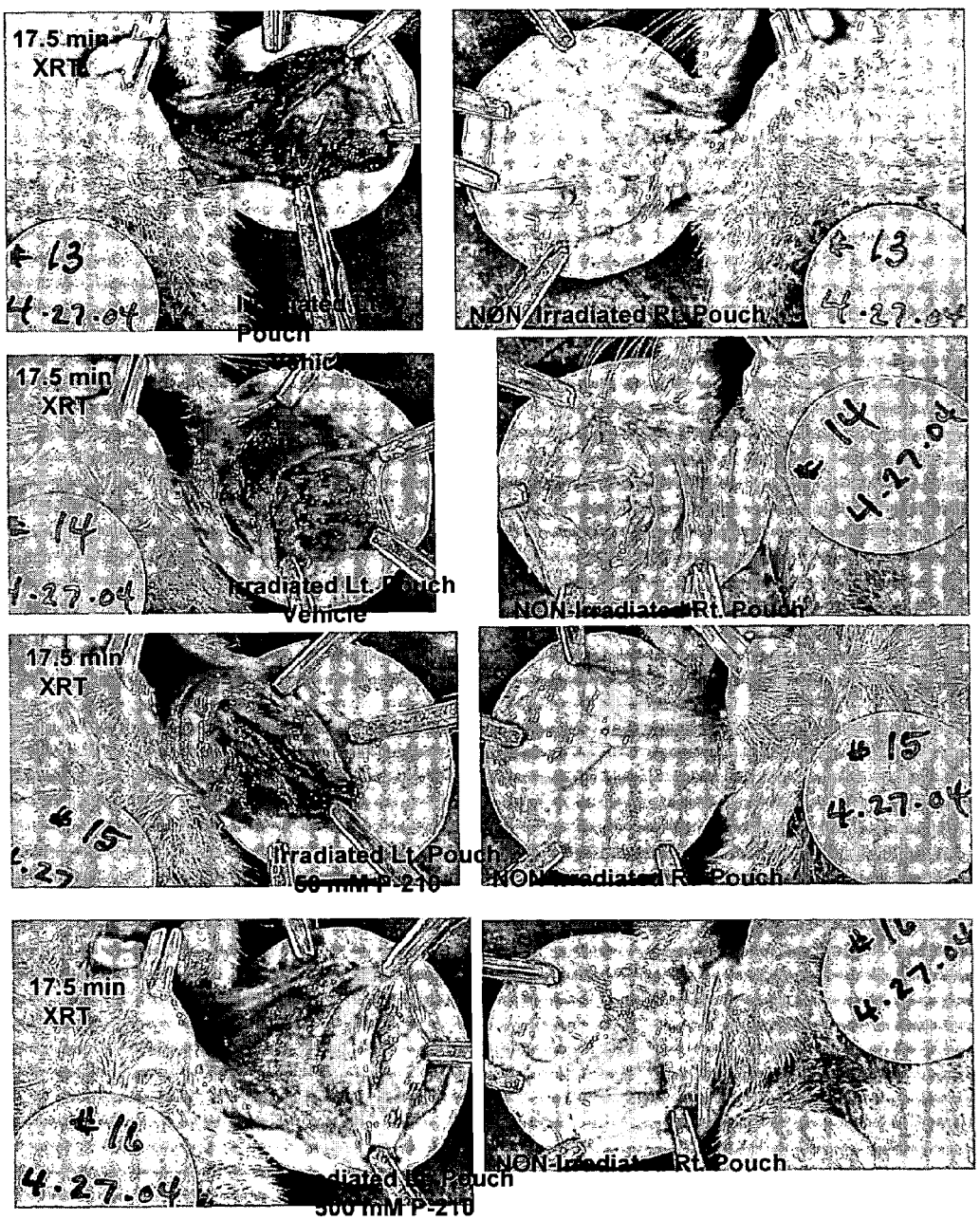
FIG. 10 presents photographs of treated and untreated hamster cheek pouches.

Photographs of treated and untreated hamster cheek pouches are presented in FIG. 10 and indicate that a 17.5 min exposure (30 Gy) of γ radiation causes a significant increase in erythema, edema and tissue inflexibitity in the mucosal tissue, which is not seen in the unirradiated right cheek pouch. Significantly, topical application of either 50 mM PrC-210 or 500 mM PrC-210 to the left cheek pouch for the 30 min before it was irradiated, resulted in a significant decrease in the erythema, swelling and inflexibility that was seen in the irradiated vehicle controls. These data suggest a general strategy for prevention of radiation-induced mucositis in which the mucosal tissue of a patient would be bathed continuously or recurrently with aminothiol in vehicle in the period just prior to radiotherapy. This could be accomplished by recurrently swishing an appropriate aminothiol solution in the mouth and/or by placing an aminothiol/vehicle-saturated sponge between the gum and cheek that would continuously dispense protective aminothiol in an appropriate vehicle to enable mucosal tissue uptake prior to irradiation.

EXAMPLE 8

Topical Aminothiol Treatment does not Interfere with the Efficacy of External Beam Radiotherapy or Systemic Chemotherapy This example presents results demonstrating that topical administration of PrC-210 does not interfere with the efficacy of the treatments whose adverse side effects it was designed to mitigate. Dosages up to a 5-fold excess of the typical protective topical regimen were tested and demonstrated to exert no effect on the efficacy of killing human cancer cells using external beam γ irradiation (6.2 Gy) or mouse leukemia cells using systemic chemotherapy (Cytoxan, 200 μg/g body weight).

Briefly, athymic nude mice (nu/nu, 6-7 weeks, Harlan Labs) were housed in cages containing autoclaved bedding and received autoclaved food and water. Cages were maintained in a sterile laminar flow hood. Mice received a single, sc injection of tumor cells (6.5×10$^6$, A431; 2.5×10$^6$, L1210) suspended in 200 ul of serum-free DMEM.

After three days, mice were treated with topical drug in vehicle or vehicle alone. PrC-210 was formulated in a 50:30:20 vehicle (ethanol:PG (propylene glycol):water, adjusted to pH 6.5 with NaOH), and mice received four topical applications over two hours (at −2 hr, −1 hr, −30 min and −10 min, irradiation was at 0 min). 18-20 gm nude mice received topical treatments of 13 ul, 11 ul, 11 ul and 11 ul (total=46 ul) applied to a roughly 1 cm×1.5 cm area on the right flank, which was adjacent to the tumor xenograft. For these tumor xenograft experiments, a 5-fold increase in drug concentration over the minimum effective concentration previously shown to prevent radiodermatitis was tested.

With the last topical drug application, at −10 min, the mice also received an ip injection of Nembutal (65 ug/gm b.w.). An area adjacent to the topical application site, which contained the tumor xenograft site, then received 6.2 Gy (3.6 min) γ radiation from a Cs$^{137}$ irradiator (J. L. Shepherd). The irradiated site (1.5 cm×2 cm) was defined by a window in a lead plate (2.5 cm thick) placed between the mouse and the source.

For Cytoxan experiments, after the four topical applications over two hours, a single interperitoneal injection of 200 ug/gm b.w. Cytoxan (Meade Johnson) in water was administered.

Growth of the xenograft tumors was monitored by vernier caliper measurements every 1-2 days for the 18-21 days following irradiation. If tumors achieved areas of >200 mm$^2$ during this period the animal was euthanized.

Figure 11B:
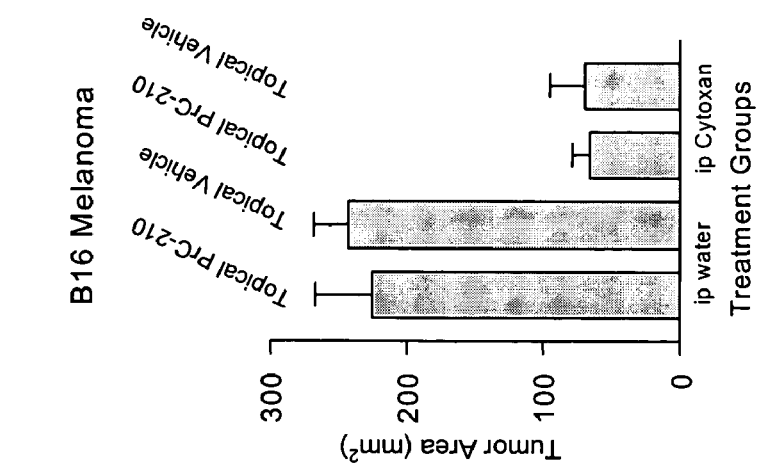
FIG. 11 presents the results of experiments designed to test the effect of certain compounds on the efficacy of exemplary cancer therapies. Panel A shows the effect of PrC-210 on killing of human epidermoid cells by external beam gamma irradiation. Panel B shows the effect of topical PrC-210 upon killing B16 melanoma tumor xenografts by systemic Cytoxan chemotherapy.
Figure 11A:
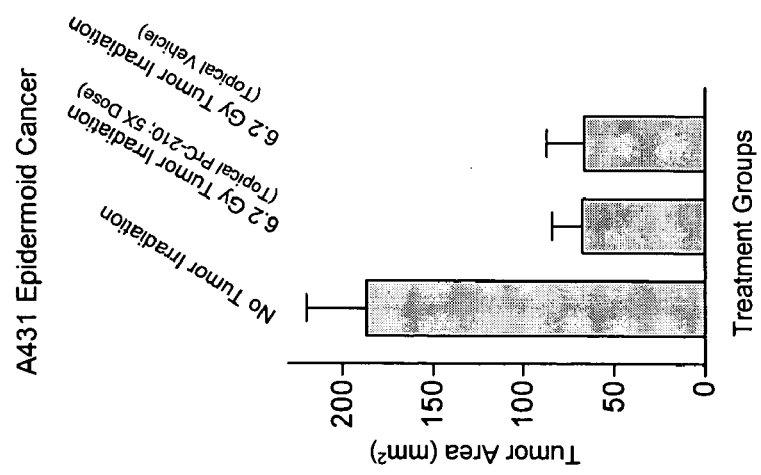

The results are presented in FIG. 11, panels A and B. Panel A shows that topical PrC-210, applied i) at a dose 5-times higher than the standard, effective, topical regimen ii) to a site adjacent to the tumor xenograft, has no discernible effect upon killing of A431 human epidermoid cells by external beam γ irradiation. The results in Panel B show that topical PrC-210, applied at a dose 5-times higher than the standard, effective, topical regimen, has no discernible effect upon killing B16 melanoma tumor xenografts by systemic Cytoxan chemotherapy.

EXAMPLE 9

The Aminothiols of the Present Invention Scavenge Oxygen Free Radicals

Figure 12:
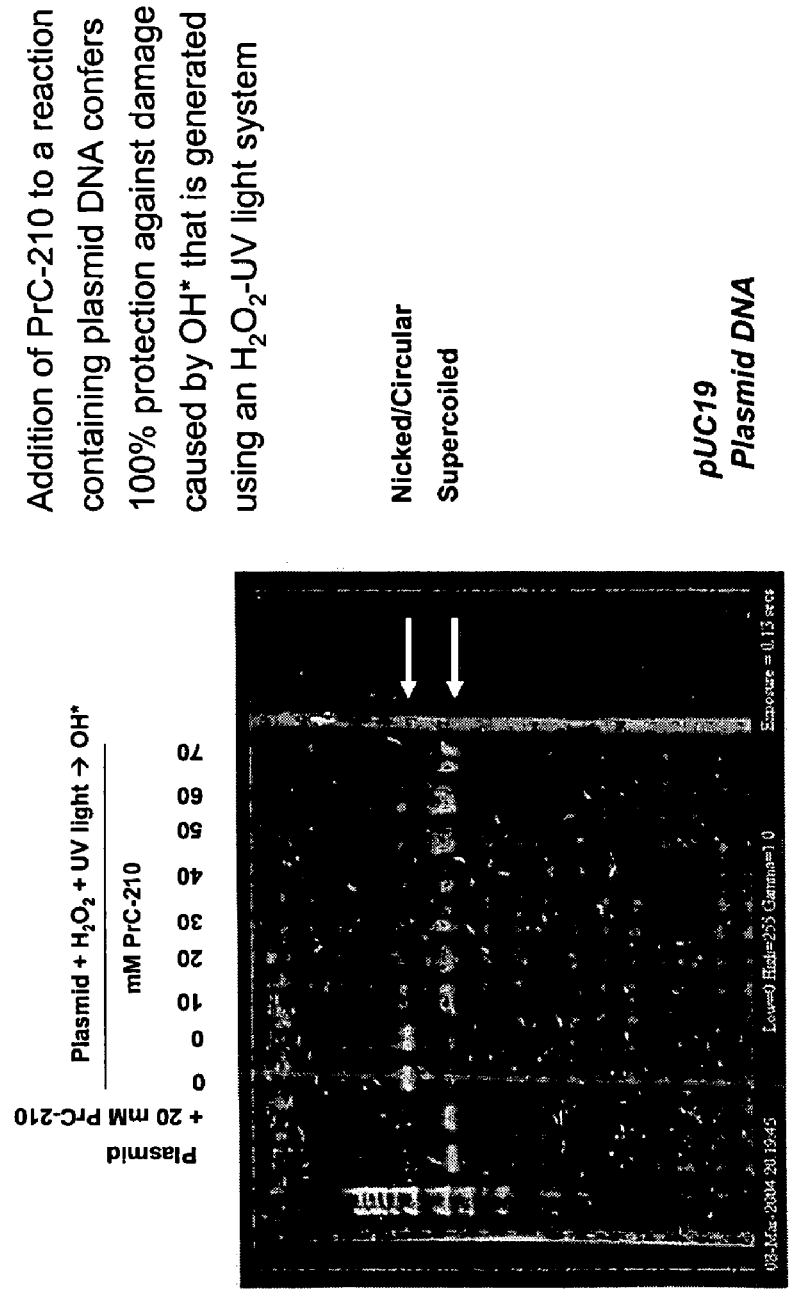
FIG. 12 presents data regarding the oxygen free radical scavenging activity of exemplary aminothiols.

FIG. 12 shows that in an in vitro reaction containing supercoiled pUC19 plasmid the addition of PrC-210 can completely protect the DNA against single-strand breaks that occur when the hydroxyl radical generated in the reaction is allowed to attack the plasmid DNA.

Method: 0.3 μg pUC19 plasmid was added to a 16 μl incubation containing Tris-EDTA buffer, then either PrC-210 (0-70 mM, pH 6.5) or buffer were added to the incubation. The polypropylene microtubes were then sealed and irradiated for 2.5 min at a distance of 80 cm from a UV lamp. Samples were then applied to 1% agarose gels and electrophoresed using methods known in the art. Data in FIG. 12 show that at even the lowest concentration tested, PrC-210 completely prevented damage to supercoiled DNA from the OH radical (OH*) generated in the reaction.

Figure 13:
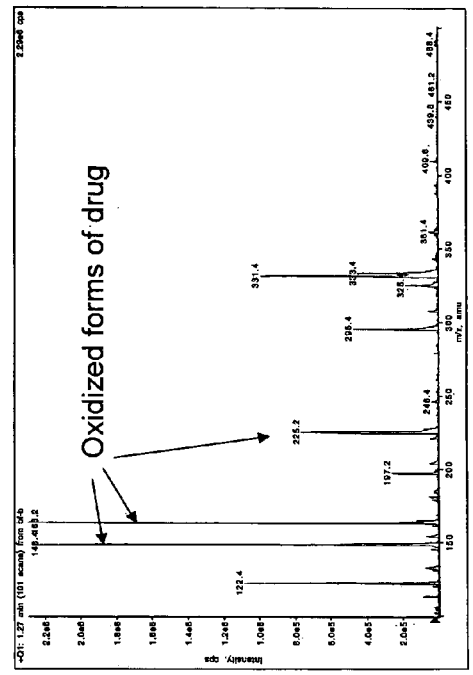
FIG. 13 presents mass spectral analysis of Pre-210 showing its conversion from a reduced to an oxidized form upon exposure to DNA/$H_2O_2$.
Figure 13:
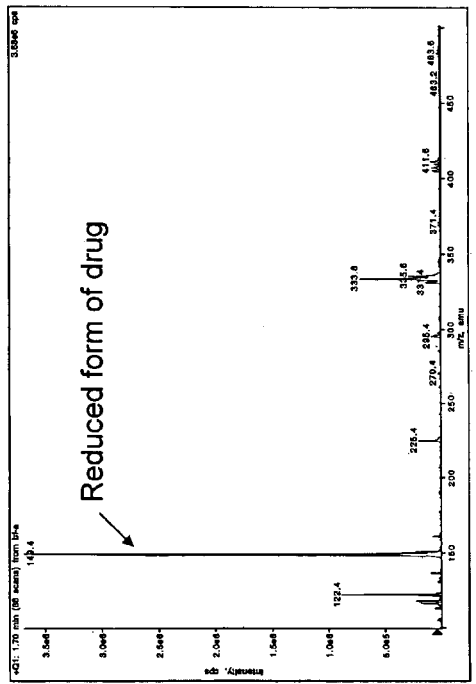

FIG. 13 shows mass spectrograms of the PrC-210 molecule withdrawn from the in vitro OH* incubations, either before UV radiation ("Reduced form of drug") or after UV radiation ("Oxidized forms of drug"). Respective masses indicate that the thiol (—SH) form of PrC-210 present before UV irradiation is converted to the disulfide (—S—S—) form as OH* is produced and then scavenged by PrC-210 in the in vitro reactions. Mass spectrograms were obtained at the mass spec. core facility in the University of Wisconsin Biotechnology Center.

EXAMPLE 10

Figure 14A:
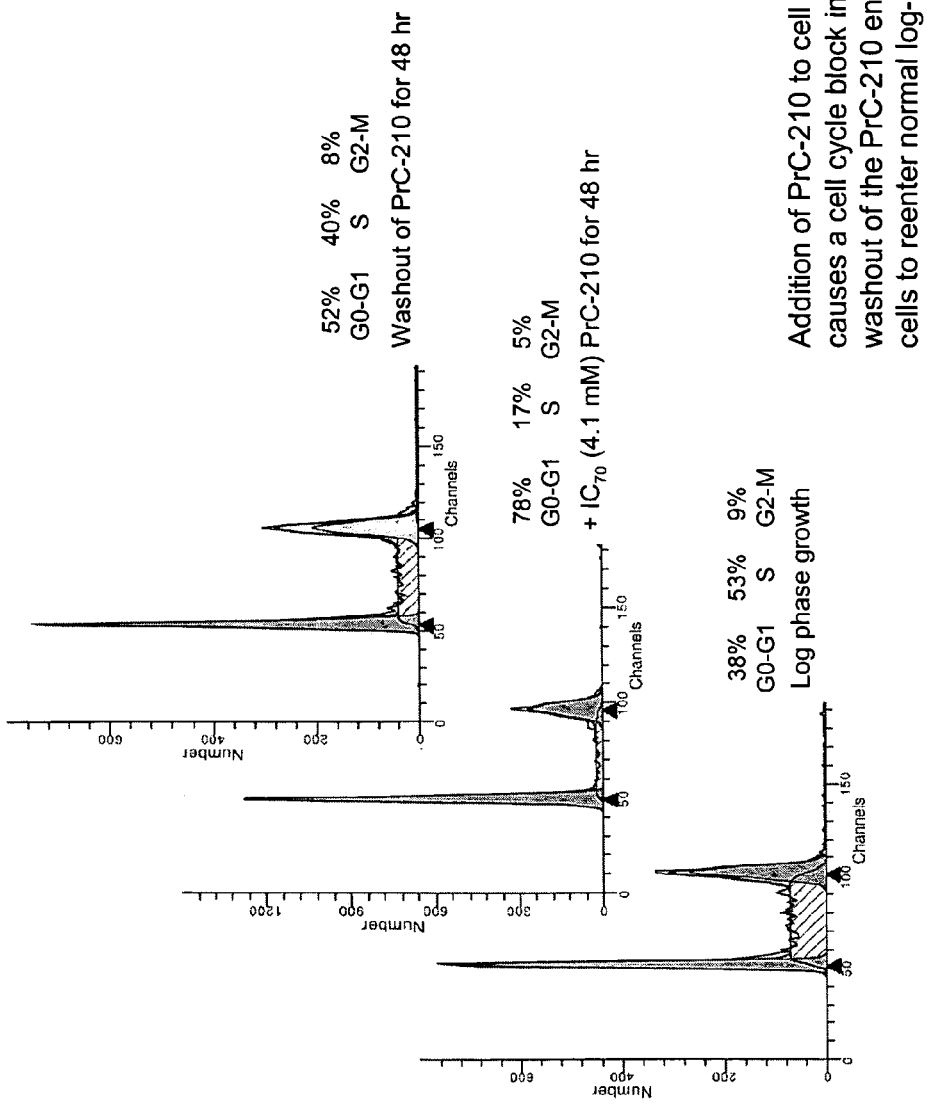
FIG. 14A presents flow cytometry data.

Aminothiols of the Present Invention Induce Reversible G1 Cell Cycle Block in Human Skin Cells The data in FIG. 14A illustrate that addition of PrC-210 to log-phase human fibroblast cell cultures results in a G1-specific cell cycle block and that "wash-out" of the drug by changing cell culture medium results in a reversion to normal cell division within 48 hours. This result is consistent with an earlier observation by Kramer et al. (*Cancer Research*. 57(24):5521-7, 1997) showing that addition of a polyamine like DENSPM to cell cultures also resulted in G1-specific cell cycle block that was reversible.

Figure 14B:
FIG. 14B presents Western blot data.

FIG. 14B shows the results of a western blot done to measure p21 levels in human fibroblasts pretreated with vehicle, PrC-210, cysteamine, colcemid (a positive control), or a cysteamine structural analog. Human skin fibroblasts treated with an $IC_{70}$ (concentration of PrC-210 that inhibits growth by 70 percent) concentration of PrC-210 showed a marked induction of p21 expression after a standard 30 hour exposure.

Figure 15:
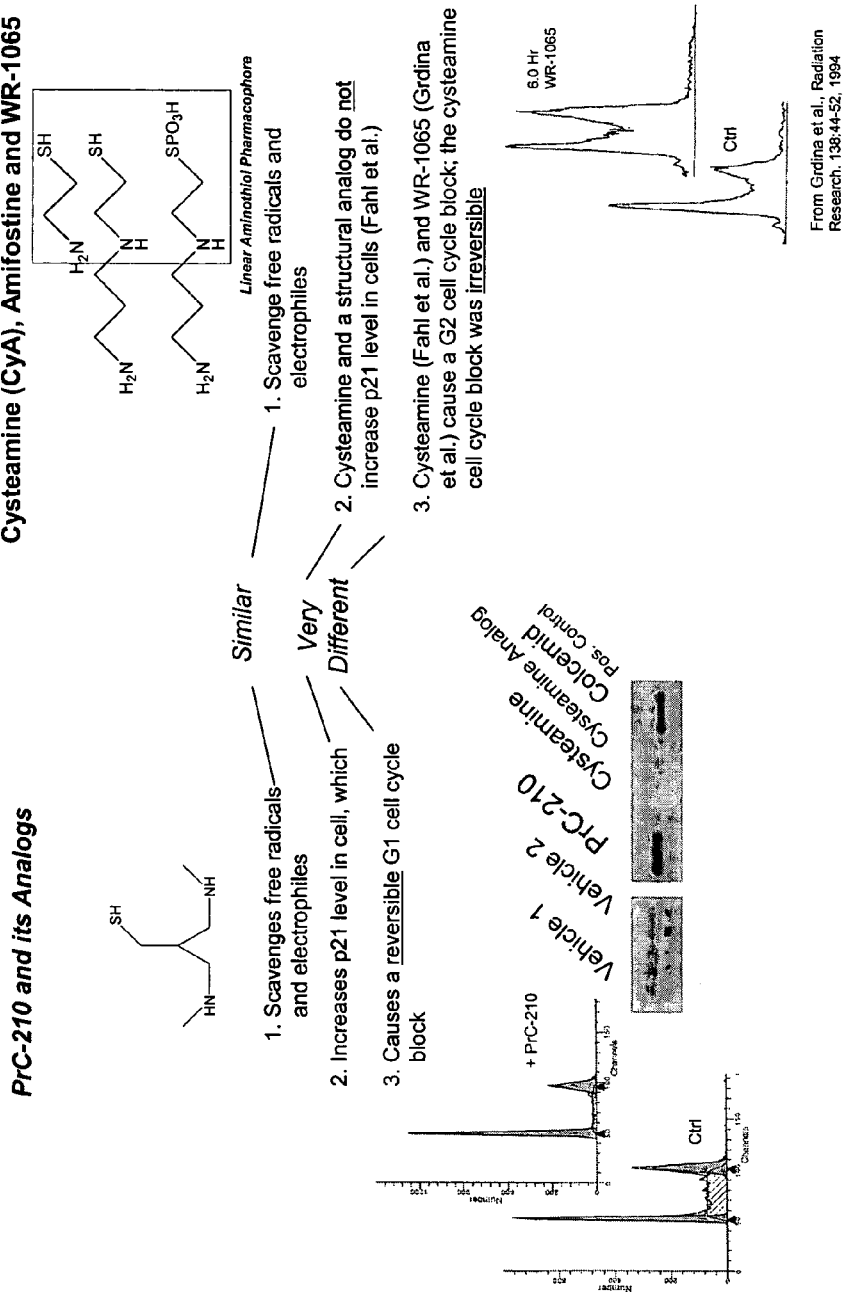
FIG. 15 presents data comparing the effects of Pre-210 to those of cysteamine, amifostine, and WR-1065 on cell cycle.

FIG. 15 shows a comparison between the inventive aminothiol, PrC-210, where the scavenging thiol group is projected or "displayed" away from the amine backbone that binds tightly to DNA, and the linear aminothiols, cysteamine, and WR-1065 and its parent molecule, amifostine, where both functional domains, i.e., thiol scavenger and DNA-interacting backbone, lie within the same plane, and functionally compete while positioned within the major groove of B-DNA. There are at least two clear, functional differences between the PrC-210 molecule and the linear aminothiols; i) PrC-210 induces p21 expression and cysteamine does not, and ii) PrC-210 causes a reversible G1 cell cycle block, whereas cysteamine and amifostine/WR-1065 cause a G2 cell cycle block that could not be reversed.

Methods (Cell cycle and p21 western): The cell culture experiments were done using primary, human skin fibroblasts, one strain of which (BJ cells) was obtained from ATCC (American Type Culture Collection). Cells were grown in DMEM containing 20% fetal bovine serum (Hyclone). For flow cytometry and p21 experiments, cells were plated at $0.5 \times 10^6$ cells/150 mm plate, and 24 hr later, drug molecules (4100 µM PrC-210, 600 µM cysteamine, 205 µM cysteamine analog, 0.4 µg/ml colcemid) were added to medium. After a 24 hr exposure (flow cytometry) or 30 hr exposure (p21 western), cells were harvested for the respective analyses as described by Kramer et al. (*Cancer Research*. 61(21):7754-62, 2001). As per the cited reference, cells were fixed, treated with RNAse, and stained with propidium iodide for flow cytometry, or cells were extracted, proteins electrophoresed, and probed with anti-p21 antibody (#SXM-30) for western blot analysis.

EXAMPLE 11

Figure 16:
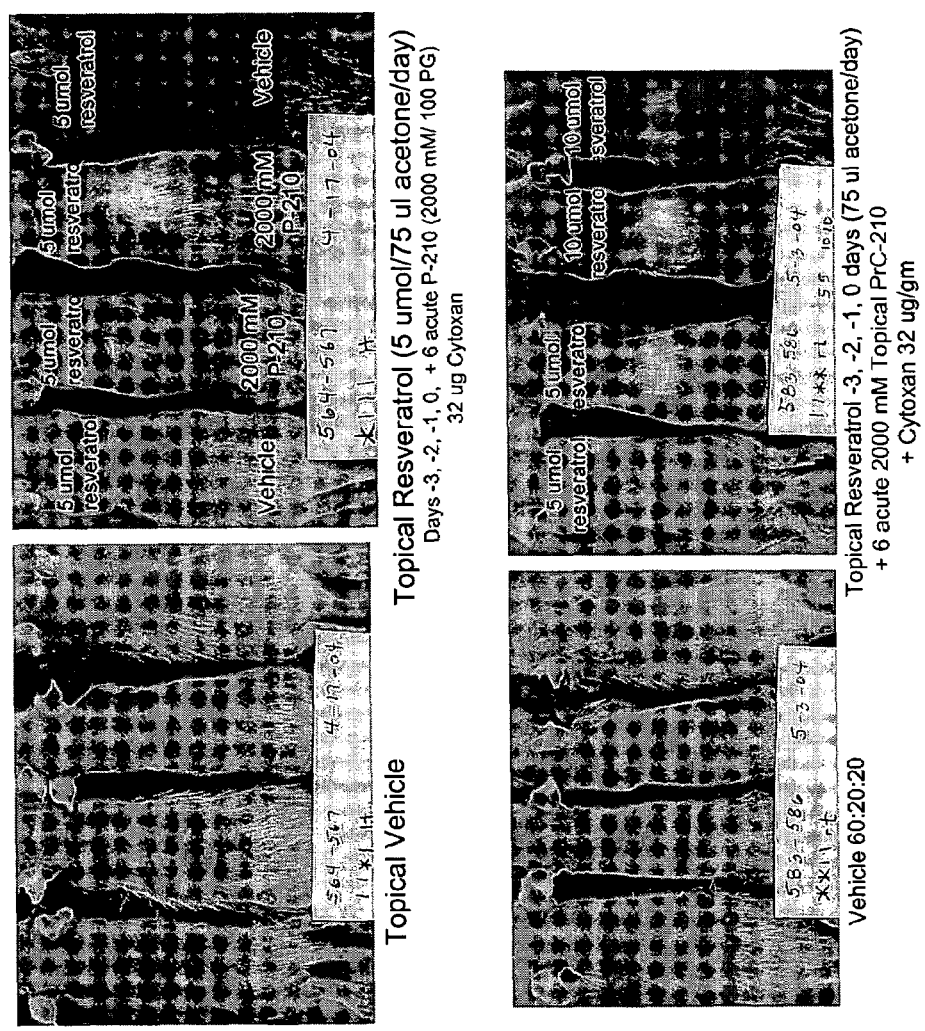
FIG. 16 shows results from a chemotherapy-induced alopecia experiment in neonate rats.

Topical Chemoprotector/Antioxidant Molecule Potentiates Aminothiol Efficacy in Alopecia Prevention FIG. 16 and Table 11-1 show results from a chemotherapy-induced alopecia experiment in neonate rats. These results indicate that three days of topical application of resveratrol, alone, under the conditions of this assay, had no discernible effect in preventing Cytoxan-induced alopecia, and topical PrC-210, alone, had a weak effect, but three days of topical pretreatment with resveratrol markedly potentiated the efficacy of topical PrC-210 in preventing Cytoxan-induced alopecia.

TABLE 11-1

| Experiment # (Cage #) | Topical Treatment | Alopecia-Inducing Agent | Alopecia Score (% Normal Coat Density in Topical Treatment Area) |
|---|---|---|---|
| 564-567 | Vehicle | ip Cytoxan 32 ug/gm b.w. | 4 |
|  | Resveratrol (5 umol/day) | ip Cytoxan 32 ug/gm b.w. | 5 |
|  | Resveratrol (5 umol/day) + PrC-210 (2000 mM) | ip Cytoxan 32 ug/gm b.w. | 44 |
| 583-586 | Vehicle | ip Cytoxan 32 ug/gm b.w. | 3 |
|  | Resveratrol (5 umol/day) + PrC-210 (2000 mM) | ip Cytoxan 32 ug/gm b.w. | 42 |
|  | Resveratrol (10 umol/day) + PrC-210 (2000 mM) | ip Cytoxan 32 ug/gm b.w. | 80 |
| 552-555 | Vehicle | ip Cytoxan 32 ug/gm b.w. | 1 |
|  | 2000 mM PrC-210 | ip Cytoxan 32 ug/gm b.w. | 9 |

Additional results using nucleic acid arrays demonstrated that topically treating neonate rat skin for 3-6 days with a related chemoprotector molecule (β-naphthaflavone) resulted in a substantial, coincident, activation of at least 40 different Phase I/Phase II/Phase III drug metabolizing/exporting gene products in the at-risk skin cells. Two examples of genes whose expression was induced following topical β-naphthaflavone treatment included, glutathione S-transferase (several separate isoforms that conjugate/detoxify drug electrophiles), and MRP (mdr-related protein, drug exporting membrane pump).

Method: To assess the ability of topical treatments to prevent Cytoxan-induced alopecia we used a published protocol (Hussein et al., Science. 249(4976):1564-6, 1990) in which 11 day old neonate rat pups (Sprague-Dawley) receive a total of 6 topical skin treatments of active agent(s) during the 5 hr before and 2 hr after a single ip dose of Cytoxan (32 ug/gm b.w.). The topical drug (2000 mM PrC-210) was dissolved in a vehicle formulation of 85:15 (propylene glycol:water). For the experiments of FIG. 16 and Table 5, the animals also received one topical application per day of resveratrol (in 75 ul acetone) for the three days preceding the Cytoxan dose that was administered on day 11 of life. The density of the rat coats in the topical treatment area was scored on day 18 of life for animals injected with Cytoxan.

TABLE 5

| Experiment # (Cage #) | Topical Treatment | Alopecia-Inducing Agent | Alopecia Score (% Normal Coat Density in Topical Treatment Area) |
|---|---|---|---|
| 564-567 | Vehicle | ip Cytoxan 32 ug/gm b.w. | 4 |
|  | Resveratrol (5 umol/day) | ip Cytoxan 32 ug/gm b.w. | 5 |
|  | Resveratrol (5 umol/day) + PrC-210 (2000 mM) | ip Cytoxan 32 ug/gm b.w. | 44 |
| 583-586 | Vehicle | ip Cytoxan 32 ug/gm b.w. | 3 |
|  | Resveratrol (5 umol/day) + PrC-210 (2000 mM) | ip Cytoxan 32 ug/gm b.w. | 42 |
|  | Resveratrol (10 umol/day) + PrC-210 (2000 mM) | ip Cytoxan 32 ug/gm b.w. | 80 |
| 552-555 | Vehicle | ip Cytoxan 32 ug/gm b.w. | 1 |
|  | 2000 mM PrC-210 | ip Cytoxan 32 ug/gm b.w. | 9 |

EXAMPLE 12

Effects of Delivery Vehicle Composition on Topical Aminothiol Efficacy

As shown in Table 6, increasing the ethanol content of the delivery vehicle from 0% to 50% markedly increased the efficacy of the same dose of PrC-210 in preventing radiation-induced dermatitis. Our current, preferred formulation for PrC-210 involves a 370 mM solution dissolved in a 50:30:20 (ethanol:propylene glycol:water) vehicle.

TABLE 6

| Experiment # (Cage #) | Topical Treatment | Vehicle Formulation ethanol:prop. glycol:water | Dermatitis Score (% of irradiated field free of scab material) |
|---|---|---|---|
| 440-443 | 740 mM PrC-210 | 0:95:5 | 68 |
| 626-629 | 740 mM PrC-210 | 50:30:20 | 96 ± 3 |
| 643-646 | 740 mM PrC-210 | 50:30:20 | 96 ± 4 |
| 440-443 | 370 mM PrC-210 | 0:95:5 | <50 |
| 574-577 | 370 mM PrC-210 | 50:30:20 | 100 ± 0 |
| 643-646 | 370 mM PrC-210 | 50:30:20 | 98 ± 3 |

Methods: Treatments were applied as described in Example 6. The dermatitis score was derived by estimating the percentage of the irradiated field that was free of scab material, so that no irradiation left an intact field of skin with a score of 100, and with very severe irradiation, the entire field was scrab-covered giving a score of "0."

In some cases, it may be useful to use a nitrogen or argon-purged delivery vehicle. For example,
i) In bathing the skin and the epidermal stem cells with a topical vehicle containing an aminothiol active, the $pO_2$ of the topical drug site may also be affected, particularly when the last topical application is 10 min before irradiation. By reducing the $pO_2$ the number of oxygen atoms available to form oxygen free radicals when the tissue is bombarded with energized photons from a γ radiation beam is also reduced. The γ beam sources include clinical linear accelerators (LINACs) and $Co^{60}$ sources that are used in the majority of human radiotherapy as well as the $Cs^{137}$ source used for experimental radiotherapy research.
ii) Aminothiol active agents are typically in the thiol, or —SH, form in order to act as oxygen free radical scavengers. Prolonged storage of PrC-210 in oxygenated solvent provides the oxygen that enables the spontaneous conversion of two moles of thiol (—SH) drug to one mole of disulfide (—S—S—) drug. Therefore, purging the vehicle of O2 is a logical way to promote drug stability.

Vigorous nitrogen purging of the vehicle solvent solutions for 3-5 min results in a 10-100 fold reduction in oxygen content (100% O2 tension to 1-10%) as measured by an $O_2$ electrode. One approach to nitrogen purging is to have a vacuum-sealed bottle that contains dry PrC-210 crystals and an accompanying bottle that contains de-gassed/purged delivery vehicle (presently, 50:30:20; ethanol:propylene glycol:water). Prior to irradiation, the health care practitioner mixes the two preparations, applies a sponge device to the top of the bottle, then squeezes the bottle to wet the sponge, and applies this material over the designated radiotherapy field. The bottle and its contents would be designed to cover a set area, so that the prescription would specify the number of units prescribed per week based upon the surface area of the field to be irradiated; these areas are generally known for head and neck patients, post breast cancer irradiation, etc.

In some cases, topical vasoconstrictors may be used to reduce the severity of cancer therapy side-effects. The utility of a topical vasoconstrictor in preventing cancer therapy side effects was initially identified by serendipity. Because cysteamine might have been toxic if distributed systemically at high concentrations in animals, a vasoconstrictor, in this case epinephrine (epinephrine-HCl, Sigma Chemical, 20 mM in topical 0:95:5 vehicle; ethanol:PG:water) was topically co-applied with cysteamine in an effort to prevent any potential uptake of the small aminothiol by skin vasculature. Test animals were kept in divided cages during topical applications to prevent ingestion of surface treatments from the skin of another animal, which can lead to systemic toxicity and possible misinterpretation of results. These initial experiments were done using a rat model where whole-body radiation is used to induce alopecia. This protocol is a variation of the Cytoxan-induced alopecia protocol described in Example 2. Here, 11 day old rat pups receive four topical treatments to their backs in the two hour period (at −2 hr, −1 hr, −30 min, −10 min) just prior to receiving whole-body irradiation (3.65 min) in a Cs137 irradiator. The topical treatments generally include volumes of 30 μl, 25 ul, 25 μl, 25 μl for the four, respective applications, and these are applied to an area of ~1 cm² just caudal to the shoulder blades. The topical vehicle varies from 0:95:5 (ethanol:PG: water) to 50:30:20, depending upon the solubility and concentration of the particular aminothiol. Because of the broad solubility shown by epinephrine-HCl, it generally does not determine selection of a particular topical vehicle. Following irradiation, the animals are housed with lactating mothers for 9 days and protection from radiation-induced alopecia within the topically-treated area is scored on day 20 of life. Protection is scored as the percentage of coat density seen in unirradiated rats.

In early experiments, 0-1000 mM epinephrine was added to topical aminothiol preparations, and it was observed in the control animals that topical epinephrine alone was also effective in preventing radiation-induced alopecia. The results from one of these experiments is summarized in Table 8. Here, epinephrine-HCl (FW:220) was dissolved in an ethanol:propylene glycol:water delivery vehicle and was applied four times in the two hours just prior to irradiating the 11 day old rat pups. The animals were then housed with lactating mothers until day 20 of life when the degree of protection conferred by the topical epinephrine was scored. Significant, dose-dependent protection was conferred by the four topical epinephrine treatments.

Co-application of a vasoconstrictor might allow other effective agents to remain concentrated on the epithelium, which would result in several beneficial effects. First, systemic side effects of co-applied agents would be diminished. Second, co-applied agents would remain more concentrated on the surface where they are intended to act, potentially improving their performance as well as reducing the effective dose required.

Co-application of epinephrine with the aminothiol formulation potentiates the efficacy of PrC-210 and its structural analog PrC-211 in preventing radiation-induced dermatitis.

For these experiments, 20 mM epinephrine-HCl (FW: 220) was dissolved in the topical formulation containing the indicated aminothiol in the 0:95:5 delivery vehicle. Rats received a total of four topical applications to their back at −2 hr, −1 hr, −30 min and −10 min and then received 8.7 Gy of γ irradiation at 0 min from a $Cs^{137}$ source. The severity of dermatitis was scored 13 days later. Though topical PrC-210 (~1200 mM) and PrC-211 (~2200 mM), alone, were shown to confer complete protection against radiodermatitis it was also observed that the addition of a low concentration of epinephrine (20 mM) directly to the topical aminothiol/vehicle formulation served to potentiate the aminothiol effect to 100% efficacy at significantly lower aminothiol concentrations (Table 7).

TABLE 7

| Experiment # (Cage #) | Topical Treatment | Vehicle Formulation ethanol:prop. glycol:water | Dermatitis Score (% of irradiated field free of scab material) | 20 mM Epinephrine-Conferred Effect |
| --- | --- | --- | --- | --- |
| 443 | Vehicle | 0:95:5 | 6 ± 2 | |
| 480 | 20 mM epinephrine | " | 20 ± 8 | |
| 440 | 900 mM PrC-210 | " | 68 ± 10 | |
| 478 | 900 mM PrC-210 + 20 mM epinephrine | " | 100 | +32% (68 -> 100%) |
| 441 | 1200 mM PrC-210 | " | 95 ± 5 | |
| 479 | 1200 mM PrC-210 + 20 mM epinephrine | " | 100 | +5% (95 -> 100%) |
| 488 | 1400 mM PrC-211 | " | 60 ± 12 | |
| | 1400 mM PrC-211 + 20 mM epinephrine | " | 100 | +40% (60 -> 100%) |

Radiation-Induced Alopecia

In Table 9, the topical application of epinephrine in the indicated 50:25:25 delivery vehicle provided clear, dose-dependent protection, within the topical treatment area, against the alopecia that developed following whole-body irradiation of the 11-day old rat pups.

TABLE 8

| Experiment # (Cage #) | Topical Treatment | Vehicle Formulation ethanol:prop. glycol:water | Alopecia-Inducing Agent | Alopecia Score (% Normal Coat Density in Topical Treatment Area) |
| --- | --- | --- | --- | --- |
| 647-650 | Vehicle | 50:25:25 | 3.65 min γ Irradiation ($Cs^{137}$ Source) | 1 ± 1 |
| | 20 mM epinephrine | " | 3.65 min γ Irradiation ($Cs^{137}$ Source) | 10 |
| | 100 mM epinephrine | " | 3.65 min γ Irradiation ($Cs^{137}$ Source) | 35 ± 19 |
| | 500 mM | " | 3.65 min γ | 43 ± 17 |

TABLE 8-continued

| Experiment # (Cage #) | Topical Treatment | Vehicle Formulation ethanol:prop. glycol:water | Alopecia-Inducing Agent | Alopecia Score (% Normal Coat Density in Topical Treatment Area) |
|---|---|---|---|---|
| | epinephrine | | Irradiation (Cs$^{137}$ Source) | |
| | 1000 mM epinephrine | " | 3.65 min γ Irradiation (Cs$^{137}$ Source) | 94 ± 6 |

The present invention is not limited to the embodiments described and exemplified above, but is capable of variation and modification within the scope of the appended claims.

What is claimed is:

1. A compound of Formula II:

$$Q^{NH}\underset{k}{\underbrace{Z}}^{NH}Q$$
                                                    I wherein:
A is a member selected from the group consisting of:

[structures shown]

J is a member selected from the group consisting of a single bond and —CH(Y)—;
L is a member selected from the group consisting of —CH$_2$X$^1$, —SH, and —CHX$^2$(X$^3$);
X$^1$ is a member selected from the group consisting of —SH and —R$^1$—SH;
X$^2$ and X$^3$ are each independently a member selected from the group consisting of —H, —SH and —R$^1$—SH, provided that at least one of X$^2$ and X$^3$ is other than —H or —SH;
Y is a member selected from the group consisting of —H, alkyl, and —R$^2$-D;
D is a member selected from the group consisting of —OH, —SR$^3$, and —NR$^3$R$^4$;
R$^3$ is a member selected from the group consisting of —H and lower alkyl;
R$^4$ is a member selected from the group consisting of —H, lower alkyl, and —R$^5$-D;
each Q is independently a member selected from the group consisting of —H, lower alkyl, and —R$^6$—SR$^3$, provided that when L is —SH, at least one of Q is other than —H; and
each R$^1$, R$^2$, R$^5$ and R$^6$ is independently C$_{1-6}$ alkylene; and,
or a stereoisomer, pharmaceutically-acceptable salt, monoprotonated acid salt or polyprotonated acid salt thereof.

2. A compound of claim 1, wherein A is a member selected from the group consisting of:

[structures shown]

3. A compound of claim 2, wherein Y is a member selected from the group consisting of —H and —R$^2$-D.
4. A compound of claim 3, wherein Y is —H.
5. A compound of claim 3, wherein Y is —R$^2$-D, wherein D is —SR$^3$, and wherein R$^3$ is —H.
6. A compound of claim 4, wherein X$^1$ is —SH.
7. A compound of claim 5, wherein X$^1$ is —SH.
8. A compound of claim 7 wherein each Q is independently a member selected from the group consisting of methyl and ethyl.
9. A compound of claim 1 wherein each Q is independently a member selected from the group consisting of —H and lower alkyl.
10. A compound of claim 9 wherein each Q is independently a member selected from the group consisting of methyl and ethyl.
11. A compound of claim 1, wherein A is:

[structure shown]

12. A compound of claim 11, wherein L is —CH$_2$X$^1$.

13. A compound of claim 11, wherein L is —SH.

14. A compound of claim 11, wherein J is —CH(Y).

15. A compound of claim 14, wherein Y is a member selected from the group consisting of —H and —R$^2$-D.

16. A compound of claim 15, wherein Y is —H.

17. A compound of claim 15, wherein Y is —R$^2$-D, wherein D is —SR$^3$, and wherein R$^3$ is —H.

18. A compound of claim 11, wherein Q is a member selected from the group consisting of H, methyl, and ethyl.

19. A compound of claim 11, wherein J is a single bond.

20. A compound of claim 19, wherein L is —CH$_2$X$^1$, and wherein X$^1$ is —SH.

21. A compound of claim 19 which is 3-methylamino-2-methylaminomethyl-propane-1-thiol or 3-amino-2-aminomethyl-propane-1-thiol.

22. A compound of claim 19, wherein L is —CH$_2$X$^1$, and wherein X$^1$ is —R$^1$—SH.

23. A compound of claim 19, wherein L is —SH.

24. A compound of claim 19, wherein Q is a member selected from the group consisting of —H, methyl, and ethyl.

25. A compound of claim 19, wherein L is —CHX$^2$(X$^3$).

26. A compound of claim 25, wherein X$^2$ is —R$^1$—SH, and wherein X$^3$ —R$^1$—SH.

27. A compound of claim 25, wherein X$^2$ is —SH, and wherein X$^3$ is —R$^1$—SH.

28. A compound of claim 12, wherein X$^1$ is —SH.

29. A compound of claim 12, wherein X$^1$ is —R$^1$—SH.

30. A pharmaceutical preparation for reducing or preventing hair loss, dermatitis, mucositis, or gastrointestinal distress caused by treatment with a chemotherapeutic agent or radiation therapy comprising:

a compound of Formula II according to

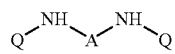

II wherein:

A is a member selected from the group consisting of:

J is a member selected from the group consisting of a single bond and —CH(Y)—;

L is a member selected from the group consisting of —CH$_2$X$^1$, —SH, and —CHX$^2$(X$^3$);

X$^1$ is a member selected from the group consisting of —SH and —R$^1$—SH;

X$^2$ and X$^3$ are each independently a member selected from the group consisting of —H, —SH and —R$^1$—SH, provided that at least one of X$^2$ and X$^3$ is other than —H or —SH;

Y is a member selected from the group consisting of —H, alkyl, and —R$^2$-D;

D is a member selected from the group consisting of —OH, —SR$^3$, and —NR$^3$R$^4$;

R$^3$ is a member selected from the group consisting of —H and lower alkyl;

R$^4$ is a member selected from the group consisting of —H, lower alkyl, and —R$^5$-D;

each Q is independently a member selected from the group consisting of —H, lower alkyl, and —R$^6$—SR$^3$, provided that when L is —SH, at least one of Q is other than —H; and, each R$^1$, R$^2$, R$^5$, and R$^6$ is independently C$_{1-6}$ alkylene; and, or a stereoisomer, pharmaceutically-acceptable salt, monoprotonated acid salt or polyprotonated acid salt thereof, and a topical delivery vehicle for locally delivering the compound to dermal or mucosal cells being a member selected from the group consisting of skin, scalp, mouth, nasoesophageal, gastrointestinal and urogenital system.

31. The pharmaceutical preparation of claim 30, further comprising at least one other agent that reduces or prevents hair loss, dermatitis, mucositis, or gastrointestinal distress caused by treatment with a chemotherapeutic agent or radiation therapy.

32. The pharmaceutical preparation of claim 30, further comprising an anti-proliferative agent.

33. The pharmaceutical preparation of claim 30, further comprising a chemoprotective inducing agent.

34. The pharmaceutical preparation of claim 30, further comprising a free radical scavenger.

35. The pharmaceutical preparation of claim 30, wherein the topical delivery vehicle comprises one or more members selected from the group consisting of liposomes, a lipid droplet emulsion, an oil, an aqueous emulsion of polyoxyethylene ethers, an aqueous alcohol mixture, an aqueous ethanol mixture containing propylene glycol, an aqueous ethanol mixture containing phosphatidyl choline, lysophosphatidyl choline and triglycerides, xanthan gum in aqueous buffer, hydroxypropymethylcellulose in aqueous buffer or aqueous alcohol mixture, diethylene glycol monoethyl ether in aqueous buffer, and biodegradable microparticles.

36. The pharmaceutical preparation of claim 35, for topical delivery to skin or hair follicles, wherein the delivery vehicle comprises an aqueous alcohol mixture.

37. The pharmaceutical preparation of claim 36, wherein the delivery vehicle further comprises propylene glycol.

38. The pharmaceutical preparation of claim 37, in the form of a member selected from the group consisting of a cream, lotion, ointment, and gel.

39. The pharmaceutical preparation of claim 35, for topical delivery to an oral cavity or naso-esophageal passage, wherein the delivery vehicle comprises a mucoadhesive substance.

40. The pharmaceutical preparation of claim 39, in the form of a member selected from the group consisting of an aerosol, oral rinse, ointment, and gel.

41. The pharmaceutical preparation of claim 35, for vaginal or rectal delivery, wherein the delivery vehicle comprises a mucoadhesive substance.

42. The pharmaceutical preparation of claim 41, in the form of a member selected from the group consisting of a cream, ointment, lotion, gel, foam, and suppository.

43. The pharmaceutical preparation of claim 35, for topical delivery to a gastrointestinal tract, wherein the delivery vehicle comprises one or more members selected from the group consisting of nonionic liposomes and mucoadhesive substances.

44. The pharmaceutical preparation of claim 43, in the form of a liquid for coating a surface of the gastrointestinal tract.

45. The pharmaceutical preparation of claim 30 further comprising a vasoconstrictor.

46. The pharmaceutical preparation of claim 45 for reducing or preventing hair loss.

47. The pharmaceutical preparation of claim 46, wherein the vasoconstrictor comprises one or more members selected from the group consisting of epinephrine, capoten, enalapril, lisinopril, zolmitriptan, tetrahydrozaline, phenylephrine, procainimide, and nitric oxide.

48. The pharmaceutical preparation of claim 47 wherein the vasoconstrictor comprises epinephrine.

49. The pharmaceutical preparation of claim 48 comprising 3-methylamino-2-methylaminomethyl-propane-1-thiol or 3-amino-2-aminomethyl-propane-1-thiol.

50. The pharmaceutical preparation of claim 45, wherein the vasoconstrictor is present in an amount effective for one or more members selected from the group consisting of restricting systemic distribution or absorption of the compound of Formula II, or a stereoisomer, pharmaceutically-acceptable salt, monoprotonated acid salt, or polyprotonated acid salt thereof; constricting surface blood vessels thereby prolonging the contact time with the compound of Formula II, or a stereoisomer, pharmaceutically-acceptable salt, monoprotonated acid salt, or polyprotonated acid salt thereof; transiently constricting skin blood vessels to reduce the amount of systemic chemotherapy arriving at epidermal and follicular matrix stem cells; and transiently constricting skin blood vessels to reduce the amount of oxygenated blood arriving at epidermal and follicular matrix stem cells.

51. The pharmaceutical preparation of claim 50 wherein the vasoconstrictor comprises epinephrine.

52. The pharmaceutical preparation of claim 51 wherein the epinephrine is present in an amount effective for restricting systemic distribution or absorption of the compound of Formula II, or a stereoisomer, pharmaceutically-acceptable salt, monoprotonated acid salt, or polyprotonated acid salt thereof.

53. A method for reducing or preventing hair loss, dermatitis, mucositis or gastrointestinal distress in a patient undergoing treatment with a chemotherapeutic agent or radiation therapy, comprising administering to the patient a prophylactically or therapeutically effective amount of a pharmaceutical preparation comprising:

the compound of Formula II according to

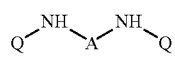

II wherein:

A is a member selected from the group consisting of:

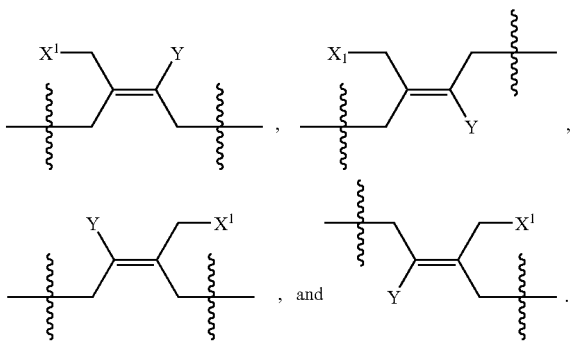

J is a member selected from the group consisting of a single bond and —CH(Y)—;

L is a member selected from the group consisting of —CH$_2$X$^1$, —SH, and —CHX$^2$(X$^3$);

X$^1$ is a member selected from the group consisting of —SH and —R$^1$—SH;

X$^2$ and X$^3$ are each independently a member selected from the group consisting of —H, —SH and —R$^1$—SH, provided that at least one of X$^2$ and X$^3$ is other than —H or —SH;

Y is a member selected from the group consisting of —H, alkyl, and —R$^2$-D;

D is a member selected from the group consisting of —OH, —SR$^3$, and —NR$^3$R$^4$;

R$^3$ is a member selected from the group consisting of —H and lower alkyl;

R$^4$ is a member selected from the group consisting of —H, lower alkyl, and —R$^5$—D;

each Q is independently a member selected from the group consisting of —H, lower alkyl, and —R$^6$—SR$^3$, provided that when L is —SH, at least one of Q is other than —H; and, each R$^1$, R$^2$, R$^5$, and R$^6$ is independently C$_{1-6}$ alkylene; and, or a stereoisomer, pharmaceutically-acceptable salt, monoprotonated acid salt or polyprotonated acid salt thereof, and a topical delivery vehicle for locally delivering the compound to dermal or mucosal cell members being selected from the group consisting of skin, scalp, mouth, nasoesophageal, gastrointestinal and urogenital system.

54. The method of claim 53, comprising administering the pharmaceutical preparation beginning at least thirty minutes prior to chemotherapy or radiation therapy.

55. The method of claim 54, comprising administering the pharmaceutical preparation beginning at least one day prior to chemotherapy or radiation therapy.

56. The method of claim 53, comprising administering the pharmaceutical preparation after initiation of chemotherapy or radiation therapy.

57. The method of claim 53, comprising administering the pharmaceutical preparation periodically or continuously throughout a course of chemotherapy or radiation therapy.

58. The method of claim 54, comprising administering the pharmaceutical preparation following termination of a course of chemotherapy or radiation therapy.

59. The method of claim 53, further comprising administering to the patient at least one other agent that reduces or prevents hair loss, dermatitis, mucositis or gastrointestinal distress caused by treatment with a chemotherapeutic agent or radiation therapy.

60. The method of claim 59, wherein the other agent is an anti-proliferative agent.

61. The method of claim 59, wherein the other agent is a chemoprotective inducing agent.

62. The method of claim 59, wherein the other agent is a free radical scavenger.

63. The method of claim 53 wherein the pharmaceutical preparation further comprises a vasoconstrictor.

64. The method of claim 63 for reducing or preventing hair loss.

65. The method of claim 64 wherein the vasoconstrictor comprises one or more members selected from the group consisting of epinephrine, capoten, enalapril, lisinopril, zolmitriptan, tetrahydrozaline, phenylephrine, procainimide, and nitric oxide.

66. The method of claim 65 wherein the vasoconstrictor comprises epinephrine.

67. The method of claim 66 comprising 3-methylamino-2-methylaminomethyl-propane-1-thiol or 3-amino-2-aminomethyl-propane-1-thiol.

68. The method of claim 63, wherein the vasoconstrictor is present in an amount effective for one or more members selected from the group consisting of restricting systemic distribution or absorption of the compound; constricting surface blood vessels thereby prolonging the contact time with the compound; transiently constricting skin blood vessels to reduce the amount of systemic chemotherapy arriving at epidermal and follicular matrix stem cells; and transiently constricting skin blood vessels to reduce the amount of oxygenated blood arriving at epidermal and follicular matrix stem cells.

69. The method of claim 68 wherein the vasoconstrictor comprises epinephrine.

70. The method of claim 69 wherein the epinephrine is present in an amount effective for restricting systemic distribution or absorption of the compound of Formula II, or a stereoisomer, pharmaceutically-acceptable salt, monoprotonated acid salt or polyprotonated acid salt thereof.

71. A method of increasing a patient's tolerance to a chemotherapeutic agent or radiation therapy comprising:

administering the chemotherapeutic agent or radiation therapy to the patient; and administering a pharmaceutical preparation comprising:

a compound of Formula II according to

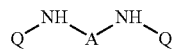

wherein:

A is a member selected from the group consisting of:

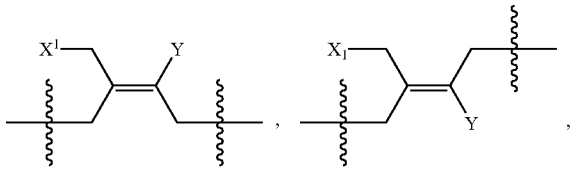

-continued

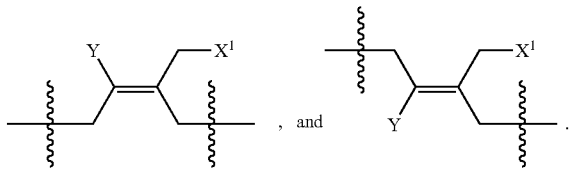

J is a member selected from the group consisting of a single bond and —CH(Y)—;

L is a member selected from the group consisting of —CH$_2$X$^1$, —SH, and —CHX$^2$(X$^3$);

X$^1$ is a member selected from the group consisting of —SH and —R$^1$—SH;

X$^2$ and X$^3$ are each independently a member selected from the group consisting of —H, —SH and —R$^1$—SH, provided that at least one of X$^2$ and X$^3$ other than —H or —SH;

Y is a member selected from the group consisting of —H, alkyl, and —R$^2$-D;

D is a member selected from the group consisting of —OH, —SR$^3$, and —NR$^3$R$^4$;

R$^3$ is a member selected from the group consisting of —H and lower alkyl;

R$^4$ is a member selected from the group consisting of —H, lower alkyl, and —R$^5$-D;

each Q is independently a member selected from the group consisting of —H, lower alkyl, and —R$^6$—SR$^3$, provided that when L is —SH, at least one of Q is other than —H; and, each R$^1$, R$^2$, R$^5$, and R$^6$ is independently C$_{1-6}$ alkylene; and, or a stereoisomer, pharmaceutically-acceptable salt, monoprotonated acid salt or polyprotonated acid salt thereof, and a topical delivery vehicle for locally delivering the compound to dermal or mucosal cells being a member selected from the group consisting of skin, scalp, mouth, nasoesophageal, gastrointestinal and urogenital system, wherein the pharmaceutical preparation is administered one or more times, in an amount and for a time effective, to the patient for reducing or preventing one or more members selected from the group consisting of chemotherapy- or radiation therapy-induced hair loss, dermatitis, mucositis and gastrointestinal distress, thereby increasing the patient's tolerance to the chemotherapeutic agent or radiation therapy.

* * * * *

UNITED STATES PATENT AND TRADEMARK OFFICE
CERTIFICATE OF CORRECTION

PATENT NO. : 7,314,959 B2
APPLICATION NO. : 10/915089
DATED : January 1, 2008
INVENTOR(S) : Fahl et al.

Page 1 of 1

It is certified that error appears in the above-identified patent and that said Letters Patent is hereby corrected as shown below:

In the Claims

Column 73, Line 22, Claim 1: Please correct "Z" in formula II to "A", and please remove ( )k from formula II.

Column 75, Line 42, Claim 30: Please insert the group of 5 structures found in Claim 1, Column 73, Lines 30-47, following the phrase "A is a member selected from the group consisting of:"

Column 77, Line 63, Claim 53: Please insert the structure of Claim 1, Lines 43-48, that includes "J" and "L" into the group of structures illustrated in Column 77, Lines 48-62.

Column 80, Line 9, Claim 71: Please insert the structure of Claim 1, Lines 43-48, that includes "J" and "L" into the group of structures illustrated in Column 79/80, Lines 43-50, 1-8.

Signed and Sealed this
Thirtieth Day of April, 2019

Andrei Iancu
*Director of the United States Patent and Trademark Office*

UNITED STATES PATENT AND TRADEMARK OFFICE
CERTIFICATE OF CORRECTION

PATENT NO. : 7,314,959 B2
APPLICATION NO. : 10/915089
DATED : January 1, 2008
INVENTOR(S) : William E. Fahl et al.

Page 1 of 1

It is certified that error appears in the above-identified patent and that said Letters Patent is hereby corrected as shown below:

In the Specification

Column 1, Lines 11-15:
Delete the phrase:
"Pursuant to 35 U.S.C. §202 (c), it is acknowledged that the United States Government
has certain rights in the invention described herein, which was made in part with funds from the
National Institutes of Health, Grant No. CA22484."
And replace with:
--REFERENCE TO GOVERNMENT RIGHTS
This invention was made with government support under CA022484 awarded by the
National Institutes of Health. The government has certain rights in the invention.--.

Signed and Sealed this
Eighth Day of December, 2020

Andrei Iancu
*Director of the United States Patent and Trademark Office*